United States Patent
Bolin et al.

(10) Patent No.: US 8,324,385 B2
(45) Date of Patent: Dec. 4, 2012

(54) DIACYLGLYCEROL ACYLTRANSFERASE INHIBITORS

(75) Inventors: David Robert Bolin, Montclair, NJ (US); Adrian Wai-Hing Cheung, Glen Rock, NJ (US); Matthew Michael Hamilton, Hackettsown, NJ (US); Nicholas Marcopulos, North Caldwell, NJ (US); Lee Apostle McDermott, East Windsor, NJ (US); Yimin Qian, Wayne, NJ (US)

(73) Assignee: Madrigal Pharmaceuticals, Inc., Fort Washington, PA (US)

( * ) Notice: Subject to any disclaimer, the term of this patent is extended or adjusted under 35 U.S.C. 154(b) by 229 days.

(21) Appl. No.: 12/581,950

(22) Filed: Oct. 20, 2009

(65) Prior Publication Data
US 2010/0113782 A1    May 6, 2010

Related U.S. Application Data

(60) Provisional application No. 61/109,589, filed on Oct. 30, 2008.

(51) Int. Cl.
*C07D 401/00* (2006.01)
*C07D 403/00* (2006.01)
*C07D 405/00* (2006.01)
*C07D 409/00* (2006.01)

(52) U.S. Cl. .................................. 544/360; 544/364
(58) Field of Classification Search .................. None
See application file for complete search history.

(56) References Cited

U.S. PATENT DOCUMENTS

| | | | |
|---|---|---|---|
| 3,250,771 A | 5/1966 | Leonard et al. | |
| 3,863,007 A | 1/1975 | Warner, Jr. | |
| 3,929,793 A | 12/1975 | Popelak et al. | |
| 4,066,654 A | 1/1978 | Adelstein et al. | |
| 6,498,190 B1 | 12/2002 | Ohtani | |
| 6,984,652 B2 | 1/2006 | Yager | |
| 7,015,218 B1 | 3/2006 | Ushio et al. | |
| 7,094,896 B2 | 8/2006 | Ding et al. | |
| 7,148,246 B2 | 12/2006 | Gretzke et al. | |
| 7,160,911 B2 | 1/2007 | Goerlitzer et al. | |
| 7,244,727 B2 | 7/2007 | Fox et al. | |
| 7,317,125 B2 | 1/2008 | Bolin et al. | |
| 7,714,126 B2 | 5/2010 | Bolin et al. | |
| 8,058,299 B2 | 11/2011 | Bolin et al. | |
| 8,115,011 B2 | 2/2012 | Bolin et al. | |
| 2004/0019067 A1 | 1/2004 | Armistead et al. | |
| 2007/0021453 A1 | 1/2007 | Yamakawa et al. | |
| 2007/0032529 A1 | 2/2007 | Takagi | |
| 2007/0123504 A1 | 5/2007 | Bolin et al. | |
| 2008/0096874 A1 | 4/2008 | Birch et al. | |
| 2009/0036420 A1 * | 2/2009 | Galley et al. | 514/210.2 |
| 2009/0093497 A1 | 4/2009 | Bolin et al. | |
| 2009/0099201 A1 | 4/2009 | Bolin et al. | |
| 2009/0105273 A1 | 4/2009 | Bolin et al. | |
| 2009/0170864 A1 | 7/2009 | Bolin et al. | |
| 2010/0035864 A1 | 2/2010 | Bolin et al. | |
| 2010/0145047 A1 | 6/2010 | Bolin et al. | |
| 2010/0152445 A1 | 6/2010 | Bolin et al. | |

FOREIGN PATENT DOCUMENTS

| | | |
|---|---|---|
| AU | 2002333456 A2 | 3/2003 |
| CA | 2458210 A1 | 3/2003 |
| EP | 1535915 A1 | 6/2005 |
| WO | WO-0047558 A1 | 8/2000 |
| WO | WO-03020269 A1 | 3/2003 |
| WO | WO 03092686 A1 * | 11/2003 |
| WO | 2006047516 A2 | 5/2006 |
| WO | WO-2006134317 A1 | 12/2006 |
| WO | WO 2007008541 A2 * | 1/2007 |
| WO | WO-2007060140 A2 | 5/2007 |
| WO | WO-2007141538 A1 | 12/2007 |
| WO | WO-2008098851 A1 | 8/2008 |
| WO | WO-2008141976 A1 | 11/2008 |
| WO | WO-2010017040 A1 | 2/2010 |
| WO | WO-2010065310 A1 | 6/2010 |
| WO | WO-2010077861 A1 | 7/2010 |

OTHER PUBLICATIONS

Hamblett, CL. et al. The discovery of 6-amino nicotinamides as potent and selective histone deacetylase inhibitors. Bioorganic & Medicinal Chemistry Letters. 2007, vol. 17, p. 5302.*

The International Search Report and Written Opinion by the International Searching Authority, issued on Jan. 12, 2010, in the PCT application No. PCT/US09/62154.

Clark et al. "Synthesis and Anticonvulsant Activity of Analogues of 4-Amino-N-(1-phenylethyl)benzamide." J. Med. Chem. 30.7(1987):1214-1218.

Lynch et al. "Synthesis and Activity of Four (N,N-dimethylamino)benzamide Non-Steroidal Anti-Inflammatory Drugs Based on Thiazole and Thiazoline." J. Heterocyclic Chem. 43(2006):191-197.

* cited by examiner

*Primary Examiner* — Rita Desai
*Assistant Examiner* — Ben S Michelson
(74) *Attorney, Agent, or Firm* — Mintz Levin Cohn Ferris Glovsky and Popeo, P.C.; Ivor R. Elrifi; Heidi A. Erlacher

(57) ABSTRACT

Provided herein are compounds of the formula (I):

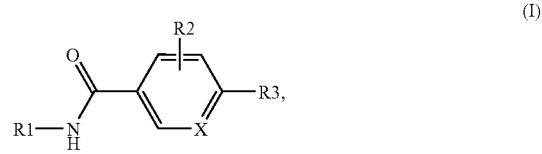

were RI is phenyl, R2 is hydrogen, halogen or lower alkyl, X is carbon on nitrogen, and R3 is isoquinoline, -amino, or a -4- to 6-membered heterocycloalkyl ring and pharmaceutically acceptable salts thereof, which are active as DGAT inhibitors and therefore find uses in treatment of diseases associated with abnormal metabolism of trigliceride. such as, for example, obesity, type II diabetes mellitus and metabolic syndrome.

13 Claims, No Drawings

DIACYLGLYCEROL ACYLTRANSFERASE INHIBITORS

CROSS-REFERENCE TO RELATED APPLICATIONS

This application claims priority from Provisional Patent Application No. 61/109,589 filed Oct. 30, 2008. The above mentioned application is incorporated herein by reference.

FIELD OF THE INVENTION

The invention involves inhibitors of diacylglycerol acyltransferase. The inhibitors are useful for the treatment of diseases such as obesity, type II diabetes mellitus, dyslipidemia and metabolic syndrome.

All documents cited or relied upon below are expressly incorporated herein by reference.

BACKGROUND OF THE INVENTION

Triglycerides or triacylglycerols are the major form of energy storage in eukaryotic organisms. In mammals, these compounds are primarily synthesized in three tissues: the small intestine, liver, and adipocytes. Triglycerides or triacylglycerols support the major functions of dietary fat absorption, packaging of newly synthesized fatty acids and storage in fat tissue (see Subauste and Burant, Current Drug Targets—Immune, Endocrine & Metabolic Disorders (2003) 3, 263-270).

Diacylglycerol O-acyltransferase, also known as diglyceride acyltransferase or DGAT, is a key enzyme in triglyceride synthesis. DGAT catalyzes the final and rate-limiting step in triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, 395-400).

DGAT has a specificity for sn-1,2 diacylglycerols and will accept a wide variety of fatty acyl chain lengths (see Farese et al, Current Opinions in Lipidology (2000) 11, 229-234). DGAT activity levels increase in fat cells as they differentiate in vitro and recent evidence suggests that DGAT may be regulated in adipose tissue post-transcriptionally (see Coleman et al, Journal of Molecular Biology (1978) 253, 7256-7261 and Yu et al, Journal of Molecular Biology (2002) 277, 50876-50884). DGAT activity is primarily expressed in the endoplasmic reticulum (see Colman, Methods in Enzymology (1992) 209, 98-104). In hepatocytes, DGAT activity has been shown to be expressed on both the cytosolic and luminal surfaces of the endoplasmic reticular membrane (see Owen et al, Biochemical Journal (1997) 323 (pt 1), 17-21 and Waterman et al, Journal of Lipid Research (2002) 43, 1555-156). In the liver, the regulation of triglyceride synthesis and partitioning, between retention as cytosolic droplets and secretion, is of primary importance in determining the rate of VLDL production (see Shelness and Sellers, Current Opinions in Lipidology (2001) 12, 151-157 and Owen et al, Biochemical Journal (1997) 323 (pt 1), 17-21).

Two forms of DGAT have been cloned and are designated DGAT1 and DGAT2 (see Cases et al, Proceedings of the National Academy of Science, USA (1998) 95, 13018-13023, Lardizabal et al, Journal of Biological Chemistry (2001) 276, 38862-38869 and Cases et al, Journal of Biological Chemistry (2001) 276, 38870-38876). Although both enzymes utilize the same substrates, there is no homology between DGAT1 and DGAT2. Both enzymes are widely expressed however some differences do exist in the relative abundance of expression in various tissues.

The gene encoding mouse DGAT1 has been used to create DGAT knock-out. These mice, although unable to express a functional DGAT enzyme (Dgat−/− mice), are viable and continue to synthesize triglycerides (see Smith et al, Nature Genetics (2000) 25, 87-90). This would suggest that multiple catalytic mechanisms contribute to triglyceride synthesis, such as DGAT2. An alternative pathway has also been shown to form triglycerides from two diacylglycerols by the action of diacylglycerol transacylase (see Lehner and Kuksis, Progress in Lipid Research (1996) 35, 169-210).

Dgat−/− mice are resistant to diet-induced obesity and remain lean. When fed a high fat diet, Dgat−/− mice maintain weights comparable to mice fed a diet with regular fat content. Dgat−/− mice have lower tissue triglyceride levels. The resistance to weight gain seen in the knockout mice, which have a slightly higher food intake, is due to an increased energy expenditure and increased sensitivity to insulin and leptin (see Smith et al, Nature Genetics (2000) 25, 87-90, Chen and Farese, Trends in Cardiovascular Medicine (2000) 10, 188-192, Chen and Farese, Current Opinions in Clinical Nutrition and Metabolic Care (2002) 5, 359-363 and Chen et al, Journal of Clinical Investigation (2002) 109, 1049-1055). Dgat−/− mice have reduced rates of triglyceride absorption, improved triglyceride metabolism, and improved glucose metabolism, with lower glucose and insulin levels following a glucose load, in comparison to wild-type mice (see Buhman et al, Journal of Biological Chemistry (2002) 277, 25474-25479 and Chen and Farese, Trends in Cardiovascular Medicine (2000) 10, 188-192).

Disorders or imbalances in triglyceride metabolism, both absorption as well as de novo synthesis, have been implicated in the pathogenesis of a variety of disease risks. These include obesity, insulin resistance syndrome, type II diabetes, dyslipidemia, metabolic syndrome (syndrome X) and coronary heart disease (see Kahn, Nature Genetics (2000) 25, 6-7, Yanovski and Yanovski, New England Journal of Medicine (2002) 346, 591-602, Lewis et al, Endocrine Reviews (2002) 23, 201, Brazil, Nature Reviews Drug Discovery (2002) 1, 408, Malloy and Kane, Advances in Internal Medicine (2001) 47, 111, Subauste and Burant, Current Drug Targets Immune, Endocrine & Metabolic Disorders (2003) 3, 263-270 and Yu and Ginsberg, Annals of Medicine (2004) 36, 252-261). Compounds that can decrease the synthesis of triglycerides from diacylglycerol by inhibiting or lowering the activity of the DGAT enzyme would be of value as therapeutic agents for the treatment of diseases associated with abnormal metabolism of triglycerides.

Known inhibitors of DGAT include: dibenzoxazepinones (see Ramharack, et al, EP1219716 and Burrows et al, 26th National Medicinal Chemistry Symposium (1998) poster C-22), substituted amino-pyrimidino-oxazines (see Fox at al, WO2004047755), chalcones such as xanthohumol (see Tabata et al, Phytochemistry (1997) 46, 683-687 and Casaschi et al, Journal of Nutrition (2004) 134, 1340-1346), substituted benzyl-phosphonates (see Kurogi et al, Journal of Medicinal Chemistry (1996) 39, 1433-1437, Goto, et al, Chemistry and Pharmaceutical Bulletin (1996) 44, 547-551, Ikeda, et al, Thirteenth International Symposium on Atherosclerosis (2003), abstract 2P-0401, and Miyata, et al, JP 2004067635), aryl alkyl acid derivatives (see Smith et al, WO2004100881 and US20040224997), furan and thiophene derivatives (see WO2004022551), pyrrolo[1,2b]pyridazine derivatives (see Fox et al, WO2005103907), substituted sulfonamides (see Budd Haeberlein and Buckett, WO20050442500), thiophenoxyacetamides (see Bolin and Michoud, WO2006082010), arylpropionylhydrazides (see Michoud, WO2006120125) and oxazoledicarboxamides (see Bolin et al, WO2007060140). Most recently, DGAT inhibitors demonstrated efficacy of body weight gain inhibition in obese animal models (Journal of Medicinal Chemistry (2008), 51, 380).

Also known to be inhibitors of DGAT are: 2-bromo-palmitic acid (see Colman et al, Biochimica et Biophysica Acta (1992) 1125, 203-9), 2-bromo-octanoic acid (see Mayorek and Bar-Tana, Journal of Biological Chemistry (1985) 260, 6528-6532), roselipins (see Noriko et al, (Journal of Antibiotics (1999) 52, 815-826), amidepsin (see Tomoda et al, Journal of Antibiotics (1995) 48, 942-7), isochromophilone, prenylflavonoids (see Chung et al, Planta Medica (2004) 70, 258-260), polyacetylenes (see Lee et al, Planta Medica (2004) 70, 197-200), cochlioquinones (see Lee et al, Journal of Antibiotics (2003) 56, 967-969), tanshinones (see Ko et al, Archives of Pharmaceutical Research (2002) 25, 446-448), gemfibrozil (see Zhu et al, Atherosclerosis (2002) 164, 221-228), and substituted quinolones (see Ko, et al, Planta Medica (2002) 68, 1131-1133). Also known to be modulators of DGAT activity are antisense oligonucleotides (see Monia and Graham, US20040185559).

A need exists in the art, however, for additional DGAT inhibitors that have efficacy for the treatment of metabolic disorders such as, for example, obesity, type II diabetes mellitus and metabolic syndrome.

SUMMARY OF THE INVENTION

The present invention pertains to DGAT inhibitors. In a preferred embodiment, the invention provides for compounds of the formula (I):

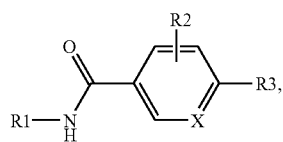

(I)

as well as pharmaceutically acceptable salts thereof, and pharmaceutical compositions thereof.

DETAILED DESCRIPTION OF THE INVENTION

In a preferred embodiment of the present invention, provided are compounds of formula (I):

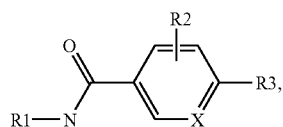

(I)

wherein:
X is carbon or nitrogen;
R1 is -phenyl, unsubstituted, mono- or di-substituted independently with halogen, lower alkyl, lower alkoxy, lower alkanoic acid, lower alkanoyl, lower alkanoic acid lower alkyl-ester, haloloweralkyl, unsubstituted phenyl, alkoxyphenyl, halophenyl, or haloloweralkyl-phenyl, -heteroaryl substituent containing from 1 to three rings and from 5 to 12 carbon atoms with at least one ring containing from one to three ring hetero atoms independently selected from the group consisting of O, N and S, with said heteroaryl rings being, unsubstituted or mono- or di-substituted independently with phenyl, lower alkyl, halophenyl, lower alkyl-phenyl, ethoxycarbonyl, alkoxyphenyl, N alkoxyalkyl-lower alkyl amino, haloloweralkyl-phenyl or cyclopropyl methyl amino,
-naphtho[1,2-d]thiazol,
-indole, unsubstituted or mono or di substituted independently with lower alkyl,
-benzothiophene,
-benzothiazole, unsubstituted or mono or di substituted independently with lower alkyl or lower alkoxy
-indane,
-naphthalene,
R2 is H, halogen or loweralkyl; and
R3 is -isoquinoline,
amino, or amino mono or disubstituted independently with lower alkyl and lower alkoxy
-4- to 6-membered heterocycloalkyl ring containing from 1 to 2 hetero atoms independently sleeted from O or N, said ring being unsubstituted or mono- or di-substituted independently with lower alkyl, halogen, hydroxy, lower alkoxy, phenyl, lower alkyl phenyl, halolower-alkyl-phenyl, halophenyl, benzoic acid, benzoic acid lower alkyl ester, lower alkyl oxadiazole, phenyl-pyridine, lower alkanoyl, lower alkanoic acid, lower alkanoic acid lower alkyl ester, carbamic acid tert-butyl ester, N-alkyl carbamic acid tert-butyl ester, —CH$_2$-halophenyl, —SO$_2$-phenyl, acetylamino, methyltriazole, —C(O)NSO$_2$—C(CH$_3$)$_3$, benzoic acid benzyl ester, pyridine substituted with C(O)OH, phenyl lower alkanoic acid, phenyl lower alkanoic acid lower alkyl ester, halobenzoic acid, lower alkyl benzoic acid, halobenzoic acid lower alkyl ester, lower alkyl benzoic acid lower alkyl ester, lower alkoxy benzoic acid, lower alkoxy benzoic acid -lower alkyl ester, lower alkoxy phenyl, 2,2-dimethyl-4-oxobutyric acid, 2-oxo-ethyl cyclopentanecarboxylic acid, 3,3-dimethyl-5-oxo-pentanoic acid, carbonyl-cyclohexanecarboxylic acid methyl ester, carbonyl-cyclopropane, (2,4-dioxo-thiazolidin-5-yl)-acetyl, carbonyl-ethyl-(3-hydroxy-isoxazol-5-yl) carbonyl-cyclohexanecarboxylic acid, carbonyl-cyclopentanecarboxylic acid, ethanesulfonylaminocarbonyl-cyclohexanecarbonyl, carbonyl-amino-propionic acid ethyl ester, carboxylic acid tert-butylamide, carboxylic acid ethylamide, carbonyl-amino-acetic acid ethyl ester, or C(O)CH$_2$C(CH$_3$)$_3$, or a pharmaceutically acceptable salt thereof which are active as DGAT inhibitors and therefore find uses in treatment of diseases associated with abnormal metabolism of triglicerides. These diseases include obesity, type II diabetes mellitus and metabolic syndrome.

In another preferred embodiment of the present invention, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term halogens, halo or halides includes all four halogens such as chlorine, bromine, fluorine and iodine.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, bornyl, adamantyl, indenyl and the like. In a preferred embodiment, the "cycloalkyl" moieties can optionally be substituted with one, two, three or four substituents, with the understanding that said substituents are not, in turn, substituted further unless indicated otherwise. Each substituent can independently be, for example, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, azetidine, morpholinyl, thiomorpholinyl, piperazinyl, piperidinyl, pyrrolidinyl, tetrahydropyranyl, tetrahydrofuranyl, 1,3-dioxanyl, thiazolidine-2,4-dione and the like. The heterocycloalkyl groups may be unsubstituted or substituted and attachment may be through their carbon frame or through their heteroatom(s) where appropriate, with the understanding that said substituents are not, in turn, substituted further. In the compound of formula I, wherein R3 is a 4- to 6-membered heterocycloalkyl, the heterocycloalkyl ring preferably contains from 1 to 2 hetero atoms independently sleeted form the group consisting of N and O.

The term "lower alkyl", alone or in combination with other groups, refers to a branched or straight-chain alkyl radical of one to six carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. The term lower alkanoic acid refers to alkanoic acids containing from 2 to 6 carbon atoms such as acetic acid, butyric acid and proprionic acid. The term lower alkanoyl refers to a monovalent lower alkanoic acid produced by removal of the acid hydroxy group such as acetyl The term lower alkoxy groups containing from 1 to 6 carbon atom such as methoxy, ethoxy, and isopropoxy.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like with phenyl being especially preferred.

The alkyl, loweralkyl and aryl groups may be substituted or unsubstituted. When substituted, there will generally be, for example, 1 to 4 substituents present, with the understanding that said substituents are not, in turn, substituted further unless indicated otherwise. These substituents may optionally form a ring with the alkyl, loweralkyl or aryl group to which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyronyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromenyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. In the compound of formula I where R1 is heteroaryl, the heteroaryl ring contains from 1 to 3 hetero atoms independently selected from this group consisting of N, O and Sulfur.

The heteroaryl group described above may be substituted independently with one, two, or three substituents, with the understanding that said substituents are not, in turn, substituted further unless indicated otherwise. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups, with the understanding that said substituents are not, in turn, substituted further unless indicated otherwise.

As used herein, the term "halogen" means a fluorine, chlorine, bromine or iodine radical, preferably a fluorine, chlorine or bromine radical, and more preferably a fluorine or chlorine radical.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermaliy (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

Compounds of the present invention can be prepared from commercially available starting materials or by the use of general synthetic techniques and procedures that are known to those skilled in the art. Outlined below are reaction schemes suitable for the preparation of such compounds. Further exemplification can be found in the specific examples detailed below.

Compounds of the general structure 5 below can be prepared according to the general scheme 1. When X is N, the synthesis of compounds of general structure 5 may be affected by first the coupling of a desirable five or six-member aromatic/heteroaromatic amine or a polycyclic aromatic/heteroaromatic amine or a biaryl amine with the 6-chloronicotinoyl chloride to affect the formation of intermediate 2. Various conditions and methods known to the people skilled in the art may be used to affect this coupling. Most typically intermediate 2 can be obtained by the simple mixing of the desirable amine and 6-chloronicotinoyl chloride in an appropriate solvent in the presence of an organic base (such as triethyl amine, DIEA and the like).

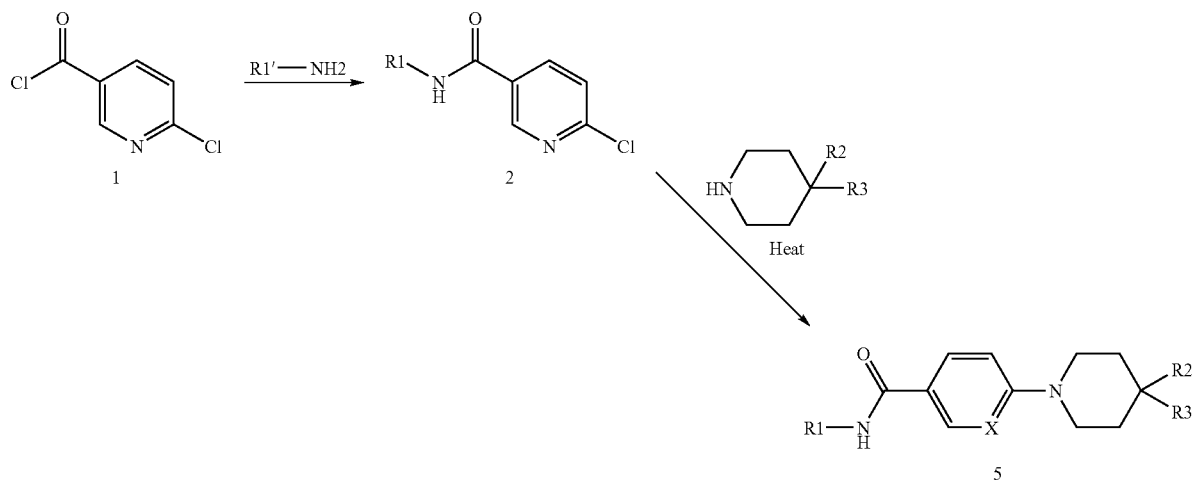

Scheme 1

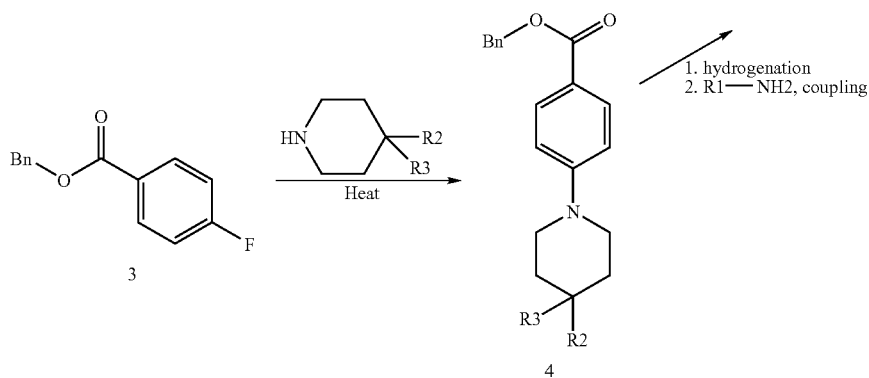

Alternatively, the coupling can be affected by the simple addition of 6-chloronicotinoyl chloride to a sodium, potassium or other appropriate salt of the amine in an appropriate anhydrous solvent. Heating of compounds of the general structure 2 with a desirably 4-substituted piperazine in the presence of a base such as Et₃N or DIEA in an appropriate solvent affords nicotinoyl-piperidine analogs of the general structure 5 (where X=N)

Compounds of the general structure 5 where X=C can be obtained via the coupling of 4-fluorobenzoic acid benzyl ester with an appropriately 4-substituted piperidine to afford intermediates 4. These intermediates can be converted to the corresponding acid by hydrogenolysis and then can be coupled with a desirable arylamine in an appropriate solvent using EDCI and a catalytic amount of DMAP, the BOP reagent or another coupling methodology known to the people skilled in the art.

In compounds of the general structure 5 where R1 is a halogen substituted (preferably Br or I) aryl moiety a biaryl derivative may be prepared via a Suzuki coupling with a desirable aromatic boronate (Miyaura, et. al. Tetrahedron. Lett. 1979, 36, 3437; Belina et. al. Synthesis 2004, 15, 2419). Furthermore, depending on their nature, substitutents R2 and R3 may be amenable to more functionalization under appropriate conditions known to people skilled in the art to afford derivatives. For instance in case where either R2 or R3 is a carboxylic acid ester the ester functionality may be hydrolyzed under appropriate conditions to afford the corresponding acids that may in turn be functionalized further to derivatives under methods and conditions known to the people skilled in the art.

Scheme 2

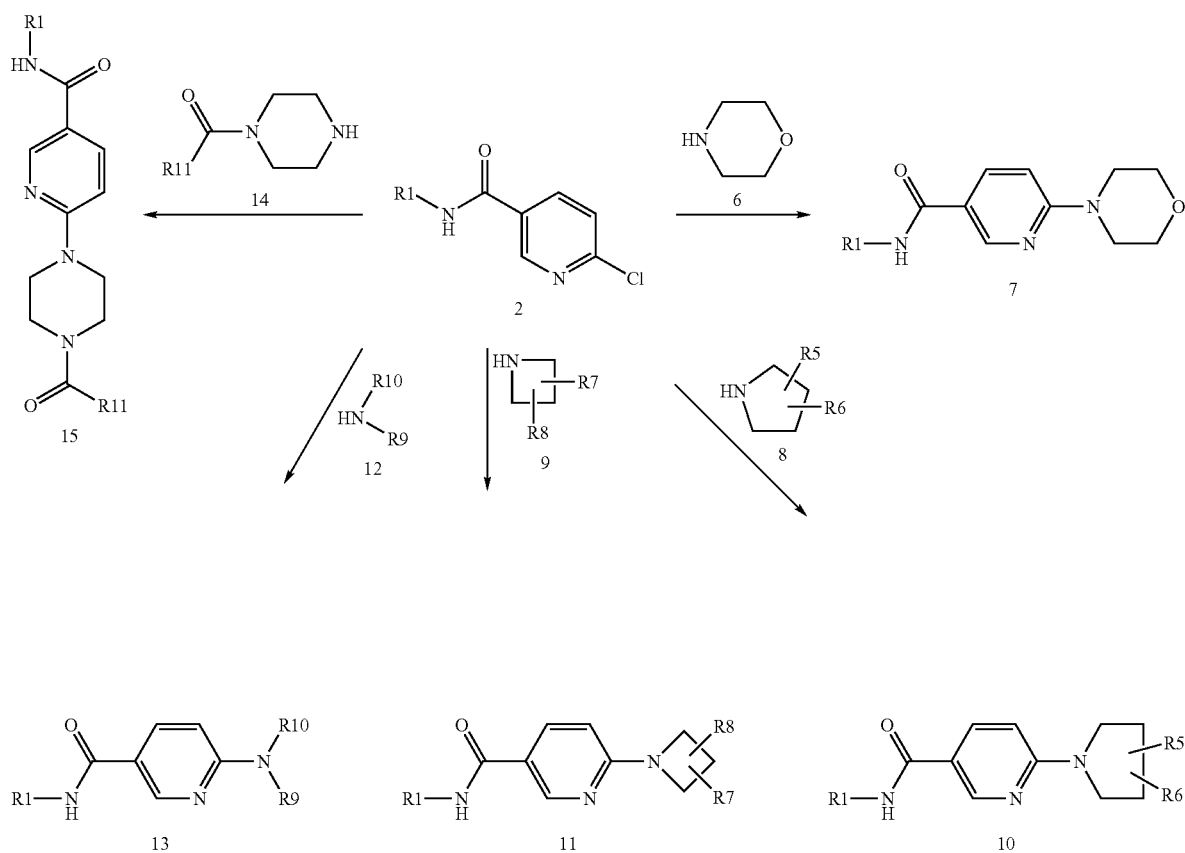

As shown in scheme 2, compounds of the general structure 7 may be prepared by the heating of 6-chloro-nicotinamides of the general structure 2 with morpholine in an appropriate solvent and in the presence of a base as described in scheme 1 above. The pyrrolidine nicotinamides of general structure 10, the azetidine nicotinamides 11, the amine derivatives 13 (where the amine nitrogen does not constitute a member of a ring system) may also be prepared in a similar manner. Also piperazine analogs of the general structure 15 may be prepared in a similar manner from a variety of available piperazines. Depending on their nature, substitutents R5-R11 may be amenable to removal or more functionalization under appropriate conditions known to people skilled in the art to afford derivatives.

Compounds of the general structure 17, may be prepared as shown in scheme 3. 6-chloro-nicotinamides of the general structure 2 may be heated with aryl piperazine esters (preferably ethyl or benzyl esters) of the general structure 16 (where E=C, N) in an appropriate solvent in the presence of a base (triethyl amine, DIEA and the like) to produce the desired compounds 17 (where E=C,N).

Acid derivatives of compounds 17 may be produced by removal of the corresponding ester groups by hydrolysis, hydrogenolysis or any other appropriate method known to the people skilled in the art.

Scheme 3

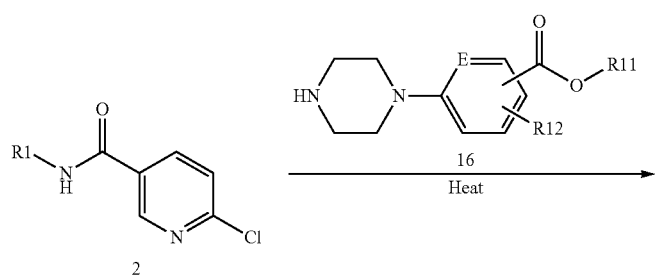

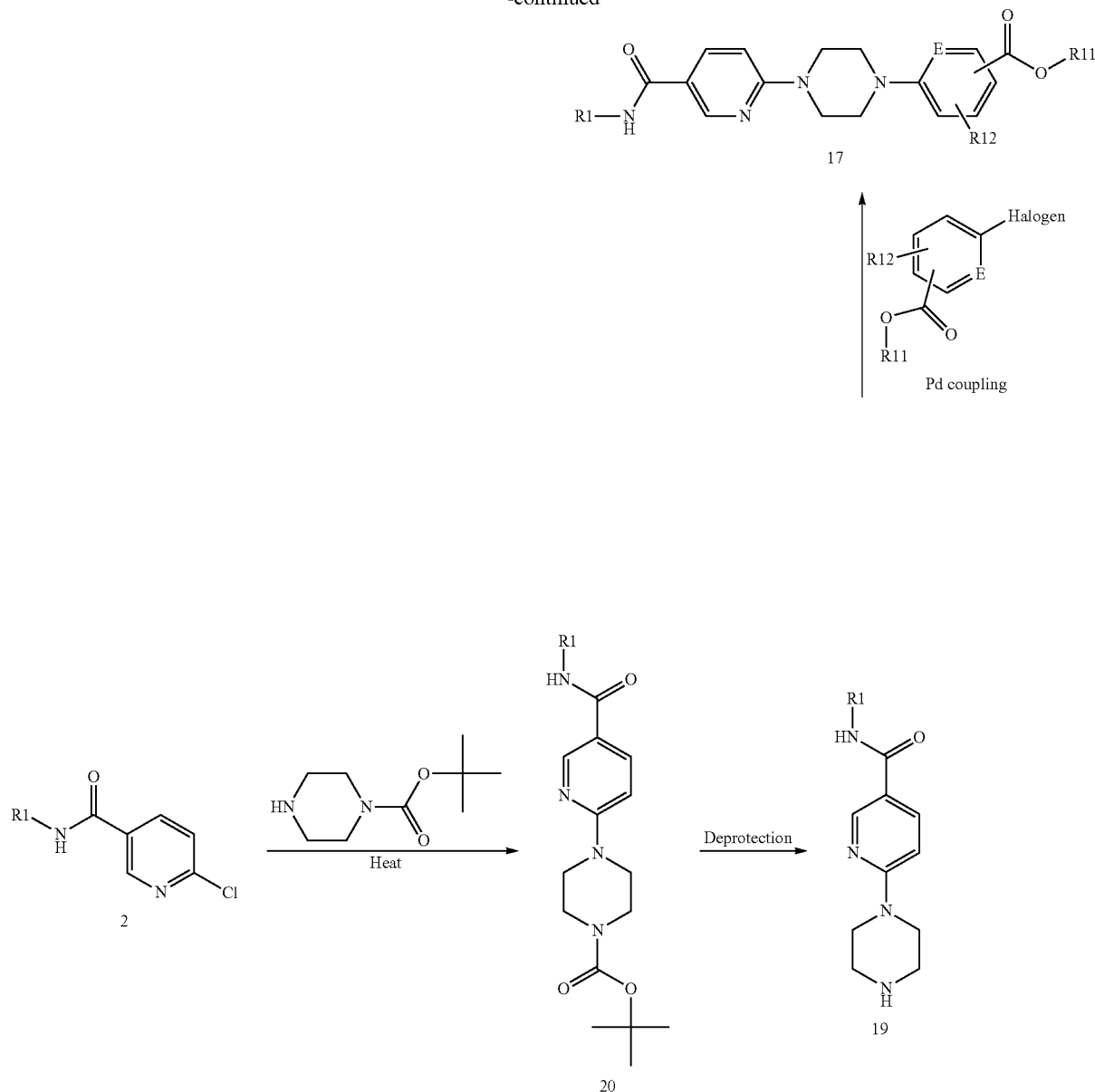

Alternatively, compounds of the general structure 17 (where E=C or N) may be prepared via a Buchwald-type coupling (Buchwald et. al, J. Am. Chem. Soc. 2003, 125, 6653, Buchwald et. al. Buchwald et. al. Metal Catalyzed Cross-Coupling Reactions, $2^{nd}$ Edition, Willey Interscience, 2004) of piperazines of the general structure 19 with appropriately substituted halogen aromatic acids or esters (preferably t-butyl esters) of the general structure 18 (when E=C, halogen may be Br or I; when E=N, halogen may be Cl). Should the coupling product is an ester an acid may be obtained by removal of the ester group under standard methods.

The synthesis of piperazines of the general structure 19 may be affected from 6-chloro-nicotinamides 2 and piperazine-1-carboxylic acid tert-butyl ester after heating in an appropriate solvent in the presence of a base (such as DEA and the like) followed by a deprotection with TFA or other appropriate method known to the people skilled in the art.

piperazines (where Y=N) of general structure 28 may be prepared according to the general scheme 4 from aryl piperazines 26 (where Y=N) by a Buckwald coupling with appropriately substituted halogen aromatic acids or esters (preferably t-butyl esters) of the general structure 18 (when E=C, halogen may be Br or I; when E=N, halogen may be Cl).

Scheme 4

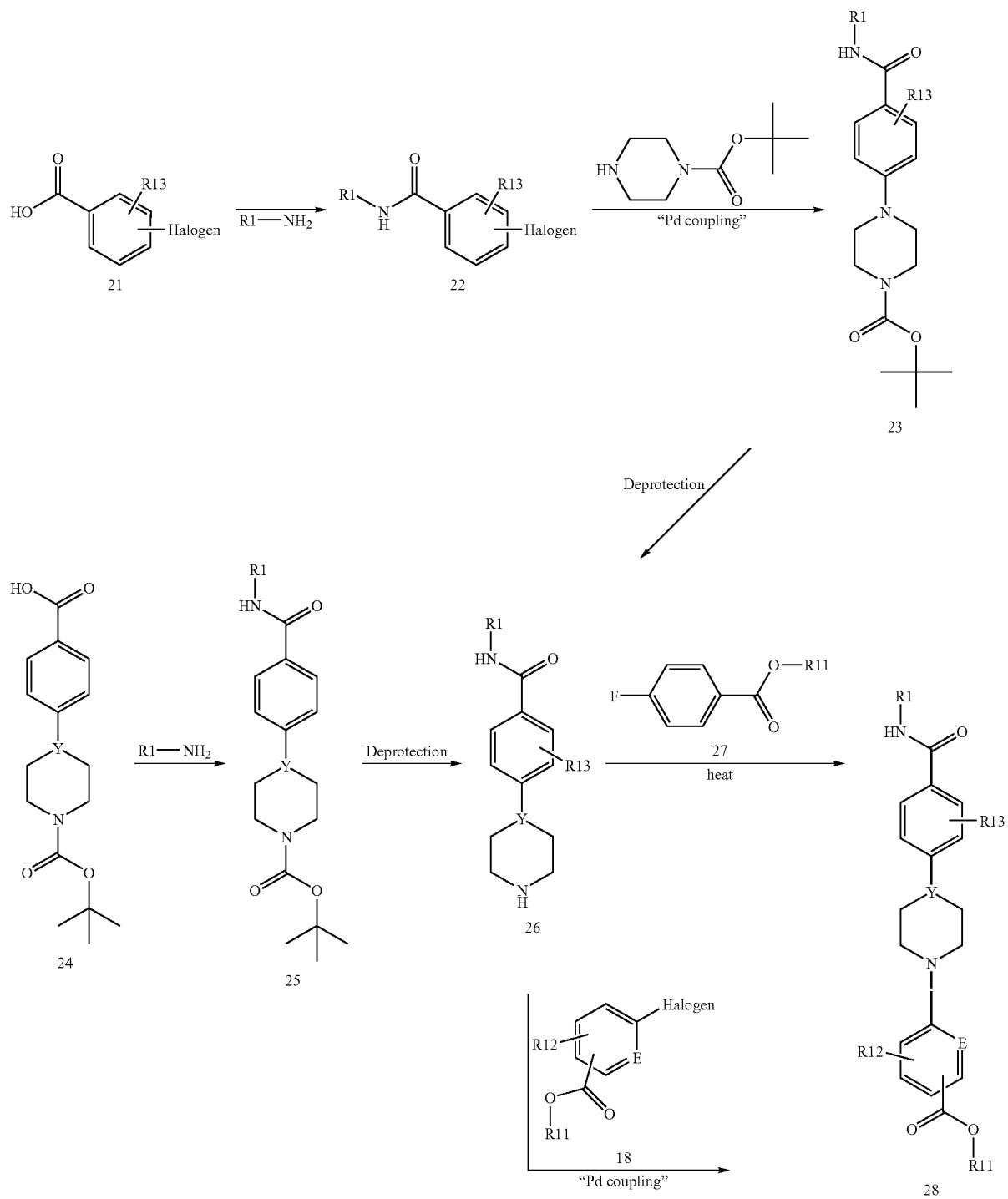

Piperazines (where Y=N) of the type 26 may be prepared by a Buckwald type Pd-coupling of appropriately functionalized halogen-substituted benzoic acid amides of the type 22 with 1-N-Boc-piperazine followed by a removal of the Boc group from the resulting coupling intermediates of the type 23 under standard acidic deprotection conditions with TFA or other suitable method known to the people skilled in the art. The benzoic acid amides of the type 22 may be prepared via the coupling of a desirable aromatic amine with a benzoic acid in the presence of an amide bond forming reagent such as EDCI, BOP and the like. Alternatively amides of the type 22 may be prepared by reaction of a desirable aromatic amine with an appropriate acyl halide under standard conditions.

Simple piperazine analogs of the type 28 (analogs where E=C, R12=H and R13=H) may also be prepared by the aromatic nucleophilic substitution of 4-fluoro benzoic acid esters (preferably ethyl or benzyl esters) with piperazines of type 26 (where Y=N and R13=H) under heat and in the presence of a suitable base such a DIEA.

Piperidines of the general structure 28 (where Y=C and R13=H) may be prepared according to the general scheme 4 from aryl piperidines 26 (where Y=C) by a Buckwald coupling with appropriately substituted halogen aromatic acids using an amide bond forming reagent (such as EDCI, BOP or similar reagent). Starting with piperazines or piperidines of the general structure 19 (X=N, Y=N) and 26 (X=C, Y=N or C) ureas of the general structure 34 (X=N or C, Y=N or C) may be obtained by reaction with desirable isocyanates or carbamoyl chlorides using general methods and conditions known to the people skilled in the art.

Scheme 5

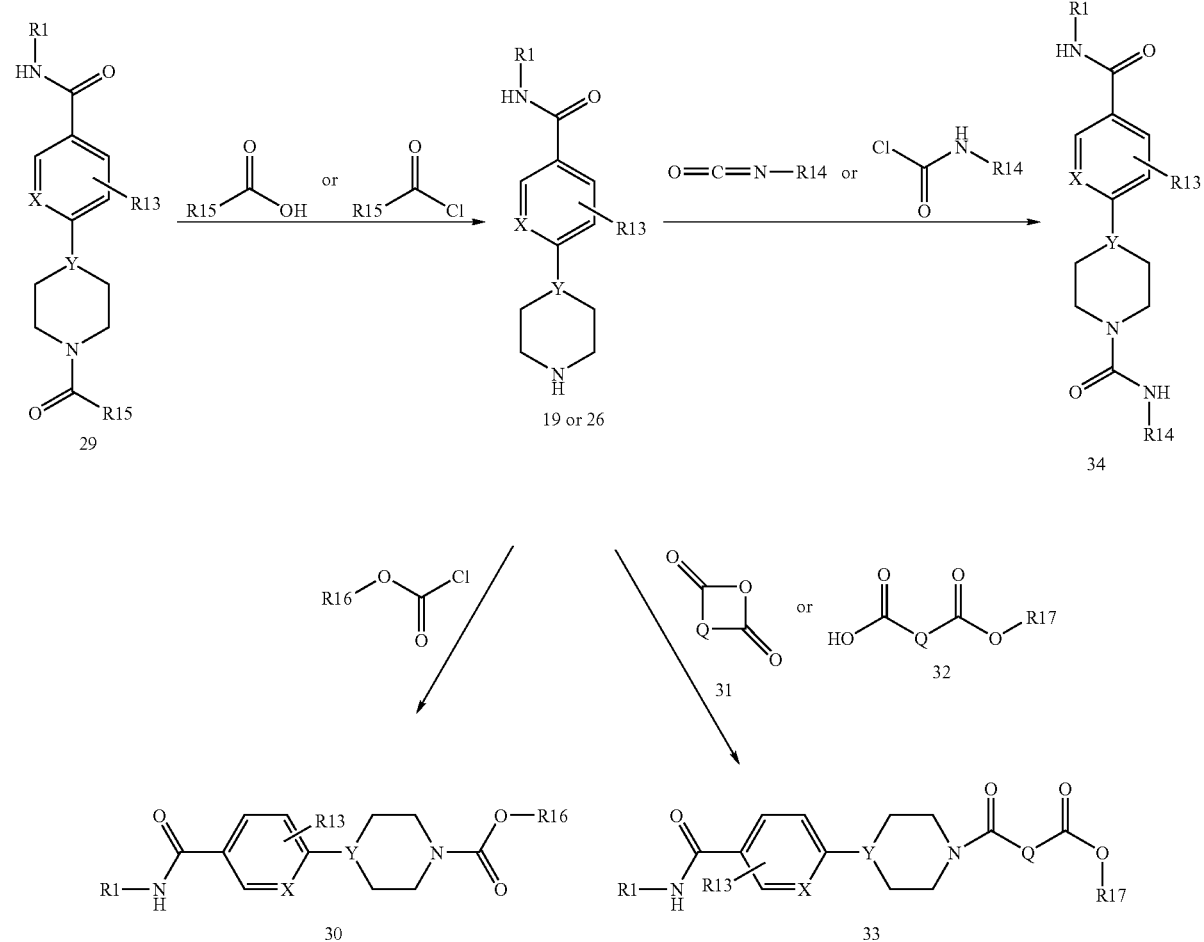

or aromatic esters (preferably t-butyl esters) of the general structure 18 (when E=C, halogen may be Br or I; when E=N, halogen may be Cl).

Piperidines of the type 26 (where Y=C, R13=H) may be prepared form the coupling of commercially available 4-(4-carboxy-phenyl)-piperazine-1-carboxylic acid t-butyl ester 24 (where Y=C) with a desirable aromatic amine using an appropriate amide bond forming method to afford compounds of the type 25 (where Y=C) followed by acid removal of the Boc group with TFA or other suitable method.

As shown in scheme 5 starting with piperazines or piperidines of the general structure 19 (X=N, Y=N) and/or 26 (X=C, Y=N or C) amides of the general structure 29 (X=N or C, Y=N or C) may be prepared by reaction with a desirable acid chloride in the presence of a suitable solvent and a base (such as DIEA, Et₃N and the like). Alternatively compounds of the general structure 29 my be obtained by the reaction of 19 or 26 with a desirable carboxylic acid in a suitable solvent Urethanes of general structure 30, where Y=C or N and X=C or N, may also be obtained from 19 (X=N, Y=N) or 26 (X=C, Y=C or N) by reaction with desirables chloroformate reagents in a suitable solvent in the presence of a base (such as Et₃N, DIEA and the like) under appropriate conditions know to the people skilled in the art.

Compounds of the general structure 33 (where Q is a cyclic or acyclic alkyl group, and R17=H) may be prepared from 19 (X=N, Y=N) or 26 (X=C, Y=C or N) through coupling with an appropriate acid anhydride of the general structure 31 (Q=cyclic or acyclic alkyl group) or a diacid of the general structure 32 (Q=cyclic or acyclic alkyl group, and R17=H) under general methods and conditions known to the people skilled in the art.

Compounds of the general structure 33 (where Q is a cyclic or acyclic alkyl group and R17 is a group such as methyl, ethyl, benzyl and the like) may be prepared from 19 (X=N, Y=N) or 26 (X=C, Y=C or N) through coupling with a desirable appropriate mono ester of the general structure 32 (where Q=cyclic or acyclic alkyl group, and R17 is ethyl, methyl, benzyl or other such group) under general methods and conditions known to the people skilled in the art. From esters of the type 33 (where Q is a cyclic or acyclic alkyl group and R17 is a group such as methyl, ethyl, benzyl and the like) the corresponding acid may be obtained through hydrolysis or hydrogenolysis using conditions known to the people skilled in the art.

EXAMPLES

List of Abbreviations

DGAT is diacylglycerol:acyl CoA O-acyltransferase;
THF is tetrahydrofuran;
DMF is N,N-dimethylformamide;
DMA is N,N-dimethylacetamide;
DMSO is dimethylsulfoxide;
DCM is dichloromethane;
DME is dimethoxyethane;
MeOH is methanol;
EtOH is ethanol;
NaOH is sodium hydroxide;
TFA is trifluoroacetic acid;
HOBT is 1-hydroxybenzotriazole;
DMAP is 4-(dimethylamino)pyridine;
PyBroP is bromotripyrrolidinophosphonium hexafluorophosphate;
BOP is (benzotriazol-1-yloxy)tris(dimethylamino)phosphonium hexafluorophosphate;
EDCl is 1-[3-(dimethylamino)propyl]-3-ethylcarbodlimide hydrochloride;
DIPEA is diisopropylethyl amine;
DEA is diisopropylethyl amine;
Brine is saturated aqueous sodium chloride solution;
DAG is 1,2-dioleoyl-sn-glycerol;
TLC is thin layer chromatography;
RP HPLC is reverse phase high performance liquid chromatography;
APCl-MS is electrospray mass spectrometry;
LCMS is liquid chromatography mass spectrometry;
NMR is nuclear magnetic resonance spectroscopy;
HRMS is high resolution mass spectrometry; and
RT is room or ambient temperature.

Part I

Preparation of Preferred Intermediates

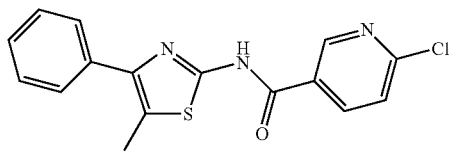

6-chloro-N-(5-methyl-4-phenyl-thiazol-2-yl)-nicotinamide

To a mixture of 5-methyl-4-phenyl-thiazol-2-ylamine (2.0 g, 10.5 mmol) in anhydrous tetrahydrofuran (40 mL) and methylene chloride (40 mL) in a round bottom flask under argon was carefully added sodium hydride (60% in mineral oil, 1.7 g, 42.5 mmol). The mixture was heated in a 60° C. oil bath for one hour, then chilled in an ice bath and 6-chloro-nicotinoyl chloride (2.03 g, 11.6 mmol) was added followed by diisopropylethylamine (7.32 mL, 42.1 mmol). The mixture was heated under argon in an oil bath at 60° C. for two hours and stirred at room temperature overnight. After dilution with methanol, the mixture was loaded onto silica gel and chromatographed using a mixture of ethyl acetate/hexanes to give 6-chloro-N-(5-methyl-4-phenyl-thiazol-2-yl)-nicotinamide (1.0 g, Yield: 29%).

LCMS calcd for C16H12ClN3OS (m/e) 329, obsd 330 (M+H).

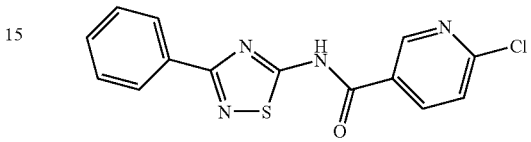

6-chloro-N-(3-phenyl-[1,2,4]thiadiazol-5-yl)-nicotinamide

With a method similar to that used for the preparation of 6-chloro-N-(5-methyl-4-phenyl-thiazol-2-0)-nicotinamide above, 6-chloro-N-(3-phenyl-[1,2,4]thiadiazol-5-yl)-nicotinamide was prepared from 3-phenyl-[1,2,4]thiadiazol-5-ylamine and 6-chloro-nicotinoyl chloride.

LCMS calcd for C14H9ClN4OS (m/e) 316, obsd 317 (M+H).

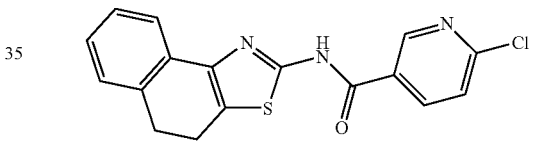

6-chloro-N-(4,5-dihydro-naphtho[1,2-d]thiazol-2-O-nicotinamide

With a method similar to that used for the preparation of 6-chloro-N-(5-methyl-4-phenyl-thiazol-2-yl)-nicotinamide above, 6-chloro-N-(4,5-dihydro-naphtho[1,2-d]thiazol-2-yl)-nicotinamide was prepared from 4,5-dihydro-naphtho[1,2-d]thiazol-2-ylamine and 6-chloro-nicotinoyl chloride.

LCMS calcd for C17H12ClN3OS (m/e) 341, obsd 342 (M+H).

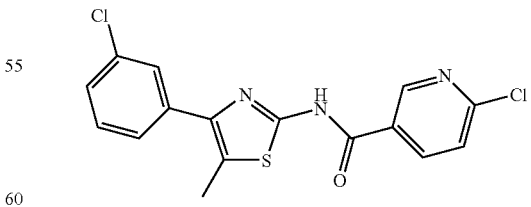

6-chloro-N-[4-(3-chloro-phenyl)-5-methyl-thiazol-2-yl]-nicotinamide

With a method similar to that used for the preparation of 6-chloro-N-(5-methyl-4-phenyl-thiazol-2-yl)-nicotinamide above, 6-chloro-N-[4-(3-chloro-phenyl)-5-methyl-thiazol-2-yl)-nicotinamide was prepared from 4-(3-chloro-phenyl)-5-methyl-thiazo-2-ylamine and 6-chloro-nicotinoyl chloride.

LCMS calcd for C16H11Cl2N3OS (m/e) 363, obsd 364 (M+H).

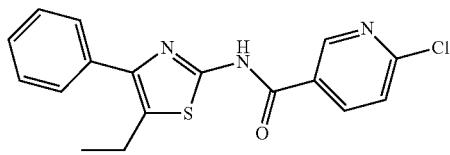

6-chloro-N-(5-ethyl-4-phenyl-thiazol-2-yl)-nicotinamide

With a method similar to that used for the preparation of 6-chloro-N-(5-methyl-4-phenyl-thiazol-2-yl)-nicotinamide above, 6-chloro-N-(5-ethyl-4-phenyl-thiazol-2-yl)-nicotinamide was prepared from 5-ethyl-4-phenyl-thiazol-2-ylamine and 6-chloro-nicotinoyl chloride.

LCMS calcd for C17H14ClN3OS (m/e) 343, obsd 344 (M+H).

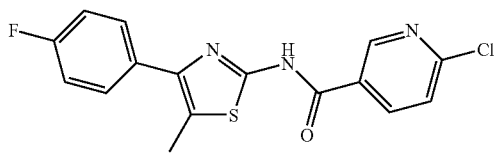

6-chloro-N-[4-(4-fluoro-phenyl)-5-methyl-thiazol-2-yl)-nicotinamide

With a method similar to that used for the preparation of 6-chloro-N-(5-methyl-4-phenyl-thiazol-2-yl)-nicotinamide above, 6-chloro-N-[4-(4-fluoro-phenyl)-5-methyl-thiazol-2-yl)-nicotinamide was prepared from 4-(4-fluoro-phenyl)-5-methyl-thiazol-2-ylamine and 6-chloro-nicotinoyl chloride.

LCMS calcd for C16H11ClFN3OS (m/e) 347, obsd 348 (M+H).

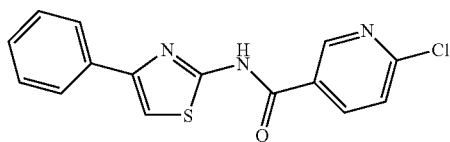

6-chloro-N-(4-phenyl-thiazol-2-yl)-nicotinamide

With a method similar to that used for the preparation of 6-chloro-N-(5-methyl-4-phenyl-thiazol-2-yl)-nicotinamide above, 6-chloro-N-(4-phenyl-thiazol-2-yl)-nicotinamide was prepared from 4-phenyl-thiazol-2-ylamine and 6-chloro-nicotinoyl chloride.

LCMS calcd for C15H10ClN3OS (m/e) 315, obsd 316 (M+H).

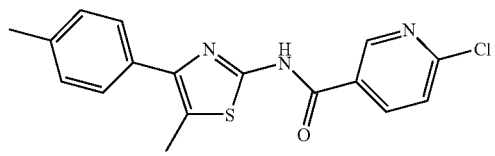

6-chloro-N-(5-methyl-4-p-tolyl-thiazol-2-yl)-nicotinamide

With a method similar to that used for the preparation of 6-chloro-N-(5-methyl-4-phenyl-thiazol-2-yl)-nicotinamide above, 6-chloro-N-(5-methyl-4-p-tolyl-thiazol-2-yl)-nicotinamide was prepared from 5-methyl-4-p-tolyl-thiazol-2-ylamine and 6-chloro-nicotinoyl chloride. LCMS calcd for C17H14ClN3OS (m/e) 343, obsd 344 (M+H).

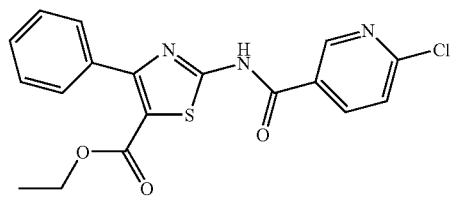

2-[(6-chloro-pyridine-3-carbonyl)-amino]-4-phenyl-thiazole-5-carboxylic acid ethyl ester With a method similar to that used for the preparation of 6-chloro-N-(5-methyl-4-phenyl-thiazol-2-yl)-nicotinamide above, 2-[(6-chloro-pyridine-3-carbonyl)-amino]-4-phenyl-thiazole-5-carboxylic acid ethyl ester was prepared from 2-amino-4-phenyl-thiazole-5-carboxylic acid ethyl ester and 6-chloro-nicotinoyl chloride. LCMS calcd for C18H14ClN3O3S (m/e) 387, obsd 388 (M+H).

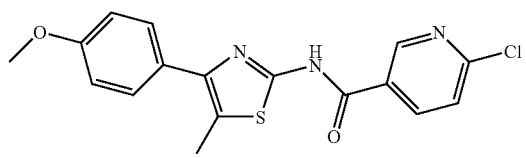

6-chloro-N-[4-(4-methoxy-phenyl)-5-methyl-thiazol-2-yl)-nicotinamide

With a method similar to that used for the preparation of 6-chloro-N-(5-methyl-4-phenyl-thiazol-2-yl)-nicotinamide above, 6-chloro-N-[4-(4-methoxy-phenyl)-5-methyl-thiazol-2-yl]-nicotinamide was prepared from 4-(4-methoxy-phenyl)-5-methyl-thiazol-2-ylamine and 6-chloro-nicotinoyl chloride. LCMS calcd for C17H14ClN3O2S (m/e) 359, obsd 360 (M+H).

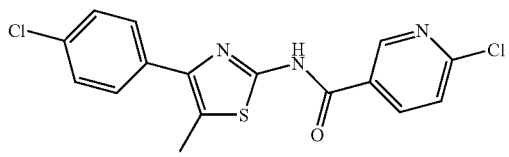

6-chloro-N-[4-(4-chloro-phenyl)-5-methyl-thiazol-2-yl)-nicotinamide

With a method similar to that used for the preparation of 6-chloro-N-(5-methyl-4-phenyl-thiazol-2-yl)-nicotinamide above, 6-chloro-N-[4-(4-chloro-phenyl)-5-methyl-thiazol-2-yl)-nicotinamide was prepared from 4-(4-chloro-phenyl)-5-methyl-thiazol-2-ylamine and 6-chloro-nicotinoyl chloride. LCMS calcd for C16H11Cl2N3OS (m/e) 363, obsd 364 (M+H).

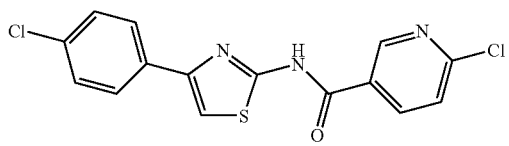

6-chloro-N-[4-(4-chloro-phenyl]-thiazol-2-yl)-nicotinamide

With a method similar to that used for the preparation of 6-chloro-N-(5-methyl-4-phenyl-thiazol-2-yl)-nicotinamide above, 6-chloro-N-[4-(4-chloro-phenyl)-thiazol-2-yl)-nicotinamide was prepared from 4-(4-chloro-phenyl)-thiazol-2-ylamine and 6-chloro-nicotinoyl chloride. LCMS calcd for C15H9Cl2N3OS (m/e) 349, obsd 350 (M+H).

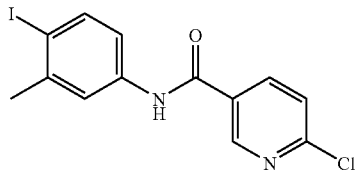

6-Chloro-N-(4-iodo-3-methyl-phenyl)-nicotinamide

A solution of 3-methyl-4-iodoaniline (660 mg 2.84 mmol), diisopropylethyl amine (1.2 mL 8.52 mmol) and a catalytic amount of DMAP in $CH_2Cl_2$ (15 mL) was treated with 6-chloronicotinoyl chloride (500 mg, 2.84 mmol). Upon completion of the reaction, as judged by TLC, the mixture was partitioned between $CH_2Cl_2$ and water. The EtOAc layer was dried over $Na_2SO_4$ filtered and concentrated. The solid residue was washed with hexanes and then was passed through a silica gel plug with 50% EtOAc in hexanes as the elution solvent to afford the product, 6-chloro-N-(4-iodo-3-methyl-phenyl)-nicotinamide. (910 mg, Yield 86%).

HRMS m/z calcd for C13H10N2OICl [M+H]+: 372.9599. Found: 372.9599

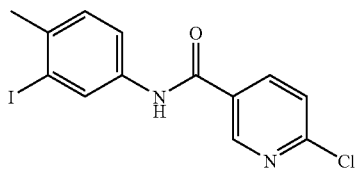

6-Chloro-N-(3-iodo-4-methyl-phenyl)-nicotinamide

Starting with 4-methyl-3-iodoaniline, 6-chloro-N-(3-iodo-4-methyl-phenyl)-nicotinamide was prepared following a procedure similar to the one described in the synthesis of 6-chloro-N-(4-iodo-3-methyl-phenyl)-nicotinamide, above. The product was isolated after a silica gel plug purification with a 0-30% $Et_2O$ in toluene gradient. HRMS m/z calcd for C13H10N2OICl [M+H]+: 372.9599. Found: 372.9599

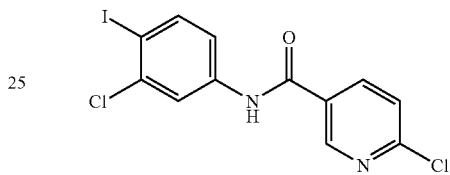

6-Chloro-N-(3-chloro-4-iodo-phenyl)-nicotinamide

Starting with 3-chloro-4-iodo aniline, 6-chloro-N-(3-chloro-4-iodo-phenyl)-nicotinamide was prepared following a procedure similar to the one described in the synthesis of 6-chloro-N-(4-iodo-3-methyl-phenyl)-nicotinamide, above. The product was isolated after a silica gel plug with 30-50% $Et_2O$ in toluene gradient.

1H NMR (300 MHz, chloroform-d), d ppm 7.24 (d, overlapping with chloroform 1H), 7.46 (d, J=9 Hz, 1H), 7.71 (s, 1H), 7.80 (d, J=9 Hz, 1H), 7.87 (s, 1H), 8.14 (d, J=8.4 Hz, 1H), 8.83 (s, 1H)

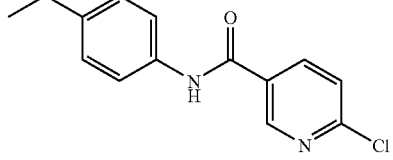

N-(4-tert-Butyl-phenyl)-6-chloro-nicotinamide

Starting with 4-tertbutyl aniline, N-(4-tert-Butyl-phenyl)-6-chloro-nicotinamide was prepared following a procedure similar to the one described in the synthesis of 6-chloro-N-(4-iodo-3-methyl-phenyl)-nicotinamide, above. The product was isolated after a suspension in $CH_2Cl_2$, followed by an addition of excess of hexanes and filtration.

HRMS m/z calcd for C16H17N2OCl [M+H]+: 289.1102. Found: 289.1102

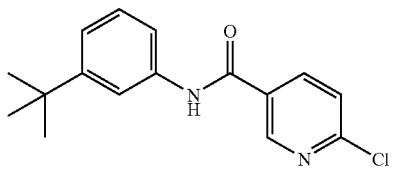

N-(3-tert-Butyl-phenyl)-6-chloro-nicotinamide

Starting with 3-tert-butyl aniline, N-(3-tert-butyl-phenyl)-6-chloro-nicotinamide was prepared following a procedure similar to the one described in the synthesis of 6-chloro-N-(4-iodo-3-methyl-phenyl)-nicotinamide, above. The product was isolated after a silica gel column with 20-30% EtOAc in hexanes gradient. HRMS m/z calcd for C16H17N2OCl [M+H]$^+$: 289.1102. Found: 289.1102.

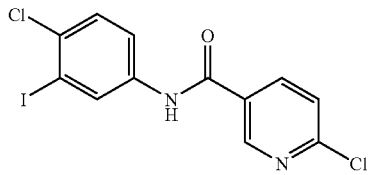

6-Chloro-N-(4-chloro-3-iodo-phenyl)-nicotinamide

6-Chloro-N-(4-chloro-3-iodo-phenyl)-nicotinamide was prepared from 4-chloro-3-iodo aniline (perpared as described in WO03/062241) and 6-chloronicotinoyl chloride following a procedure similar to the one described in the synthesis of 6-chloro-N-(4-iodo-3-methyl-phenyl)-nicotinamide, above. The product was isolated after suspension in small volume of CH$_2$Cl$_2$ and filtration. HRMS m/z calcd for C12H7N2OCl2I [M+H]$^+$: 392.9053. Found: 392.9054.

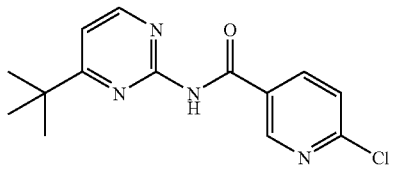

N-(4-tert-Butyl-pyrimidin-2-yl)-6-chloro-nicotinamide

N-(4-tert-Butyl-pyrimidin-2-yl)-6-chloro-nicotinamide was prepared from 4-tert-butyl-pyrimidin-2-ylamine (prepared as described in J. Org. Chem. 1977, 221) and 6-chloronicotinoyl chloride following a procedure similar to the one described in the synthesis of 6-chloro-N-(4-iodo-3-methyl-phenyl)-nicotinamide, above. The product was isolated after silica gel purification with 20-40% EtOAc in hexanes gradient followed by suspension in hexanes and filtration. HRMS m/z calcd for C14H15N4OCl [M+H]$^+$: 291.1007. Found: 291.1007.

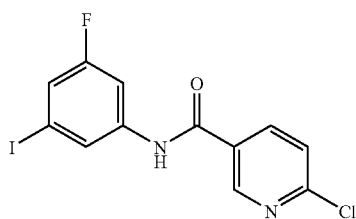

6-Chloro-N-(3-fluoro-5-iodo-phenyl)-nicotinamide

6-Chloro-N-(3-fluoro-5-iodo-phenyl)-nicotinamide was prepared from 3-fluoro-5-iodo aniline and 6-chloronicotinoyl chloride following a procedure similar to the one described in the synthesis of 6-chloro-N-(4-iodo-3-methyl-phenyl)-nicotinamide, above. The product was isolated after suspension in small volume of CH$_2$Cl$_2$, filtration and then a wash with hexanes. HRMS m/z calcd for C12H7N2OClFI [M+H]$^+$: 376.9349. Found: 376.9348

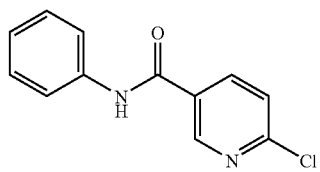

6-Chloro-N-phenyl-nicotinamide

6-Chloro-N-phenyl-nicotinamide was prepared from aniline and 6-chloronicotinoyl chloride following a procedure similar to the one described in the synthesis of 6-chloro-N-(4-iodo-3-methyl-phenyl)-nicotinamide, above. The product was isolated after precipitation out of small volume of CH$_2$Cl$_2$ with hexanes. HRMS m/z calcd for C12H9N2OCl [M+H]$^+$: 233.0476. Found: 233.0476

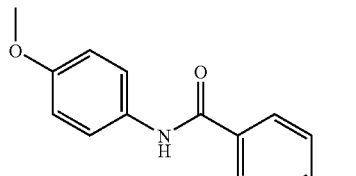

6-Chloro-N-(4-methoxy-phenyl)-nicotinamide

6-Chloro-N-(4-methoxy-phenyl)-nicotinamide was prepared from 4-methoxyaniline and 6-chloronicotinoyl chloride following a procedure similar to the one described in the synthesis of 6-chloro-N-(4-iodo-3-methyl-phenyl)-nicotinamide, above. The product was isolated after precipitation out of small volume of CH$_2$Cl$_2$ with hexanes. HRMS m/z calcd for C13H11N2OCl [M+H]$^+$: 263.0582. Found: 263.0582.

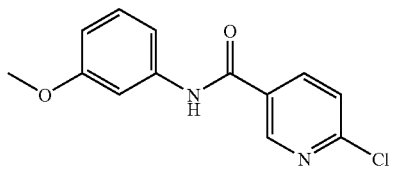

6-Chloro-N-(3-methoxy-phenyl)-nicotinamide

6-Chloro-N-(3-methoxy-phenyl)-nicotinamide was prepared from 3-methoxyaniline and 6-chloronicotinoyl chloride following a procedure similar to the one described in the synthesis of 6-chloro-N-(4-iodo-3-methyl-phenyl)-nicotinamide, above. The product was isolated after precipitation out of small volume of CH$_2$Cl$_2$ with hexanes. HRMS m/z calcd for C13H11N2OCl [M+H]$^+$: 263.0582. Found: 263.0581.

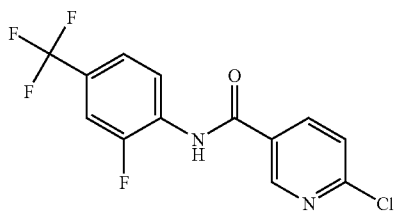

6-Chloro-N-(2-fluoro-4-trifluoromethyl-phenyl)-nicotinamide

6-Chloro-N-(2-fluoro-4-trifluoromethyl-phenyl)-nicotinamide was prepared from 2-fluoro-4-trifluoromethyl aniline and 6-chloronicotinoyl chloride following a procedure similar to the one described in the synthesis of 6-chloro-N-(4-iodo-3-methyl-phenyl)-nicotinamide, above. The product was isolated after precipitation out of a small volume of CH$_2$Cl$_2$ with hexanes. HRMS m/z calcd for C13H7N2OClF4 [M+H]$^+$: 319.0256. Found: 319.0255.

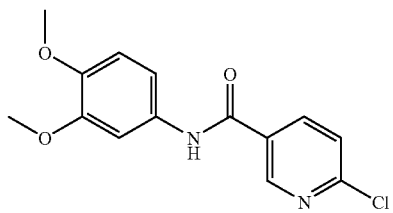

6-Chloro-N-(3,4-dimethoxy-phenyl)-nicotinamide

6-Chloro-N-(3,4-dimethoxy-phenyl)-nicotinamide was prepared from 3,4-dimethoxy aniline and 6-chloronicotinoyl chloride following a procedure similar to the one described in the synthesis of 6-chloro-N-(4-iodo-3-methyl-phenyl)-nicotinamide, above. The product was isolated after precipitation out of a small volume of CH$_2$Cl$_2$ with hexanes. HRMS m/z calcd for C14H13N2O3Cl [M+H]$^+$: 293.0688. Found: 293.0687.

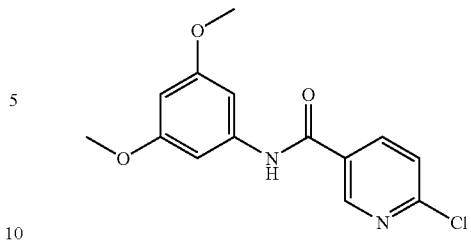

6-Chloro-N-(3,5-dimethoxy-phenyl)-nicotinamide

6-Chloro-N-(3,5-dimethoxy-phenyl)-nicotinamide was prepared from 3,5-dimethoxy aniline and 6-chloronicotinoyl chloride following a procedure similar to the one described in the synthesis of 6-chloro-N-(4-iodo-3-methyl-phenyl)-nicotinamide, above. The product was isolated after precipitation out of a small volume of CH$_2$Cl$_2$ with hexanes. HRMS m/z calcd for C14H13N2O3Cl [M+H]$^+$: 293.0688. Found: 293.0687.

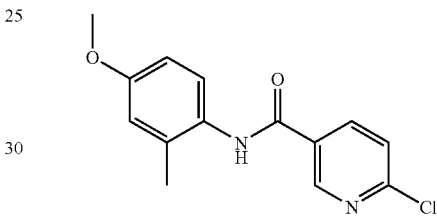

6-Chloro-N-(4-methoxy-2-methyl-phenyl)-nicotinamide

6-Chloro-N-(4-methoxy-2-methyl-phenyl)-nicotinamide was prepared from 4-methoxy-2-methyl aniline and 6-chloronicotinoyl chloride following a procedure similar to the one described in the synthesis of 6-chloro-N-(4-iodo-3-methyl-phenyl)-nicotinamide, above. The product was isolated after precipitation out of a small volume of CH$_2$Cl$_2$ with hexanes. HRMS m/z calcd for C14H13N2O2Cl [M+H]$^+$: 277.0739. Found: 277.0738.

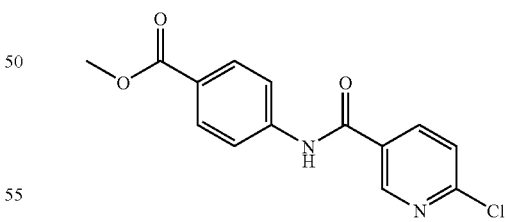

4-[(6-Chloro-pyridine-3-carbonyl)-amino]-benzoic acid methyl ester

4-[(6-Chloro-pyridine-3-carbonyl)-amino]-benzoic acid methyl ester was prepared from 4-amino-benzoic acid methyl ester and 6-chloronicotinoyl chloride following a procedure similar to the one described in the synthesis of 6-chloro-N-(4-iodo-3-methyl-phenyl)-nicotinamide, above. The product was isolated after precipitation out of a small volume of CH$_2$Cl$_2$ with hexanes. HRMS m/z calcd for C14H11N2O3Cl [M+H]$^+$: 291.0531. Found: 291.0530.

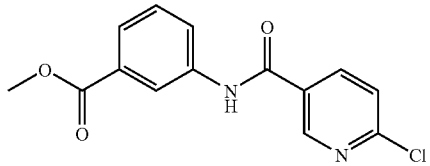

3-[(6-Chloro-pyridine-3-carbonyl)-amino]-benzoic acid methyl ester

3-[(6-Chloro-pyridine-3-carbonyl)-amino]-benzoic acid methyl ester was prepared from 3-amino-benzoic acid methyl ester and 6-chloronicotinoyl chloride following a procedure similar to the one described in the synthesis of 6-chloro-N-(4-iodo-3-methyl-phenyl)-nicotinamide, above. The product was isolated after precipitation out of a small volume of CH$_2$Cl$_2$ with hexanes. HRMS m/z calcd for C14H11N2O3Cl [M+H]$^+$: 291.0531. Found: 291.0531.

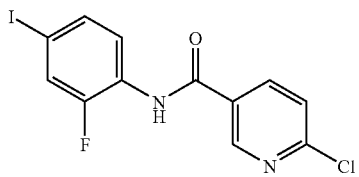

6-Chloro-N-(2-fluoro-4-iodo-phenyl)-nicotinamide

6-Chloro-N-(2-fluoro-4-iodo-phenyl)-nicotinamide was prepared from 2-fluoro-4-iodo aniline and 6-chloronicotinoyl chloride following a procedure similar to the one described in the synthesis of 6-chloro-N-(4-iodo-3-methyl-phenyl)-nicotinamide, above. The product was isolated after precipitation out of a small volume of CH$_2$Cl$_2$ with hexanes. HRMS m/z calcd for C12H7N2OFClI [M+H]$^+$: 376.9349. Found: 376.9349.

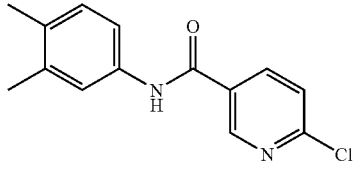

6-Chloro-N-(3,4-dimethyl-phenyl)-nicotinamide

6-Chloro-N-(3,4-dimethyl-phenyl)-nicotinamide was prepared from 3,4-dimethyl aniline and 6-chloronicotinoyl chloride following a procedure similar to the one described in the synthesis of 6-chloro-N-(4-iodo-3-methyl-phenyl)-nicotinamide, above. The product was isolated after precipitation out of a small volume of CH$_2$Cl$_2$ with hexanes. HRMS m/z calcd for C14H13N2OCl [M+H]$^+$: 261.0789. Found: 261.0788

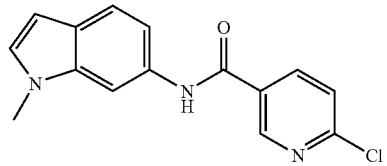

6-Chloro-N-(1-methyl-1H-indol-6-yl)-nicotinamide

6-Chloro-N-(1-methyl-1H-indol-6-yl)-nicotinamide was prepared from 1-methyl-1H-indol-5-ylamine (prepared as described in J. Med. Chem. 2007, 5509) and 6-chloronicotinoyl chloride in a manner similar to the one described in the synthesis of 6-chloro-N-(4-iodo-3-methyl-phenyl)-nicotinamide, above. The product was isolated after purification with a silica gel column and 0.0-30% EtOAc in hexanes gradient. H1 NMR (300 MHz, chloroform-d) d ppm 3.79 (s, 3H), 6.44 (d, J=3.0 Hz, 1H), 6.94 (dd, J=10.2, 8.4 Hz 1H), 7.04 (d, J=3.0, 1H), 7.43 (d, J=8.4 Hz, 1H), 7.55 (d, J=8.4 Hz, 1H), 7.89 (s, 1H), 8.05 (s, 1H), 8.16 (dd, J=10.2, 8.4 Hz, 1H), 8.87 (apparent s, 1H)

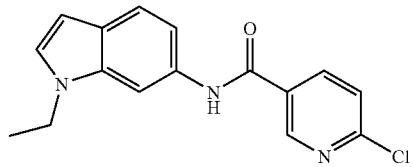

6-Chloro-N-(1-ethyl-1H-indol-6-yl)-nicotinamide

6-Chloro-N-(1-ethyl-1H-indol-6-yl)-nicotinamide was prepared from 1-ethyl-1H-indol-5-ylamine (prepared as described in J. Med. Chem. 2007, 5509), and 6-chloronicotincyl chloride in a procedure similar to the one described in the synthesis of 6-chloro-N-(4-Iodo-3-methyl-phenyl)-nicotinamide, above. LCMS calcd for C16H14ClN3O (m/e) 299, obsd 300 (M+H).

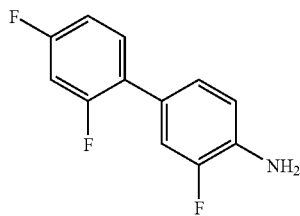

3,2',4'-Trifluoro-biphenyl-4-ylamine

To a solution of 4-bromo-2-fluoro-phenylamine (190 mg, 1 mmol) and 2,4-difluorophenylboronic acid (240 mg, 1 mmol) in 2.5 ml of 1,2-dimethoxy-ethane was added tetrakis(triphenylphosphine)palladium(0) (110 mg, 0.1 mmol) and 0.5 ml of 2M sodium carbonate aqueous solution. The mixture was microwaved at 150° C. for 15 min. The solvents were evaporated and the residue was diluted with CH$_2$Cl$_2$ and filtered. The filtration was concentrated and purified on a flash chromatography column with 0-80% EtOAc/hexanes to give 3,2', 4'-trifluoro-biphenyl-4-ylamine as an off-white solid (200 mg, 90%). LRMS calcd for C12H8F3N (m/e) 223, obsd 224 (M+H).

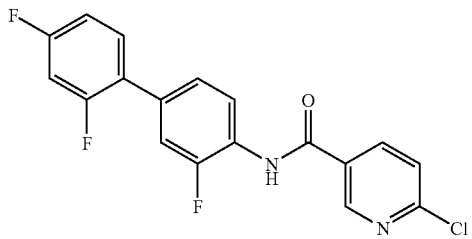

6-Chloro-N-(3,2',4'-trifluoro-biphenyl-4-yl)-nicotinamide

6-Chloro-N-(3,2',4'-trifluoro-biphenyl-4-yl)-nicotinamide was prepared from 3,2',4'-trifluoro-biphenyl-4-yl amine and 6-chloronicotinoyl chloride following a procedure similar to the one described in the synthesis of 6-chloro-N-(4-iodo-3-methyl-phenyl)-nicotinamide, above. The product was isolated after a silica gel column chromatography with 0-30% EtOAc in hexanes. H1 NMR (300 MHz, chloroform-d) d ppm 6.91 (m, 2H), 7.15 (apparent t, J=8.1 Hz, 1H), 7.24-7.1 (m, 3H), 7.95 (dd, J=10.5 8.1 Hz, 2H), 8.69 (d, J=2.1 Hz, 2H).

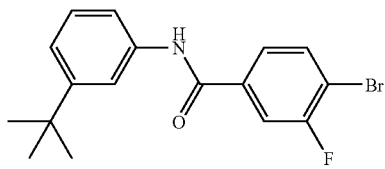

4-Bromo-N-(3-tert-butyl-phenyl)-3-fluoro-benzamide

To 3-tert-butyl-phenylamine was added 4-bromo-3-fluoro-benzoic acid, DMF (21 mL) and EDCI and were stirred at room temperature overnight. The reaction was diluted with DCM (8 mL) and was washed with HCl (1 M, 8 mL), NaOH (1 M, 8 mL), and brine (5 mL), dried over Na2SO4, and concentrated by stream of nitrogen. The resulting viscous oil was purified by flash chromatography with increasing concentration ethyl acetate in hexanes to afford the product. LCMS calcd for C17H17FNO (m/e) 349, obsd 350 (M+H).

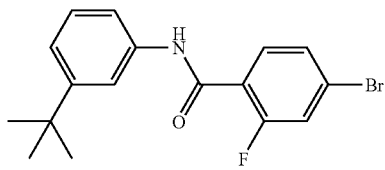

4-Bromo-N-(3-tert-butyl-phenyl)-2-fluoro-benzamide

4-Bromo-N-(3-tert-butyl-phenyl)-2-fluoro-benzamide was synthesized from 3-tert-butyl-phenylamine and 4-bromo-2-fluoro-benzoic acid in a manner similar to the one described in the synthesis of 4-bromo-N-(3-tert-butyl-phenyl)-3-fluoro-benzamide above. LCMS calcd for C17H17FNO (m/e) 349, obsd 350 (M+H).

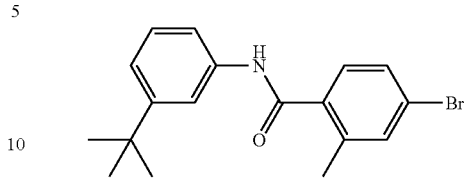

4-Bromo-N-(3-tert-butyl-phenyl)-2-fluoro-benzamide

4-Bromo-N-(3-tert-butyl-phenyl)-2-methyl-benzamide was synthesized from 3-tert-butyl-phenylamine and 4-bromo-2-methyl-benzoic acid in a manner similar to the one described in the synthesis of 4-bromo-N-(3-tert-butyl-phenyl)-3-fluoro-benzamide above. LCMS calcd for C18H20BrNO (m/e) 345, obsd 346 (M+H).

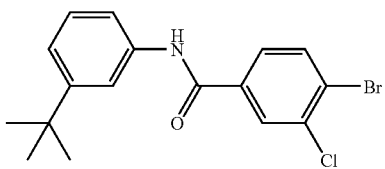

4-Bromo-N-(3-tert-butyl-phenyl)-3-chloro-benzamide

4-Bromo-N-(3-tert-butyl-phenyl)-3-chloro-benzamide was synthesized from 3-tert-butyl-phenylamine and 4-bromo-3-chloro-benzoic acid in a manner similar to the one described in the synthesis of 4-bromo-N-(3-tert-butyl-phenyl)-3-fluoro-benzamide above. LCMS calcd for C17H17BrClNO (m/e) 367, obsd 368 (M+H).

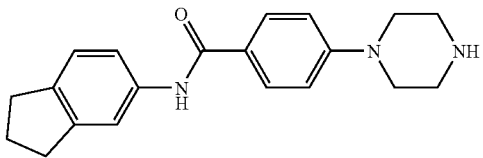

N-Indan-5-yl-4-piperazin-1-yl-benzamide

To a mixture of 4-(4-carboxy-phenyl)-piperazine-1-carboxylic acid tert-butyl ester (918 mg, 3 mmol) and 5-aminoindan (399 mg, 3 mmol) in methylene chloride (30 mL) was added EDCI (580 mg, 3 mmol) and DMAP (20 mg, 0.16 mmol). The mixture was stirred at room temperature overnight and then extracted with methylene chloride (50 mL) and aqueous hydrochloric acid (1N, 20 mL). The organic layer was washed with water, then sodium hydroxide solution and finally with water and brine. The solution was dried over sodium sulfate and filtered. Solvents were evaporated and the residue was crystallized from ethyl acetate (40 mL) to give 4-[4-(indan-5-ylcarbamoyl)-phenyl]-piperazine-1-carboxylic acid tert-butyl ester. This intermediate was dissolved in methylene chloride (5 mL) and trifluoroacetic acid (3 mL). The mixture was stirred at room temperature for 1 hr and solvents were evaporated. The residue was extracted with methylene chloride and 1N sodium hydroxide solution. The organic layer was washed with brine and dried over sodium sulfate. The product, N-indan-5-yl-4-piperazin-1-yl-benzamide was obtained after solvent evaporation (450 mg, Yield: 47%). LCMS calc for C20H23N3O (m/e) 321.42, obsd 322.5 (M+H).

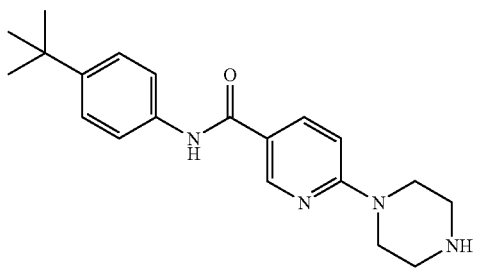

N-(4-tert-Butyl-phenyl)-6-piperazin-1-yl-nicotinamide

4-[5-(4-tert-Butyl-phenylcarbamoyl)-pyridin-2-yl]-piperazine-1-carboxylic acid tert-butyl ester (200 mg, 0.45 mmol) was dissolved at rt in a mixture of 30% TFA in CH$_2$Cl$_2$. The reaction mixture was stirred until TLC indicated consumption of starting material (30 min). The mixture was then partitioned between EtOAc and water. The water layer was basified with solid NaOH to pH 12. The organic layer was separated and the aqueous layer was extracted again with EtOAc. The combined organic layer was washed with water, dried over Na$_2$SO$_4$, filtered and concentrated to afford the product (89 mg, Yield: 56%). HRMS m/z calcd for C20H26N4O [M+H]$^+$: 339.2180. Found: 339.2180.

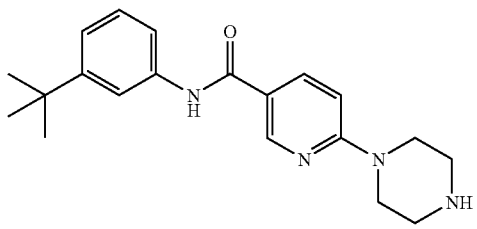

N-(3-tert-Butyl-phenyl)-6-piperazin-1-yl-nicotinamide

N-(3-tert-Butyl-phenyl)-6-piperazin-1-yl-nicotinamide was prepared from 4-[5-(3-tert-butyl-phenylcarbamoyl)-pyridin-2-yl]-piperazine-1-carboxylic acid tert-butyl ester in a manner similar to the one described in the synthesis of N-(4-tert-butyl-phenyl)-6-piperazin-1-yl-nicotinamide above. HRMS m/z calcd for C20H26N4O [M+H]$^+$: 339.2179. Found: 339.2180.

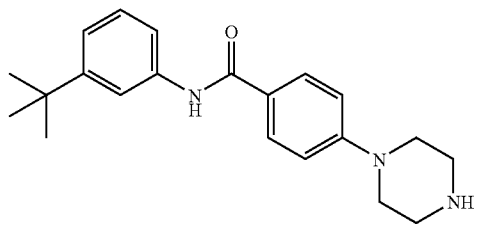

N-(3-tert-Butyl-phenyl)-4-piperazin-1-O-benzamide

N-(3-tert-Butyl-phenyl)-4-piperazin-1-yl-benzamide was prepared from 4-[4-(3-tert-butyl-phenylcarbamoyl)-phenyl]-piperazine-1-carboxylic acid tert-butyl ester in a manner similar to the one described in the synthesis of N-(4-tert-butyl-phenyl)-6-piperazin-1-yl-nicotinamide above. HRMS m/z calcd for C21H27N3O [M+H]$^+$: 338.2225. Found: 338.2227.

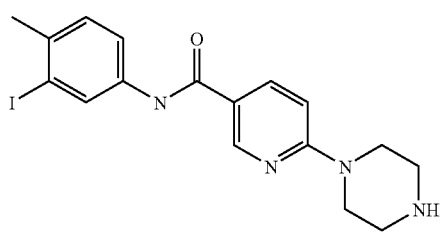

N-(3-Iodo-4-methyl-phenyl)-6-piperazin-1-yl-nicotinamide

N-(3-Iodo-4-methyl-phenyl)-6-piperazin-1-yl-nicotinamide was prepared by the TFA deprotection of 4-[5-(3-iodo-4-methyl-phenylcarbamoyl)-pyridin-2-yl]-piperazine-1-carboxylic acid tert-butyl ester in a manner similar to the one described in the synthesis of N-(4-tert-butyl-phenyl)-6-piperazin-1-yl-nicotinamide above. LCMS calcd for C17H19IN4O (m/e) 422, obsd 423 (M+H).

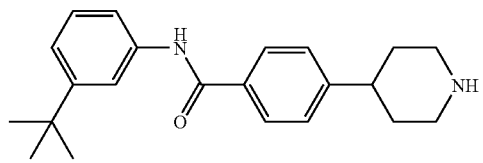

N-(3-tert-Butyl-phenyl)-4-piperidin-4-O-benzamide

N-(3-tert-Butyl-phenyl)-4-piperidin-4-yl-benzamide was synthesized by the TFA deprotection of 4-[4-(3-tert-butyl-phenylcarbamoyl)-phenyl]-piperidine-1-carboxylic acid tert-butyl ester in a manner similar to the one described in the synthesis of N-(4-tert-butyl-phenyl)-6-piperazin-1-yl-nicotinamide. LCMS calcd for C22H28N2O (m/e) 336, obsd 337 (M+H).

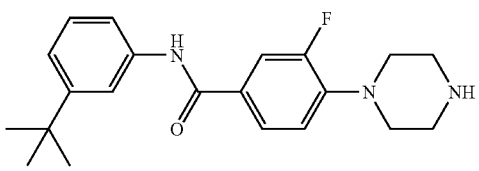

N-(3-tert-Butyl-phenyl)-3-fluoro-4-piperazin-1-yl-benzamide

The 4-bromo-N-(3-tert-butyl-phenyl)-3-fluoro-benzamide (0.15 mmol) was added piperazine-1-carboxylic acid tert-butyl ester (0.195 mmol), NaOtBu (0.375 mmol), XantPhos (0.03 mmol), Pd$_2$ dba$_2$ (0.009 mmol) and 1,4 dioxane (0.2 mL). The reaction vial was purged with Ar, sealed, and heated at 85° C. overnight. The reaction was worked up by diluting with ethyl acetate (mL) washed with NH$_4$Cl (1.5 M, 4 mL), and brine (4 mL), filtered through a plug of Na$_2$SO$_4$, and dried under a stream of nitrogen. To the intermediate was added DCM (1 ml) and TFA (0.2 mL) and stirred at room temperature for 1 hr. The reaction was diluted ethyl acetate (mL) washed with NaHCO$_3$ (saturated, 4 mL, twice), and brine (4 mL), filtered through a plug of Na$_2$SO$_4$ and dried under a stream of nitrogen yielding the product, N-(3-tert-butyl-phenyl)-3-fluoro-4-piperazin-1-yl-benzamide. LCMS calcd for C21H26FN3O (m/e) 355, obsd 356 (M+H).

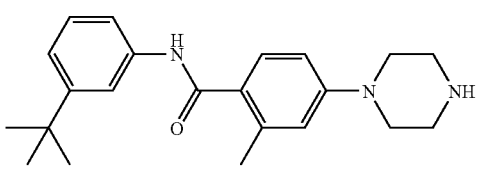

N-(3-tent-Butyl-phenyl)-2-fluoro-4-piperazin-1-O-benzamide

N-(3-tert-Butyl-phenyl)-2-fluoro-4-piperazin-1-yl-benzamide was synthesized from 4-bromo-N-(3-tert-butyl-phenyl)-2-fluoro-benzamide and piperazine-1-carboxylic acid tert-butyl ester in a manner similar to the one described in the synthesis of N-(3-tert-butyl-phenyl)-3-fluoro-4-piperazin-1-yl-benzamide above. LCMS calcd for C21H26FN3O (m/e) 355, obsd 356 (M+H).

N-(3-tert-Butyl-phenyl)-2-methyl-4-piperazin-1-O-benzamide

N-(3-tert-Butyl-phenyl)-2-methyl-4-piperazin-1-yl-benzamide was synthesized from 4-bromo-N-(3-tert-butyl-phenyl)-2-methyl-benzamide and piperazine-1-carboxylic acid tert-butyl ester in a manner similar to the one described in the synthesis of N-(3-tert-butyl-phenyl)-3-fluoro-4-piperazin-1-yl-benzamide above. LCMS calcd for C22H29N3O (m/e) 351, obsd 352 (M+H).

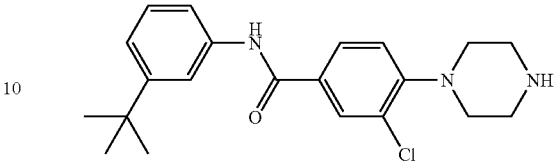

N-(3-tert-Butyl-phenyl)-3-chloro-4-piperazin-1-yl-benzamide

N-(3-tert-Butyl-phenyl)-3-chloro-4-piperazin-1-yl-benzamide was synthesized from 4-bromo-N-(3-tert-butyl-phenyl)-3-chloro-benzamide and piperazine-1-carboxylic acid tert-butyl ester in a manner similar to the one described in the synthesis of N-(3-tert-butyl-phenyl)-3-fluoro-4-piperazin-1-yl-benzamide above. LCMS calcd for C21H26ClN3O (m/e) 371, obsd 372 (M+H)

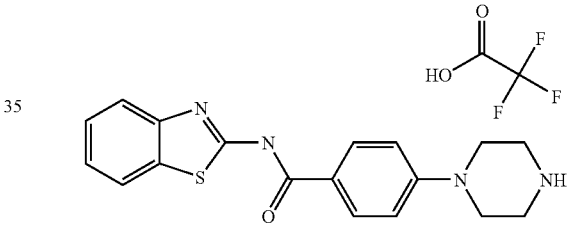

N-Benzothiazol-2-O-4-piperazin-1-O-benzamide trifluoroacetate

To a mixture of 4-(4-carboxy-phenyl)-piperazine-1-carboxylic acid tert-butyl ester (250 mg, 0.82 mmol) and 2-aminothiazole (125 mg, 0.83 mmol) in DMF (20 mL) was added EDCl (184 mg, 0.96 mmol) and DMAP (100 mg, 0.83 mmol). The mixture was stirred at room temperature overnight and then heated to 100° C. for 5 hrs. Solvents were evaporated and the residue was extracted with ethyl acetate and ammonium chloride solutions. The residue was crystallized from methanol (40 mL) to afford the intermediate 4-[4-(benzothiazol-2-ylcarbamoyl)-phenyl]-piperazine-1-carboxylic acid tert-butyl ester. LCMS calc for C$_{23}$H$_{26}$N$_4$O$_3$S (m/e) 438.17, obsd 439.2 (M+H).

The above intermediate was then suspended in methylene chloride (3 mL) and treated with trifluoroacetic acid (1 mL). The mixture was stirred at room temperature for 1 hr and then the solvents were evaporated. The residue was dried, triturated with ether and filtered to afford N-benzothiazol-2-yl-4-piperazin-1-yl-benzamide trifluoroacetate (130 mg) MS calc for C$_{18}$H$_{18}$N$_4$OS (m/e) 338., obsd 339. (M+H)

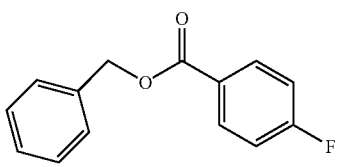

4-Fluoro-benzoic acid benzyl ester

A mixture of 4-fluorobenzoic acid (1.0 g, 7.13 mmol) in Et₂O was treated with oxallyl chloride (760 mL, 8.55 mmol) and a catalytic amount of DMF. The mixture was then stirred until the evolution of gas stopped. The mixture was then filtered and concentrated under reduced pressure. The residue was dissolved in a small volume of CH₂Cl₂ and the solution was added in a drop wise manner to a mixture of benzyl alcohol (770 mg, 7.13 mmol), diisopropyl ethyl amine (2.49 mL, 14.3 mmol) and a catalytic amount of DMAP in CH₂Cl₂ (20 mL). After stirring overnight the reaction mixture was concentrated and the residue was passed through a silica gel plug with 10% Et₂O in hexanes to afford the product (991 mg, Yield: 60%). FIRMS m/z calcd for C14H11O2F [M+H]⁺: 230.0743. Found: 230.0742.

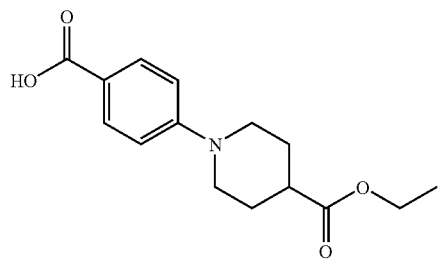

1-(4-Carboxy-phenyl)-piperidine-4-carboxylic acid ethyl ester

A solution of 4-fluoro-benzoic acid benzyl ester (720 mg, 3.13 mmol) in dioxane (10 mL) was treated with diisopropyl ethyl amine (1.64 mL, 9.39 mmol), ethyl isonipecotate (1.54 g, 9.39 mmol), a catalytic amount of DMAP and heated in a sealed tube at 120° C. for approximately 18 h. The mixture was then cooled, followed addition of another portion of ethyl isonipecotate (1.54 g, 9.39 mmol) and the mixture was reheated at 120° C. After stirring for one more day the mixture was cooled, another portion of ethyl isonipecotate (1.54 g, 9.39 mmol) was added and the mixture was heated again at 120° C. and stirred for an additional 3 day period. The mixture was then cooled and partitioned between EtOAc and water. The EtOAc layer was collected, dried over Na₂SO₄, filtered and concentrated and the residue was chromatographed with a silica gel column and 0-50% Et₂O in hexanes gradient. The intermediate isolated from this operation was dissolved in EtOH (15 mL). Followed addition of 10% Pd/C (15 mg) and the mixture was hydrogenated under one atmosphere of hydrogen for 3.5 h. Followed filtration, the solids were washed with EtOH and the combined organic layer was evaporated to afford the product (200 mg, Yield 10%). HRMS m/z calcd for C15H19NO4 [M+H]⁺: 278.1387. Found: 278.1387.

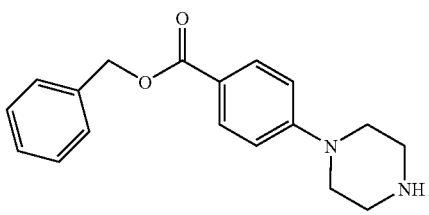

4-piperazin-1-yl-benzoic acid benzyl ester

A mixture of 4-fluorobenzoic acid (5.0 g, 36 mmol) in CH₂Cl₂ was treated with oxallyl chloride (6.2 mL, 72 mmol) and a catalytic amount of DMF. The mixture was stirred until the evolution of gas stopped and then concentrated under reduced pressure. The residue was re-dissolved in CH₂Cl₂ and the solution was added in a drop wise manner to a mixture of benzyl alcohol (3.9 g, 36 mmol), diisopropyl ethyl amine (12.6 mL, 72 mmol) and a catalytic amount of DMAP in CH₂Cl₂. After stirring overnight the reaction mixture was concentrated and the residue was passed through a silica gel plug with 10% Et₂O in hexanes. The intermediate 4-fluoro benzoic acid benzyl ester obtained from the above procedure was dissolved in DMSO (25 mL). Followed addition of piperazine (14 g, and the mixture was heated in a sealed tube at 120° C. overnight. Next morning the reaction mixture was partitioned between EtOAc and water. The water layer was basified to pH 12 with solid NaOH, extracted once again with EtOAc and the combined EtOAc layer was dried over Na₂SO₄, filtered and concentrated to afford the product (8.5 g, Yield: 80%). HRMS m/z calcd for C18H20N2O2 [M+H]: 297.1598. Found: 297.1597.

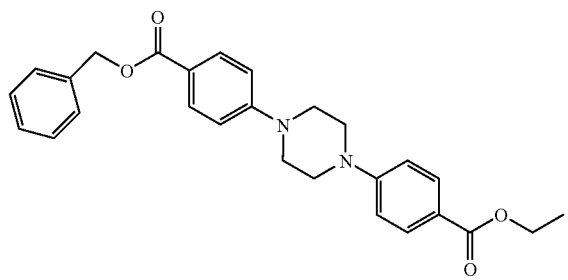

4-Benzylbenzoate-piperidine-4-ethyl benzoate

A mixture of 4-piperazin-1-yl-benzoic acid benzyl ester (500 mg, 1.68 mmol), 4-fluoro benzoic acid ethyl ester (1.4 g, 8.4 mmol), diisopropylethyl amine (1.47 mL, 8.4 mmol) and a catalytic amount of DMAP in DMSO (6 mL) was stirred at 130° C. in a sealed tube for 70 h. The mixture was the cooled partitioned between EtOAc and water. The EtOAc layer was collected, dried over Na₂SO₄, filtered and concentrated. The residue was suspended in hexanes and the suspension was then filtered. The solid obtained passed through a plug of silica gel using 0-100% EtOAc in hexanes to afford the product (480 mg, Yield; 64%). HRMS m/z calcd for C27H28N2O4 [M+H]⁺: 445.2122; Found: 445.2120.

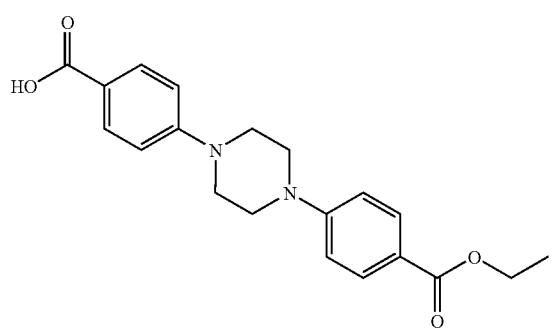

4-Ethylbenzoate-piperidine-4-benzoic acid

A mixture of 4-benzylbenzoate-piperidine-4-ethyl benzoate (200 mg, 0.45 mmol) 10% Pd/C (48 mg) in EtOH/EtOAc (1:1) was hydrogenated under 1 atm of hydrogen for 2 h. Then followed addition of additional portion of 10% Pd/C (100 mg) and the mixture was hydrogenated again under 1 atm of hydrogen for 5 h more. Followed filtration, the solids were washed with THF and DMF. The combined filtrate was concentrated to afford the product (130 mg, Yield: 82%).

HRMS m/z calcd for C20H22N2O4 [M+H]$^+$: 355.1653. Found: 355.652.

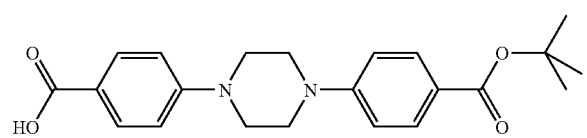

4-[4-(4-carboxyphenyl)-piperazin-1-yl]-benzoic acid tent-butyl ester

To a degassed mixture of 4-(piperazin-1-yl)-benzoic acid ethyl ester (1.45 g, 6.2 mmol), 4-bromobenzoic acid tert-butyl ester (1.75 g, 6.8 mmol), cesium carbonate (3.9 g, 12 mmol) in dioxane (25 mL) was added tris(dibenzylideneacetone)dipalladium (300 mg, 5 mol %) and 2-(dicyclohexylphosphino)-2',4',6'-tris(isopropyl)-biphenyl (x-phos, 300 mg, 10 mol %). The mixture was heated in a sealed tube with stirring at 100° C. for 3 hrs. Solvents were evaporated and the residue was extracted with ethyl acetate and water, The organic layer was dried over sodium sulfate and solvents were evaporated. The crude material was purified through a flash column chromatography using ethyl acetate and hexanes to give the intermediate 4-[4-(4-ethoxycarbonylphenyl)-piperazin-1-yl]-benzoic acid tert-butyl ester as solid (1.3 g, 51% yield)

The above intermediate, (1.2 g, 2.68 mmol) was suspended in methanol (100 mL) and THF (100 mL) and sodium hydroxide solution (1N, 80 mL) was added. The mixture was refluxed for 2 hrs and then concentrated. The mixture was acidified with 1N HCl and the solid formed was filtered to give 4-[4-(4-carboxyphenyl)-piperazin-1-yl]-benzoic acid tert-butyl ester (1.1 g). LCMS calcd for C22H26N2O4 (m/e) 382. Obsd: 381 (M−H$^+$)

Part II

Preparation of Preferred Compounds of the Invention

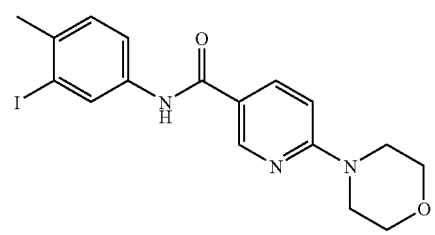

Example 1

N-(3-Iodo-4-methyl-phenyl)-6-morpholin-4-yl-nicotinamide

A mixture of 6-chloro-N-(3-iodo-4-methyl-phenyl)-nicotinamide (50 mg, 0.13 mmol) and morpholine (35 mg, 0.42 mmol), diisopropylethyl amine (0.07 mL, 0.42 mmol) and a catalytic amount of DMAP in dioxane (5 mL) was heated at 120° C. in a sealed tube until consumption of the limiting reagent. The mixture was then cooled and partitioned between EtOAc and water. Organic layer was removed, dried over Na$_2$SO$_4$ filtered and concentrated to a residue that after a silica gel column with 20-40% EtOAc in hexanes gradient afforded the product. HRMS m/z calcd for C17H18N3O2I [M+H]$^+$: 424.0517. Found: 424.0516.

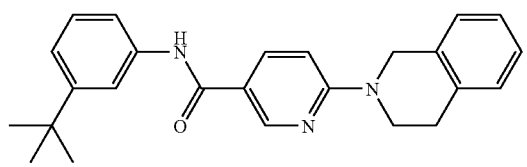

Example 2

N-(3-tert-Butyl-phenyl)-6-(3,4-dihydro-1H-isoquinolin-2-yl)-nicotinamide

N-(3-tert-Butyl-phenyl)-6-(3,4-dihydro-1H-isoquinolin-2-yl)-nicotinamide was synthesized from N-(3-tert-butylphenyl)-6-chloro-nicotinamide and 1,2,3,4-tetrahydro-isoquinoline in a method similar to the one described in the synthesis of N-(3-iodo-4-methyl-phenyl)-6-morpholin-4-yl-nicotinamide above. LCMS calcd for C25H27N3O (m/e) 385, obsd 386 (M+H).

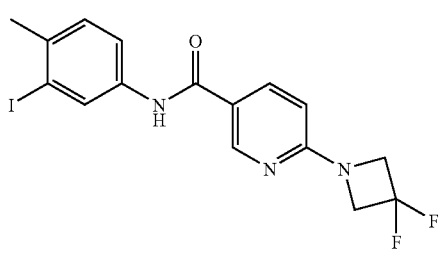

Example 3

6-(3,3-Difluoro-azetidin-1-yl)-N-(3-iodo-4-methyl-phenyl)-nicotinamide 6-(3,3-Difluoro-azetidin-1-yl)-N-(3-iodo-4-methyl-phenyl)-nicotinamide was prepared from 6-chloro-N-(3-iodo-4-methyl-phenyl)-nicotinamide and 3,3-difluoroazetidine hydrochloride in a manner similar to the one described in the synthesis of N-(3-Iodo-4-methyl-phenyl)-6-morpholin-4-yl-nicotinamide above. The product was isolated after silica gel column purification with 20-30% EtOAc in hexanes to afford the product (23 mg. Yield: 40%). HRMS m/z calcd for C16H14N3OFI [M+H]+: 430.0223. Found: 430.0224.

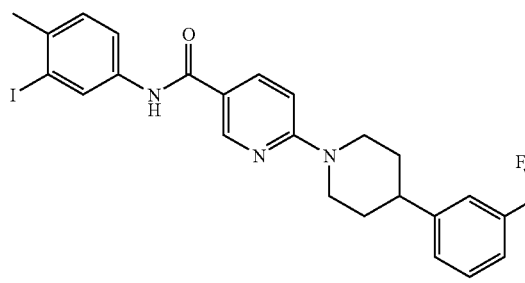

Example 4

4-(3-Trifluoromethyl-phenyl)-3,4,5,6-tetrahydro-2H-[1,2']bipyridinyl-5'-carboxylic acid (3-iodo-4-methyl-phenyl)-amide 4-(3-Trifluoromethyl-phenyl)-3,4,5,6-tetrahydro-2H-[1,2']bipyridinyl-5'-carboxylic acid (3-iodo-4-methyl-phenyl)-amide was prepared from 6-chloro-N-(3-iodo-4-methyl-phenyl)-nicotinamide and 4-(3 trifluoromethyl-phenyl) piperidine hydrochloride in a manner similar to the one described in the synthesis of N-(3-iodo-4-methyl-phenyl)-6-morpholin-4-yl-nicotinamide above. The product was isolated after silica gel column purification with 20-40% EtOAc in hexanes. HRMS m/z calcd for C25H23N3OF3I [M+H]+: 566.0911. Found: 566.0910. START

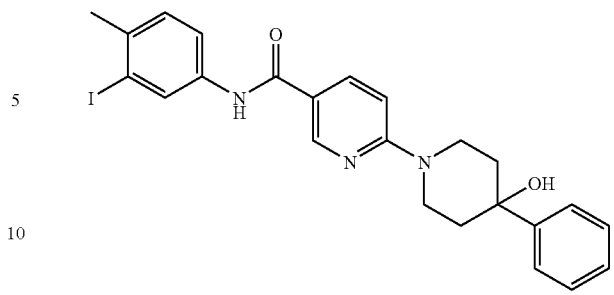

Example 5

4-Hydroxy-4-phenyl-3,4,5,6-tetrahydro-2H-[1,2']bipyridinyl-5'-carboxylic acid (3-iodo-4-methyl-phenyl)-amide A solution of 6-chloro-N-(3-iodo-4-methyl-phenyl)-nicotinamide (100 mg, 0.26 mmol), a catalytic amount of DMAP, diisopropylethyl amine (0.14 mL, 8.1 mmol), 4-hydroxy-4-phenyl piperidine (140 mg, 8.1 mmol) in 5 mL in dioxane was heated at 95° C. in a sealed tube for about 48 h. The reaction mixture was then cooled and partitioned between EtOAc and aq. saturated Na2CO3. The organic layer was then collected, dried over Na2SO4 filtered and concentrated. The residue was chromatographed with a silica gel column and 20-100% EtOAc in hexanes to afford the product (90 mg. Yield: 65%). HRMS m/z calcd for C24H24N3O2I [M+H]+: 514.0986. Found: 514.0987.

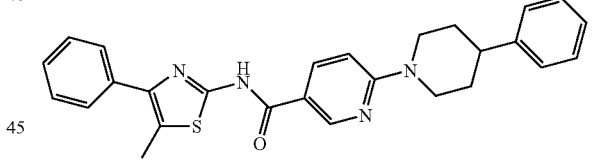

Example 6

4-(3-trifluoromethyl-phenyl)-3,4,5,6-tetrahydro-2H-[1,2']bipyridinyl-5'-carboxylic acid (5-methyl-4-phenyl-thiazol-2-yl)-amide To a mixture of 6-chloro-N-(5-methyl-4-phenyl-thiazol-2-yl)-nicotinamide (50 mg, 0.152 mmol) and anhydrous N-methylpyrrolidinone (10 mL) in a sealed tube was added 4-(3-trifluoromethyl-phenyl)-piperidine hydrochloride (80 mg, 0.30 mmol) followed by diisopropylethylamine (0.11 mL, 0.63 mmol). The mixture was heated in an oil bath at 70° C. overnight. After concentration, the crude was purified by RP-HPLC to give 4-(3-trifluoromethyl-phenyl)-3,4,5,6-tetrahydro-2H-[1,2']bipyridinyl-5'-carboxylic acid (5-methyl-4-phenyl-thiazol-2-yl)-amide as an off-white powder. LCMS calcd for C28H25F3N4OS (m/e) 522, obsd 523 (M+H).

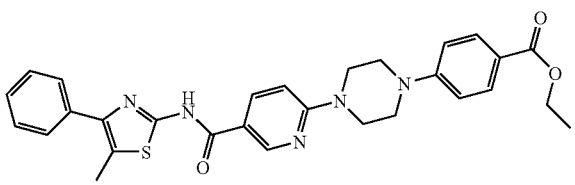

Example 7

Preparation of 4-{4-[5-(5-methyl-4-phenyl-thiazol-2-ylcarbamoyl)-pyridin-2-yl]-piperazin-1-yl}-benzoic acid ethyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-{4-[5-(5-methyl-4-phenyl-thiazol-2-ylcarbamoyl)-pyridin-2-yl]-piperazin-1-yl}-benzoic acid ethyl ester was prepared from 6-chloro-N-(5-methyl-4-phenyl-thiazol-2-yl)-nicotinamide and 4-piperazin-1-yl-benzoic acid ethyl ester. LCMS calcd for C29H29N5O3S (m/e) 527, obsd 528 (M+H).

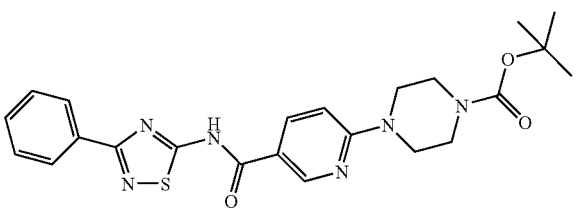

Example 8

4-[5-(3-phenyl-[1,2,4]thiadiazol-5-ylcarbamoyl)-pyridin-2-yl]-piperazine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-[5-(3-phenyl-[1,2,4]thiadiazol-5-ylcarbamoyl)-pyridin-2-yl]-piperazine-1-carboxylic acid tert-butyl ester was prepared from 6-chloro-N-(3-phenyl-[1,2,4]thiadiazol-5-yl)-nicotinamide and piperazine-1-carboxylic acid tert-butyl ester. LCMS calcd for C23H26N6O3S (m/e) 466, obsd 467 (M+H).

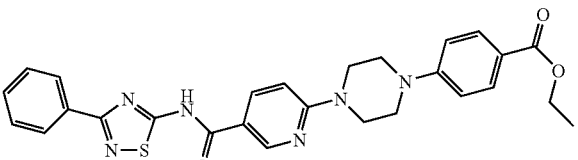

Example 9

4-{4-[5-(3-phenyl-[1,2,4]thiadiazol-5-ylcarbamoyl)-pyridin-2-yl]-piperazin-1-yl}-benzoic acid ethyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-{4-[5-(3-phenyl-[1,2,4]thiadiazol-5-ylcarbamoyl)-pyridin-2-yl]-piperazin-1-yl}-benzoic acid ethyl ester was prepared from 6-chloro-N-(3-phenyl-[1,2,4]thiadiazol-5-yl)-nicotinamide and 4-piperazin-1-yl-benzoic acid ethyl ester. LCMS calcd for C27H26N6O3S (m/e) 514, obsd 515 (M+H).

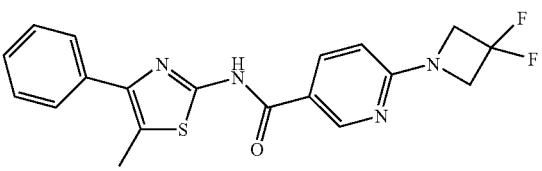

Example 10

6-(3,3-difluoro-azetidin-1-yl)-N-5-methyl-4-phenyl-thiazol-2-yl)-nicotinamide

With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 6-(3,3-difluoro-azetidin-1-yl)-N-5-methyl-4-phenyl-thiazol-2-yl)-nicotinamide was prepared from 6-chloro-N-(5-methyl-4-phenyl-thiazol-2-yl)-nicotinamide and 3,3-difluoro-azetidine. LCMS calcd for C19H16F2N4OS (m/e) 386, obsd 387 (M+H).

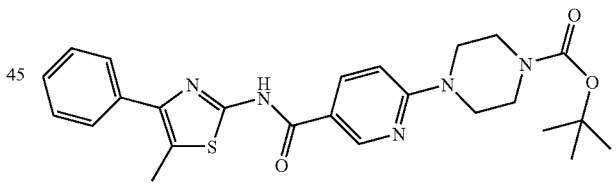

Example 11

4-[5-(5-methyl-4-phenyl-thiazol-2-ylcarbamoyl)-pyridin-2-yl]-piperazine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-[5-(5-methyl-4-phenyl-thiazol-2-ylcarbamoyl)-pyridin-2-yl]-piperazine-1-carboxylic acid tert-butyl ester was prepared from 6-chloro-N-(5-methyl-4-phenyl-thiazol-2-yl)-nicotinamide and piperazine-1-carboxylic acid tert-butyl ester. LCMS calcd for C25H29N5O3S (m/e) 479, obsd 480 (M+H).

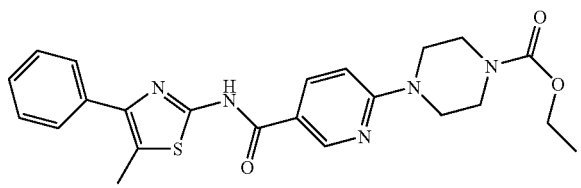

Example 12

4-[5-(5-methyl-4-phenyl-thiazol-2-ylcarbamoyl)-pyridin-2-yl]-piperazine-1-carboxylic acid ethyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-[5-(5-methyl-4-phenyl-thiazol-2-ylcarbamoyl)-pyridin-2-yl]-piperazine-1-carboxylic acid ethyl ester was prepared from 6-chloro-N-(5-methyl-4-phenyl-thiazol-2-yl)-nicotinamide and piperazine-1-carboxylic acid ethyl ester. LCMS calcd for C23H25N5O3S (m/e) 451, obsd 452 (M+H).

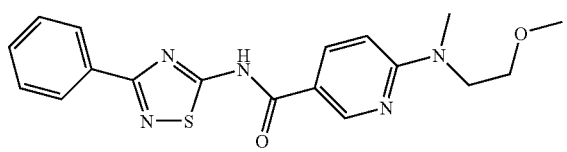

Example 13

6-[(2-methoxy-ethyl)-methyl-amino]-N-(3-phenyl-[1,2,4]thiadiazol-5-yl)-nicotinamide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 6-[(2-methoxy-ethyl)-methyl-amino]-N-(3-phenyl-[1,2,4]thiadiazol-5-yl)-nicotinamide was prepared from 6-chloro-N-(3-phenyl-[1,2,4]thiadiazol-5-yl)-nicotinamide and (2-methyoxy-ethyl)-methyl-amine. LCMS calcd for C18H19N5O2S (m/e) 369, obsd 370 (M+H).

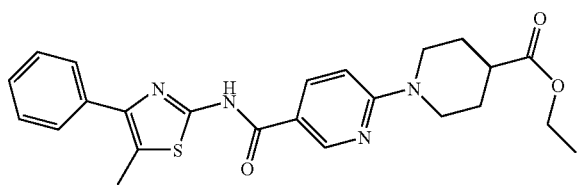

Example 14

5'-(5-methyl-4-phenyl-thiazol-2-ylcarbamoyl)-3,4,5,6-tetrahydro-2H-[1,2']pyridinyl-4-carboxylic acid ethyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 5'-(5-methyl-4-phenyl-thiazol-2-ylcarbamoyl)-3,4,5,6-tetrahydro-2H-[1,2']bipyridinyl-4-carboxylic acid ethyl ester was prepared from 6-chloro-N-(5-methyl-4-phenyl-thiazol-2-yl)-nicotinamide and piperidine-4-carboxylic acid ethyl ester. LCMS calcd for C24H26N4O3S (m/e) 450, obsd 451 (M+H).

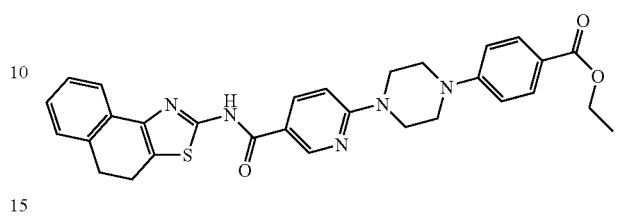

Example 15

4-{4-[5-(4,5-dihydro-naphtho[1,2-d]thiazol-2-ylcarbamoyl)-pyridin-2-yl]-piperazin-1-yl}-benzoic acid ethyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-{4-[5-(4,5-dihydro-naphtho[1,2-d]thiazol-2-ylcarbamoyl)-pyridin-2-yl]-piperazin-1-yl}-benzoic acid ethyl ester was prepared from 6-chloro-N-(4,5-dihydro-naphtho[1,2-d]thiazol-2-yl)-nicotinamide and 4-piperazin-1-yl-benzoic acid ethyl ester. LCMS calcd for C30H29N5O3S (m/e) 539, obsd 540 (M+H).

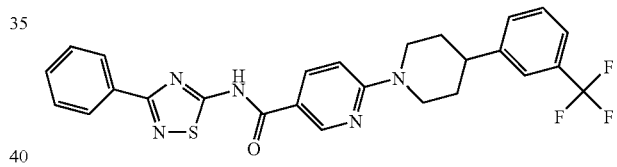

Example 16

4-(3-trifluoromethyl-phenyl)-3,4,5,6-tetrahydro-2H-[1,2']bipyridinyl-5'-carboxylic acid (3-phenyl-[1,2,4]thiadiazol-5-yl)-amide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-(3-trifluoromethyl-phenyl)-3,4,5,6-tetrahydro-2H-[1,2']bipyridinyl-5'-carboxylic acid (3-phenyl-[1,2,4]thiadiazol-5-yl)-amide was prepared from 6-chloro-N-(3-phenyl-[1,2,4]thiadiazol-5-yl)-nicotinamide and 4-(3-trifluoromethyl-phenyl)-piperidine. LCMS calcd for C26H22F3N5OS (m/e) 509, obsd 510 (M+H).

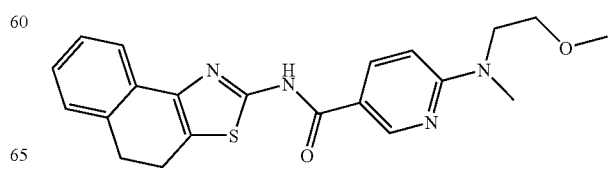

Example 17

Preparation of N-(4,5-dihydro-naphtho[1,2-d]thiazol-2-yl)-6-[(2-methoxy-ethyl)-methyl-amino]-nicotinamide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, N-(4,5-dihydro-naphtho[1,2-d]thiazol-2-yl)-6-[(2-methoxy-ethyl)-methyl-amino]-nicotinamide was prepared from 6-chloro-N-(4,5-dihydro-naphtho[1,2-d]thiazol-2-yl)-nicotinamide and (2-methyoxy-ethyl)-methyl-amine. LCMS calcd for C21H22N4O2S (m/e) 394, obsd 395 (M+H).

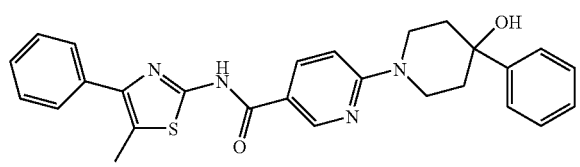

Example 18

4-Hydroxy-4-phenyl-3,4,5,6-tetrahydro-2H-[1,2']bipyridinyl-5% carboxylic acid (5-methyl-4-phenyl-thiazol-2-yl)-amide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-hydroxy-4-phenyl-3,4,5,6-tetrahydro-2H-[1,2']bipyridinyl-5'-carboxylic acid (5-methyl-4-phenyl-thiazol-2-yl)-amide was prepared from 6-chloro-N-(5-methyl-4-phenyl-thiazol-2-yl)-nicotinamide and 4-phenyl-piperidin-4-ol. LCMS calcd for C27H26N4O2S (m/e) 470, obsd 471 (M+H).

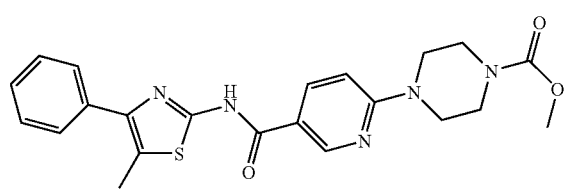

Example 19

Preparation of 4-[5-(5-methyl-4-phenyl-thiazol-2-ylcarbamoyl)-pyridin-2-yl]-piperazine-1-carboxylic acid methyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-[5-(5-methyl-4-phenyl-thiazol-2-ylcarbamoyl)-pyridin-2-yl]-piperazine-1-carboxylic acid methyl ester was prepared from 6-chloro-N-(5-methyl-4-phenyl-thiazol-2-yl)-nicotinamide and piperazine-1-carboxylic acid methyl ester. LCMS calcd for C22H23N5O3S (m/e) 437, obsd 438 (M+H).

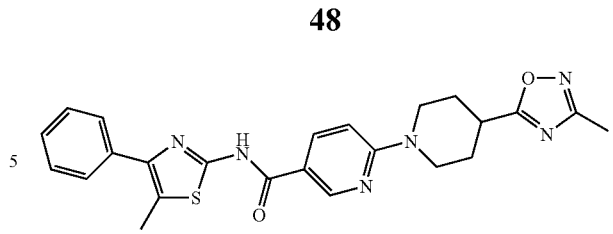

Example 20

4-(3-methyl-[1,2,4]oxadiazol-5-yl)-3,4,5,6-tetrahydro-2H-[1,2']bipyridinyl-5'-carboxylic acid (5-methyl-4-phenyl-thiazol-2-yl)-amide With a method similar to that used for the preparation of 4-(3-trifluoromethyl-phenyl)-3,4,5,6-tetrahydro-2H-[1,2']bipyridinyl-F-carboxylic acid (5-methyl-4-phenyl-thiazol-2-yl)-amide, 4-(3-methyl-[1,2,4]oxadiazol-5-yl)-3,4,5,6-tetrahydro-2H-[1,2']bipyridinyl-5'-carboxylic acid (5-methyl-4-phenyl-thiazol-2-yl)-amide was prepared from 6-chloro-N-(5-methyl-4-phenyl-thiazol-2-yl)-nicotinamide and 4-(3-methyl-[1,2,4]oxadiazol-5-yl)-piperidine. LCMS calcd for C24H24N6O2S (m/e) 460, obsd 461 (M+H).

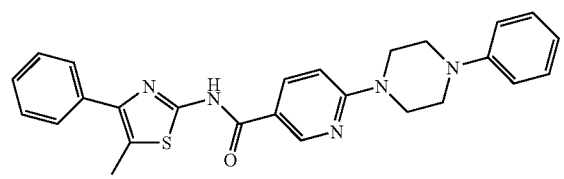

Example 21

N-(5-methyl-4-phenyl-thiazol-2-yl)-6-(4-phenyl-piperazin-1-yl)-nicatinamide

With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, N-(5-methyl-4-phenyl-thiazol-2-yl)-6-(4-phenyl-piperazin-1-yl)-nicotinamide was prepared from 6-chloro-N-(5-methyl-4-phenyl-thiazol-2-yl)-nicotinamide and 1-phenyl-piperazine. LCMS calcd for C26H25N5OS (m/e) 455, obsd 456 (M+H).

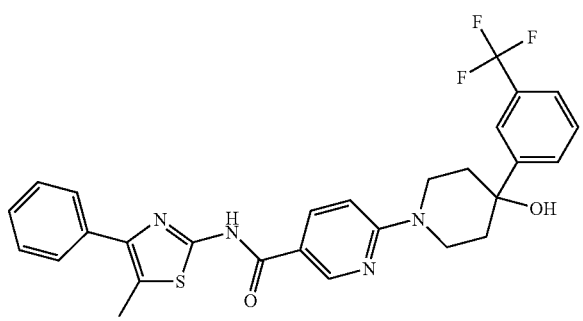

Example 22

4-Hydroxy-4-(3-trifluoromethyl-phenyl)-3,4,5,6-tetrahydro-2H-[1,2']bipyridinyl-5'-carboxylic acid (5-methyl-4-phenyl-thiazol-2-yl)-amide

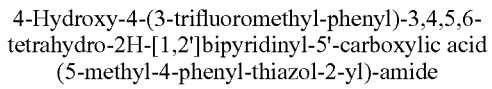

With a method similar to that used for the preparation of 4-(3-trifluoromethyl-phenyl)-3,4,5,6-tetrahydro-2H-[1,2']bipyridinyl-F-carboxylic acid (5-methyl-4-phenyl-thiazol-2-yl)-amide, 4-hydroxy-4-(3-trifluoromethyl-phenyl)-3,4,5,6-tetrahydro-2H-[1,2']bipyridinyl-5'-carboxylic acid (5-methyl-4-phenyl-thiazol-2-yl)-amide was prepared from 6-chloro-N-(5-methyl-4-phenyl-thiazol-2-yl)-nicotinamide and 4-(3-trifluoromethyl-phenyl)-piperidin-4-ol. LCMS calcd for C28H25F3N4O2S (m/e) 538, obsd 539 (M+H).

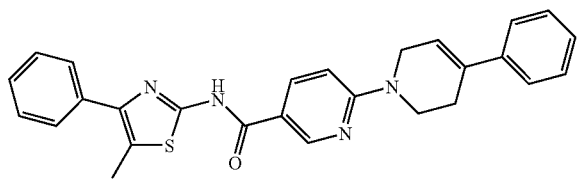

Example 23

4-phenyl-3,6-dihydro-2H-[1,2']bipyridinyl-5'-carboxylic acid (5-methyl-4-phenyl-thiazol-2-yl)-amide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-phenyl-3,6-dihydro-2H-[1,2']bipyridinyl-5'-carboxylic acid (5-methyl-4-phenyl-thiazol-2-yl)-amide was prepared from 6-chloro-N-(5-methyl-4-phenyl-thiazol-2-yl)-nicotinamide and 4-phenyl-1,2,3,6-tetrahydro-pyridine. LCMS calcd for C27H24N4OS (m/e) 452, obsd 453 (M+H).

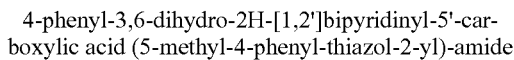

Example 24

6-(4-acetyl-piperazin-1-yl)-N-(5-methyl-4-phenyl-thiazol-2-yl)-nicotinamide

With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 6-(4-acetyl-piperazin-1-yl)-N-(5-methyl-4-phenyl-thiazol-2-yl)-nicotinamide was prepared from 6-chloro-N-(5-methyl-4-phenyl-thiazol-2-yl)-nicotinamide and 1-piperazin-1-yl-ethanone. LCMS calcd for C22H23N5O2S (m/e) 421, obsd 422 (M+H).

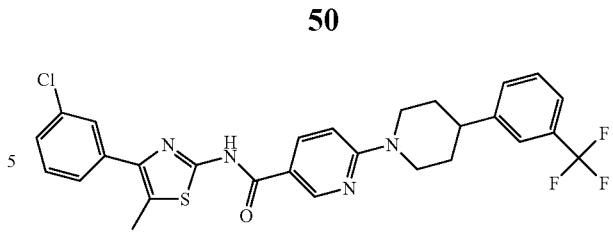

Example 25

4-(3-trifluoromethyl-phenyl)-3,4,5,6-tetrahydro-2H-[1,2']bipyridinyl-5'-carboxylic acid [4-(3-chloro-phenyl)-5-methyl-thiazol-2-yl]-amide With a method similar to that used for the preparation of 4-(3-trifluoromethyl-phenyl)-3,4,5,6-tetrahydro-2H[1,2']bipyridinyl-5'-carboxylic acid (5-methyl-4-phenyl-thiazol-2-yl)-amide, 4-(3-trifluoromethyl-phenyl)-3,4,5,6-tetrahydro-2H-[1,2']bipyridinyl-5'-carboxylic acid [4-(3-chloro-phenyl)-5-methyl-thiazol-2-yl]amide was prepared from 6-chloro-N-[4-(3-chloro-phenyl)-5-methyl-thiazol-2-yl]-nicotinamide and 4-(3-trifluoromethyl-phenyl)-piperidine. LCMS calcd for C28H24ClF3N4OS (m/e) 556, obsd 557 (M+H).

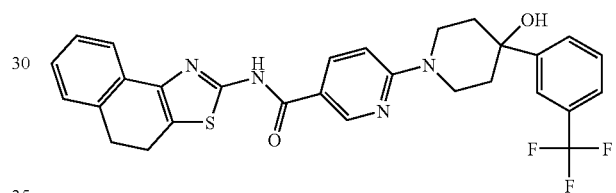

Example 26

4-Hydroxy-4-(3-trifluoromethyl-phenyl)-3,4,5,6-tetrahydro-2H-[1,2']pyridinyl-5% carboxylic acid (4,5-dihydro-naphtho[1,2-d]thiazol-2-yl)-amide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-hydroxy-4-(3-trifluoromethyl-phenyl)-3,4,5,6-tetrahydro-2H-[1,2']bipyridinyl-5"-carboxylic acid (4,5-dihydro-naphtho[1,2-d]thiazol-2-yl)-amide was prepared from 6-chloro-N-(4,5-dihydro-naphtho[1,2-d]thiazol-2-yl)-nicotinamide and 4-(3-trifluoromethyl-phenyl)-piperidin-4-ol. LCMS calcd for C29H25F3N4O2S (m/e) 550, obsd 551 (M+H).

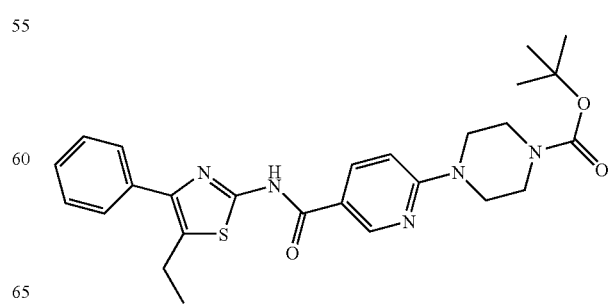

Example 27

4-[5-(5-ethyl-4-phenyl-thiazol-2-ylcarbamoyl)-pyridin-2-yl]-piperazine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-[5-(5-ethyl-4-phenyl-thiazol-2-ylcarbamoyl)-pyridin-2-yl]-piperazine-1-carboxylic acid tert-butyl ester was prepared from 6-chloro-N-(5-ethyl-4-phenyl-thiazol-2-yl)-nicotinamide and piperazine-1-carboxylic acid tert-butyl ester. LCMS calcd for C26H31N5O3S (m/e) 493, obsd 494 (M+H).

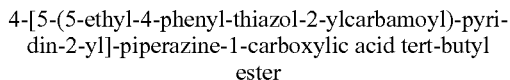

Example 28

N-(4,5-dihydro-naphtho[1,2-d]thiazol-2-yl)-6-morpholin-4-yl-nicotinamide

With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, N-(4,5-dihydro-naphtho[1,2-d]thiazol-2-yl)-6-morpholin-4-yl-nicotinamide was prepared from 6-chloro-N-(4,5-dihydro-naphtho[1,2-d]thiazol-2-yl)-nicotinamide and morpholine. LCMS calcd for C21H20N4O2S (m/e) 392, obsd 393 (M+H).

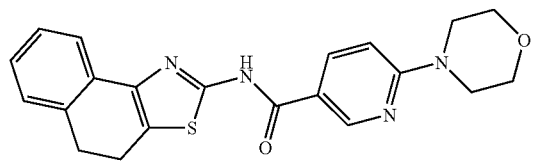

Example 29 methyl-[5'-(5-methyl-4-phenyl-thiazol-2-ylcarbamoyl)-3,4,5,6-tetrahydro-2H-[1,2']bipyridinyl-4-yl]-carbamic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, methyl-[5'-(5-methyl-4-phenyl-thiazol-2-ylcarbamoyl)-3,4,5,6-tetrahydro-2H-[1,2']bipyridinyl-4-yl]-carbamic acid tent-butyl ester was prepared from 6-chloro-N-(5-methyl-4-phenyl-thiazol-2-yl)-nicotinamide and methyl-piperidin-4-yl-carbamic acid tert-butyl ester. LCMS calcd for C27H33N5O3S (m/e) 507, obsd 508 (M+H).

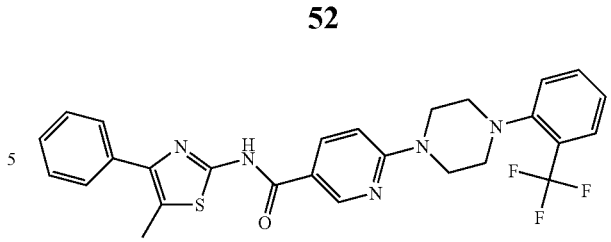

Example 30

N-(5-methyl-4-phenyl-thiazol-2-yl)-6-[4-(2-trifluoromethyl-phenyl)-piperazin-1-yl]-nicotinamide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, N-(5-methyl-4-phenyl-thiazol-2-yl)-6-[4-(2-trifluoromethyl-phenyl)-piperazin-1-yl]-nicotinamide was prepared from 6-chloro-N-(5-methyl-4-phenyl-thiazol-2-yl)-nicotinamide and 1-(2-trifluoromethyl-phenyl)-piperazine. LCMS calcd for C27H24F3N5OS (m/e) 523, obsd 524 (M+H).

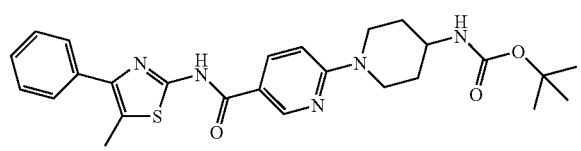

Example 31

[5'-(5-methyl-4-phenyl-thiazol-2-ylcarbamoyl)-3,4,5,6-tetrahydro-2H-[1,2']bipyridinyl-4-yl]-carbamic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, [5'-(5-methyl-4-phenyl-thiazol-2-yl)-carbamoyl)-3,4,5,6-tetrahydro-2H-[1,2']bipyridinyl-4-yl]-carbamic acid tent-butyl ester was prepared from 6-chloro-N-(5-methyl-4-phenyl-thiazol-2-yl)-nicotinamide and piperidin-4-yl-carbamic acid Pert-butyl ester. LCMS calcd for C26H31N5O3S (m/e) 493, obsd 494 (M+H).

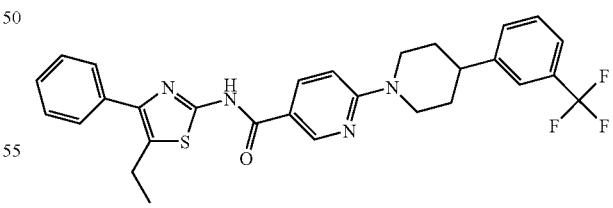

Example 32

4-(3-trifluoromethyl-phenyl)-3,4,5,6-tetrahydro-2H-[1,2']bipyridinyl-5'-carboxylic acid (5-ethyl-4-phenyl-thiazol-2-yl)-amide With a method similar to that used for the preparation of 4-(3-trifluoromethyl-phenyl)-3,4,5,6-tetrahydro-2H-[1,2']

bipyridinyl-5'-carboxylic acid (5-methyl-4-phenyl-thiazol-2-yl)-amide, 4-(3-trifluoromethyl-phenyl)-3,4,5,6-tetrahydro-2H-[1,2']bipyridinyl-5'-carboxylic acid (5-ethyl-4-phenyl-thiazol-2-yl)-amide was prepared from 6-chloro-N-(5-ethyl-4-phenyl-thiazol-2-yl)-nicotinamide and 4-(3-trifluoromethyl-phenyl)-piperidine. LCMS calcd for C29H27F3N4OS (m/e) 536, obsd 537 (M+H).

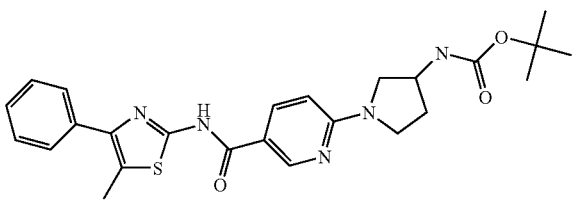

Example 33

{1-[5-(5-methyl-4-phenyl-thiazol-2-ylcarbamoyl)-pyridin-2-yl]-pyrrolidin-3-yl}-carbamic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, {1-[5-(5-methyl-4-phenyl-thiazol-2-ylcarbamoyl)-pyridin-2-yl]-pyrrolidin-3-yl}-carbamic acid tert-butyl ester was prepared from 6-chloro-N-(5-methyl-4-phenyl-thiazol-2-yl)-nicotinamide and pyrrolidin-3-yl-carbamic acid tert-butyl ester. LCMS calcd for C25H29N5O3S (m/e) 479, obsd 480 (M+H).

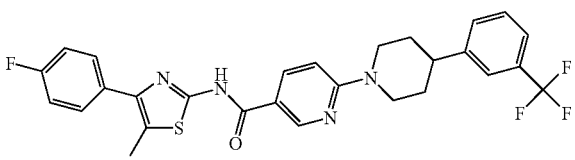

Example 34

4-(3-Trifluoromethyl-phenyl)-3,4,5,6-tetrahydro-2H-[1,2']bipyridinyl-5'-carboxylic acid [4-(4-fluoro-phenyl)-5-methyl-thiazol-2-yl]-amide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-(3-trifluoromethyl-phenyl)-3,4,5,6-tetrahydro-2H-[1,2']bipyridinyl-5'-carboxylic acid [4-(4-fluoro-phenyl)-5-methyl-thiazol-2-yl]-amide was prepared from 6-chloro-N-[4-(4-fluoro-phenyl)-5-methyl-thiazol-2-yl)-nicotinamide and 4-(3-trifluoromethyl-phenyl)-piperidine. LCMS calcd for C28H24F4N4OS (m/e) 540, obsd 541 (M+H).

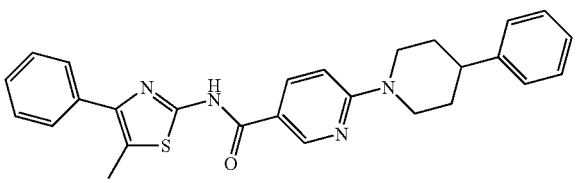

Example 35

4-Phenyl-3,4,5,6-tetrahydro-2H-[1,2']bipyridinyl-5'-carboxylic acid (5-methyl-4-phenyl-thiazol-2-yl)-amide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-phenyl-3,4,5,6-tetrahydro-2H-[1,2']bipyridinyl-5'-carboxylic acid (5-methyl-4-phenyl-thiazol-2-yl)-amide was prepared from 6-chloro-N-(5-methyl-4-phenyl-thiazol-2-yl)-nicotinamide and 4-phenyl-piperidine. LCMS calcd for C27H26N4OS (m/e) 454, obsd 455 (M+H).

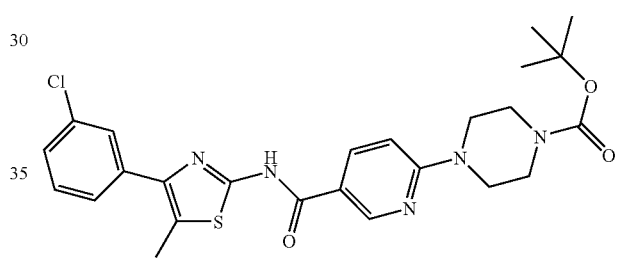

Example 36

4-{5-[4-(3-Chloro-phenyl)-5-methyl-thiazol-2-ylcarbamoyl]-pyridin-2-yl}-piperazine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-{5-[4-(3-chloro-phenyl)-5-methyl-thiazol-2-ylcarbamoyl]-pyridin-2-yl}-piperazine-1-carboxylic acid tert-butyl ester was prepared from 6-chloro-N-[4-(3-chloro-phenyl)-5-methyl-thiazol-2-yl)-nicotinamide and piperazine-1-carboxylic acid tert-butyl ester. LCMS calcd for C25H28ClN5O3S (m/e) 513, obsd 514 (M+H).

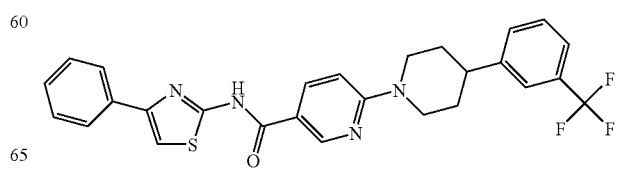

Example 37

4-(3-Trifluoromethyl-phenyl)-3,4,5,6-tetrahydro-2H-[1,2']bipyridinyl-5'-carboxylic acid (4-phenyl-thiazol-2-yl)-amide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-(3-trifluoromethyl-phenyl)-3,4,5,6-tetrahydro-2H-[1,2']bipyridinyl-5'-carboxylic acid (4-phenyl-thiazol-2-yl)-amide was prepared from 6-chloro-N-(4-phenyl-thiazol-2-yl)-nicotinamide and 4-(3-trifluoromethyl-phenyl)-piperidine. LCMS calcd for C27H23F3N4OS (m/e) 508, obsd 509 (M+H).

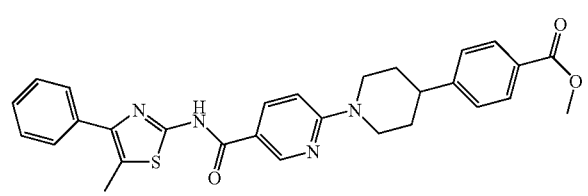

Example 38

4-[5'-(5-Methyl-4-phenyl-thiazol-2-ylcarbamoyl)-3,4,5,6-tetrahydro-2H-[1,2']bipyridinyl-4-yl]-benzoic acid methyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-[5'-(5-methyl-4-phenyl-thiazol-2-ylcarbamoyl)-3,4,5,6-tetrahydro-2H-[1,2']bipyridinyl-4-yl]-benzoic acid methyl ester was prepared from 6-chloro-N-(5-methyl-4-phenyl-thiazol-2-yl)-nicotinamide and 4-piperidin-4-yl-benzoic acid methyl ester. LCMS calcd for C29H28N4O3S (m/e) 512, obsd 513 (M+H).

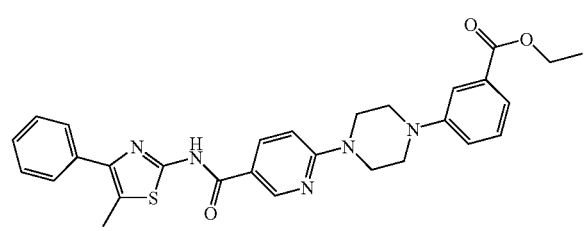

Example 39

3-{4-[5-(5-methyl-4-phenyl-thiazol-2-ylcarbamoyl)-pyridin-2-yl]-piperazin-1-yl}-benzoic acid ethyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 3-{4-[5-(5-methyl-4-phenyl-thiazol-2-ylcarbamoyl)-pyridin-2-yl]-piperazin-1-yl}-benzoic acid ethyl ester was prepared from 6-chloro-N-(5-methyl-4-phenyl-thiazol-2-yl)-nicotinamide and 3-piperazin-1-yl-benzoic acid ethyl ester. LCMS calcd for C29H29N5O3S (m/e) 527, obsd 528 (M+H).

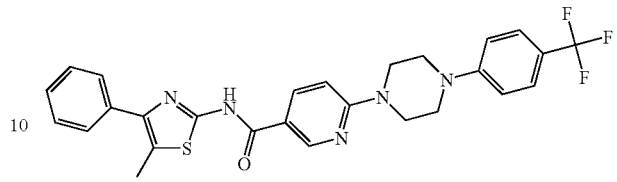

Example 40

N-(5-methyl-4-phenyl-thiazol-2-yl)-6-[4-(4-trifluoromethyl-phenyl)-piperazin-1-yl]-nicatinamide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, N-(5-methyl-4-phenyl-thiazol-2-yl)-6-[4-(4-trifluoromethyl-phenyl)-piperazin-1-yl]-nicatinamide was prepared from 6-chloro-N-(5-methyl-4-phenyl-thiazol-2-yl)-nicotinamide and 1-(4-trifluoromethyl-phenyl)-piperazine. LCMS calcd for C27H24F3N5OS (m/e) 523, obsd 524 (M+H).

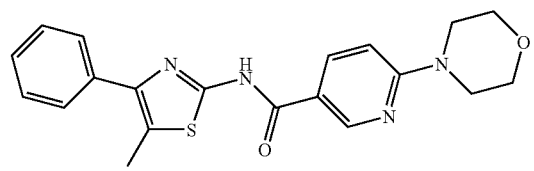

Example 41

N-(5-methyl-4-phenyl-thiazol-2-yl)-6-morpholin-4-yl-nicatinamide

With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, N-(5-methyl-4-phenyl-thiazol-2-yl)-6-morpholin-4-yl-nicotinamide was prepared from 6-chloro-N-(5-methyl-4-phenyl-thiazol-2-yl)-nicotinamide and morpholine. LCMS calcd for C20H20N4O2S (m/e) 380, obsd 381 (M+H).

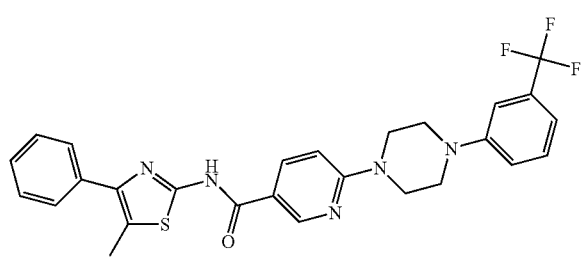

Example 42

N-(5-methyl-4-phenyl-thiazol-2-yl)-6-[4-(3-trifluoromethyl-phenyl)-piperazin-1-yl]-nicotinamide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, N-(5-methyl-4-phenyl-thiazol-2-yl)-6-[4-(3-trifluoromethyl-phenyl)-piperazin-1-yl]-nicotinamide was prepared from 6-chloro-N-(5-methyl-4-phenyl-thiazol-2-yl)-nicotinamide and 1-(3-trifluoromethyl-phenyl)-piperazine. LCMS calcd for C27H24F3N5OS (m/e) 523, obsd 524 (M+H).

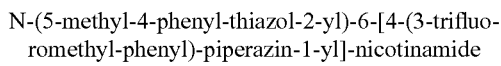

Example 43

N-(5-methyl-4-phenyl-thiazol-2-yl)-6-pyrrolidin-1-yl-nicotinamide

With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, N-(5-methyl-4-phenyl-thiazol-2-yl)-6-pyrrolidin-1-yl-nicotinamide was prepared from 6-chloro-N-(5-methyl-4-phenyl-thiazol-2-yl)-nicotinamide and pyrrolidine. LCMS calcd for C20H20N4OS (m/e) 364, obsd 365 (M+H).

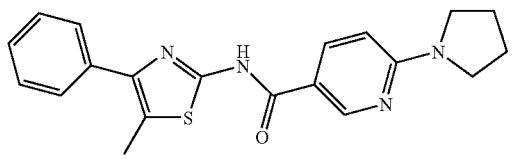

Example 44

4-[5-(5-methyl-4-p-tolyl-thiazol-2-ylcarbamoyl)-pyridin-2-yl]-piperazine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-[5-(5-methyl-4-p-tolyl-thiazol-2-ylcarbamoyl)-pyridin-2-yl]-piperazine-1-carboxylic acid tert-butyl ester was prepared from 6-chloro-N-(5-methyl-4-p-tolyl-thiazol-2-yl)-nicotinamide and piperazine-1-carboxylic acid tent-butyl ester. LCMS calcd for C26H31N5O3S (m/e) 493, obsd 494 (M+H).

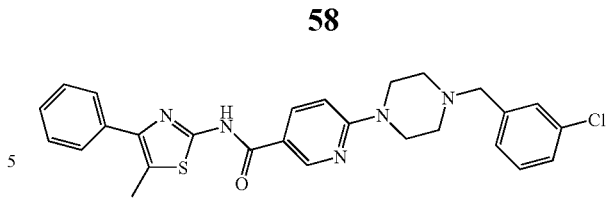

Example 45

6-[4-(3-chloro-benzyl)-piperazin-1-yl]-N-(5-methyl-4-phenyl-thiazol-2-yl)-nicotinamide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 6-[4-(3-chloro-benzyl)-piperazin-1-yl]-N-(5-methyl-4-phenyl-thiazol-2-yl)-nicotinamide was prepared from 6-chloro-N-(5-methyl-4-phenyl-thiazol-2-yl)-nicotinamide and 1-(3-chloro-benzyl)-piperazine. LCMS calcd for C27H26ClN5OS (m/e) 503, obsd 504 (M+H).

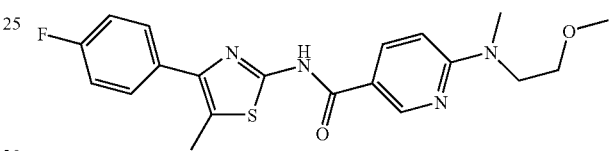

Example 46

N-[4-(4-fluoro-phenyl)-5-methyl-thiazol-2-yl]-6-[(2-methoxy-ethyl)-methyl-amino]-nicotinamide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, N-[4-(4-fluoro-phenyl)-5-methyl-thiazol-2-yl]-6-[(2-methoxy-ethyl)-methyl-amino]-nicotinamide was prepared from 6-chloro-N-[4-(4-fluoro-phenyl)-5-methyl-thiazol-2-yl]-nicotinamide and (2-methyoxy-ethyl)-methyl-amine. LCMS calcd for C20H21FN4O2S (m/e) 400, obsd 401 (M+H).

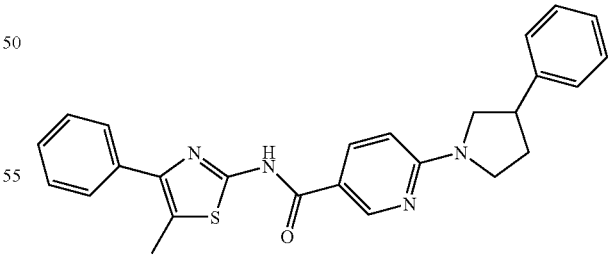

Example 47

(±)-N-(5-methyl-4-phenyl-thiazol-2-yl)-6-(3-phenyl-pyrrolidin-1-yl)-nicotinamide With a method similar to that used for the preparation of 4-(3-trifluoromethyl-phenyl)-3,4,5,6-tetrahydro-2H-[1,2']

bipyridinyl-5'-carboxylic acid (5-methyl-4-phenyl-thiazol-2-yl)-amide, racemic N-(5-methyl-4-phenyl-thiazol-2-yl)-6-(3-phenyl-pyrrolidin-1-yl)-nicotinamide was prepared from 6-chloro-N-(5-methyl-4-phenyl-thiazol-2-yl)-nicotinamide and racemic 3-phenyl-pyrrolidine. LCMS calcd for C26H24N4OS (m/e) 440, obsd 441 (M+H).

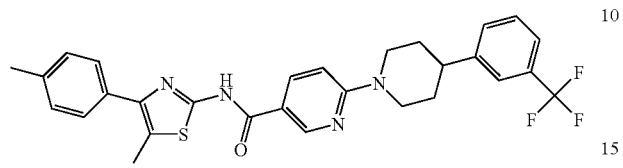

Example 48

4-(3-trifluoromethyl-phenyl)-3,4,5,6-tetrahydro-2H-[1,2']bipyridinyl-5'-carboxylic acid (5-methyl-4-p-tolyl-thiazol-2-yl)-amide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-(3-trifluoromethyl-phenyl)-3,4,5,6-tetrahydro-2H-[1,2']bipyridinyl-5'-carboxylic acid (5-methyl-4-p-tolyl-thiazol-2-yl)-amide was prepared from 6-chloro-N-(5-methyl-4-p-tolyl-thiazol-2-yl)-nicotinamide and 4-(3-trifluoromethyl-phenyl)-piperidine. LCMS calcd for C29H27F3N4OS (m/e) 536, obsd 537 (M+H).

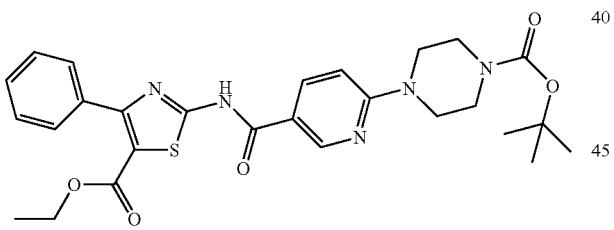

Example 49

4-[5-(5-ethoxycarbonyl-4-phenyl-thiazol-2-ylcarbamoyl)-pyridin-2-yl]-piperazine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-[5-(5-ethoxycarbonyl-4-phenyl-thiazol-2-ylcarbamoyl)-pyridin-2-yl]-piperazine-1-carboxylic acid tert-butyl ester was prepared from 2-[(6-chloro-pyridine-3-carbonyl)-amino]-4-phenyl-thiazole-5-carboxylic acid ethyl ester and piperazine-1-carboxylic acid tert-butyl ester. LCMS calcd for C27H31N5O5S (m/e) 537, obsd 538 (M+H).

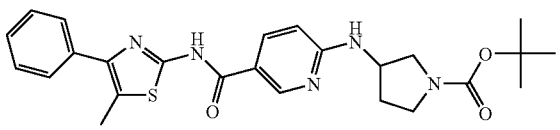

Example 50

(±)-3-[5-(5-methyl-4-phenyl-thiazol-2-ylcarbamoyl)-pyridin-2-ylamino]-pyrrolidine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, racemic 3-[5-(5-methyl-4-phenyl-thiazol-2-ylcarbamoyl)-pyridin-2-ylamino]-pyrrolidine-1-carboxylic acid tert-butyl ester was prepared from 6-chloro-N-(5-methyl-4-phenyl-thiazol-2-yl)-nicotinamide and racemic 3-amino-pyrrolidine-carboxylic acid tert-butyl ester. LCMS calcd for C25H29N5O3S (m/e) 479, obsd 480 (M+H).

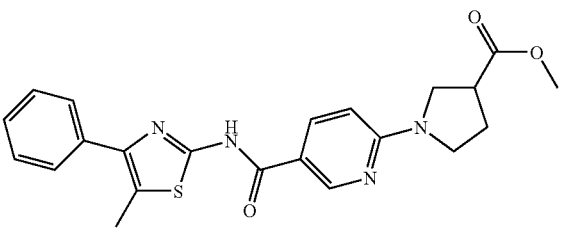

Example 51

(±)-1-[5-(5-methyl-4-phenyl-thiazol-2-ylcarbamoyl)-pyridin-2-yl]-pyrrolidine-3-carboxylic acid methyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, racemic 1-[5-(5-methyl-4-phenyl-thiazol-2-ylcarbamoyl)-pyridin-2-yl]-pyrrolidine-3-carboxylic acid methyl ester was prepared from 6-chloro-N-(5-methyl-4-phenyl-thiazol-2-yl)-nicotinamide and racemic pyrrolindine-3-carboxylic acid methyl ester. LCMS calcd for C22H22N4O3S (m/e) 422, obsd 423 (M+H).

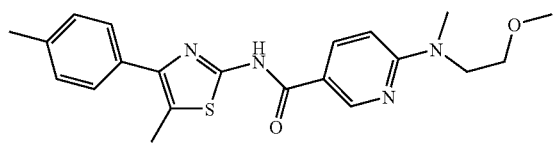

Example 52

Preparation of 6-[(2-methoxy-ethyl)-methyl-amino]-N-(5-methyl-4-p-tolyl-thiazol-2-yl)-nicotinamide With a method similar to that used for the preparation of 4-(3-trifluoromethyl-phenyl)-3,4,5,6-tetrahydro-2H-[1,2']- bipyridinyl-6-carboxylic acid (5-methyl-4-phenyl-thiazol-2-yl)-amide, 6-[(2-methoxy-ethyl)-methyl-amino]-N-(5-methyl-4-p-tolyl-thiazol-2-yl)-nicotinamide was prepared from 6-chloro-N-(5-methyl-4-p-tolyl-thiazol-2-yl)-nicotinamide and (2-methyoxy-ethyl)-methyl-amine. LCMS calcd for C21H24N4O2S (m/e) 396, obsd 397 (M+H).

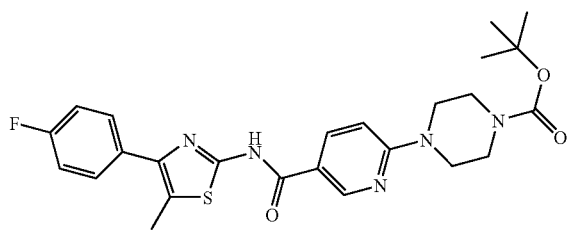

Example 53

Preparation of 4-{5-[4-(4-fluoro-phenyl)-5-methyl-thiazol-2-ylcarbamoyl]-pyridin-2-yl}-piperazine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-{5-[4-(4-fluoro-phenyl)-5-methyl-thiazol-2-ylcarbamoyl]-pyridin-2-yl}-piperazine-1-carboxylic acid tert-butyl ester was prepared from 6-chloro-N-[4-(4-fluoro-phenyl)-5-methyl-thiazol-2-yl)-nicotinamide and piperazine-1-carboxylic acid tert-butyl ester. LCMS calcd for C25H28FN5O3S (m/e) 497, obsd 498 (M+H).

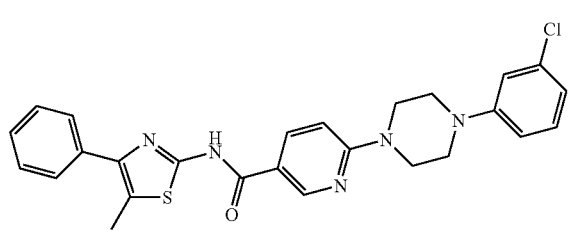

Example 54

Preparation of 6-[4-(3-chloro-phenyl)-piperazin-1-yl]-N-(5-methyl-4-phenyl-thiazol-2-yl)-nicotinamide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 6-[4-(3-chloro-phenyl)-piperazin-1-yl]-N-(5-methyl-4-phenyl-thiazol-2-yl)-nicotinamide was prepared from 6-chloro-N-(5-methyl-4-phenyl-thiazol-2-yl)-nicotinamide and 1-(3-chloro-phenyl)-piperazine. LCMS calcd for C26H24ClN5OS (m/e) 489, obsd 490 (M+H).

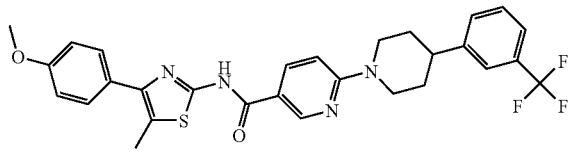

Example 55

Preparation of 4-(3-trifluoromethyl-phenyl)-3,4,5,6-tetrahydro-2H-[1,2']bipyridinyl-5'-carboxylic acid [4-(4-methoxy-phenyl)-5-methyl-thiazol-2-yl]-amide With a method similar to that used for the preparation of 4-(3-trifluoromethyl-phenyl)-3,4,5,6-tetrahydro-2H-1,2'-bipyridinyl-5'-carboxylic acid (5-methyl-4-phenyl-thiazol-2-yl)-amide, 4-(3-trifluoromethyl-phenyl)-3,4,5,6-tetrahydro-2H-[1,2']bipyridinyl-5'-carboxylic acid [4-(4-methoxy-phenyl)-5-methyl-thiazol-2-yl]amide was prepared from 6-chloro-N-[4-(4-methoxy-phenyl-5-methyl-thiazol-2-yl)-nicotinamide and 4-(3-trifluoromethyl-phenyl)-piperidine. LCMS calcd for C29H27F3N4O2S (m/e) 552, obsd 553 (M+H).

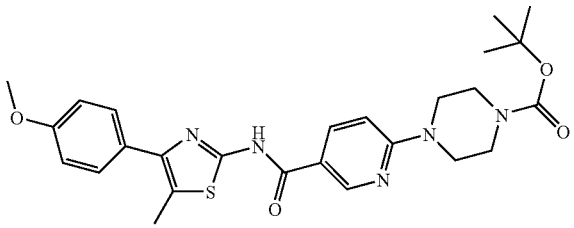

Example 56

Preparation of 4-{5-[4-(4-methoxy-phenyl)-5-methyl-thiazol-2-ylcarbamoyl]-pyridin-2-yl}-piperazine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-{5-[4-(4-methoxy-phenyl)-5-methyl-thiazol-2-ylcarbamoyl]-pyridin-2-yl}-piperazine-1-carboxylic acid tert-butyl ester was prepared from 6-chloro-N-[4-(4-methoxy-phenyl)-5-methyl-thiazol-2-yl)-nicotinamide and piperazine-1-carboxylic acid tent-butyl ester. LCMS calcd for C26H31N5O4S (m/e) 509, obsd 510 (M+H).

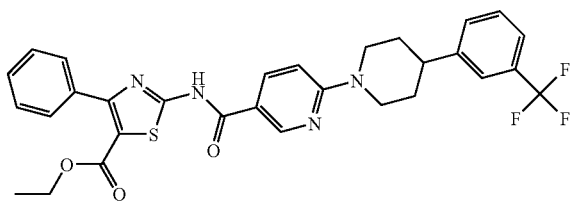

Example 57

Preparation of 4-phenyl-2-{[4-(3-trifluoromethyl-phenyl)-3,4,5,6-tetrahydro-2H-[1,2']bipyridinyl-5'-carbonyl]-amino}-thiazole-5-carboxylic acid ethyl ester With a method similar to that used for the preparation of 4-(3-trifluoromethyl-phenyl)-3,4,5,6-tetrahydro-2H-[1,2'] bipyridinyl-5'-carboxylic acid (5-methyl-4-phenyl-thiazol-2-yl)-amide, 4-phenyl-{[4-(3-trifluoromethyl-phenyl)-3,4,5,6-tetrahydro-2H-[1,2']bipyridinyl-5'-carbonyl]-amino}-thiazole-5-carboxylic acid ethyl ester was prepared from 2-[(6-chloro-pyridine-3-carbonyl)-amino]-4-phenyl-thiazole-5-carboxylic acid ethyl ester and 4-(3-trifluoromethyl-phenyl)piperidine. LCMS calcd for C30H27F3N4O3S (m/e) 580, obsd 581 (M+H).

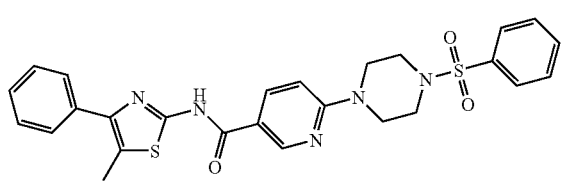

Example 58

Preparation of 6-(4-benzenesulfonyl-piperazin-1-yl)-N-(5-methyl-4-phenyl-thiazol-2-yl)-nicotinamide With a method similar to that used for the preparation of 4-(3-trifluoromethyl-phenyl)-3,4,5,6-tetrahydro-2H-[1,2'] bipyridinyl-5'-carboxylic acid (5-methyl-4-phenyl-thiazol-2-yl)-amide, 6-(4-benzenesulfonyl-piperazin-1-yl)-N-(5-methyl-4-phenyl-thiazol-2-yl)-nicotinamide was prepared from 6-chloro-N-(5-methyl-4-phenyl-thiazol-2-yl)-nicotinamide and 1-benzenesulfonyl-piperazine. LCMS calcd for C26H25N5O3S2 (m/e) 519, obsd 520 (M+H).

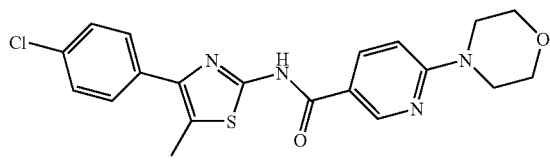

Example 59

N-[4-(4-chloro-phenyl)-5-methyl-thiazol-2-yl]-6-morpholin-4-yl-nicotinamide

With a method similar to that used for the preparation of 4-(3-trifluoromethyl-phenyl-3,4,5,6-tetrahydro-2H-[1,2']bipyridinyl-5'-carboxylic acid (5-methyl-4-phenyl-thiazol-2-yl)-amide, N-[4-(4-chloro-phenyl)-5-methyl-thiazol-2-yl]-6-morpholin-4-yl-nicotinamide was prepared from 6-chloro-N-[4-(4-chloro-phenyl)-5-methyl-thiazol-2-yl]-nicotinamide and morpholine. LCMS calcd for C20H19ClN4O2S (m/e) 414, obsd 415 (M+H).

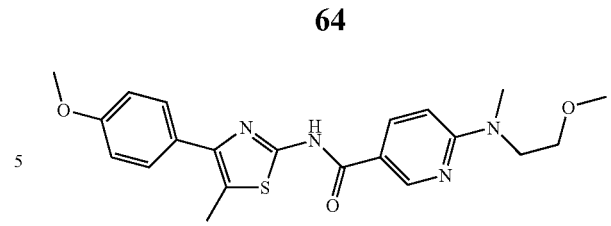

Example 60

6-[(2-methoxy-ethyl)-methyl-amino]-N-[4-(4-methoxy-phenyl)-5-methyl-thiazol-2-yl]-nicotinamide With a method similar to that used for the preparation of 4-(3-trifluoromethyl-phenyl)-3,4,5,6-tetrahydro-2H-[1,2'] bipyridinyl-5'-carboxylic acid (5-methyl-4-phenyl-thiazol-2-yl)-amide, 6-[(2-methoxy-ethyl)-methyl-amino]-N-[4-(4-methoxy-phenyl)-5-methyl-thiazol-2-yl]-nicotinamide was prepared from 6-chloro-N-[4-(4-methoxy-phenyl)-5-methyl-thiazol-2-yl]-nicotinamide and (2-methyoxy-ethyl)-methyl-amine. LCMS calcd for C21H24N4O3S (m/e) 412, obsd 413 (M+H).

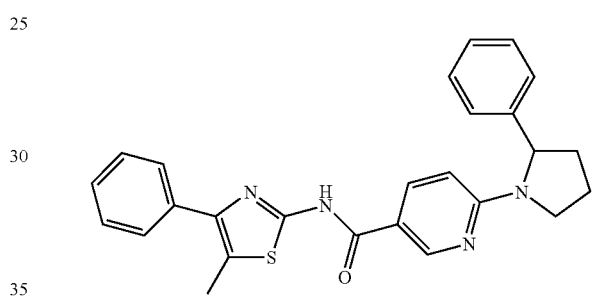

Example 61

(±) N-(5-methyl-4-phenyl-thiazol-2-yl)-6-(2-phenyl-pyrrolidin-1-yl)-nicatinamide With a method similar to that used for the preparation of 4-(3-trifluoromethyl-phenyl)-3,4,5,6-tetrahydro-2H-[1,2'] bipyridinyl-5'-carboxylic acid (5-methyl-4-phenyl-thiazol-2-yl)-amide, racemic N-(5-methyl-4-phenyl-thiazol-2-yl)-6-(2-phenyl-pyrrolidin-1-yl)-nicotinamide was prepared from 6-chloro-N-(5-methyl-4-phenyl-thiazol-2-yl)-nicotinamide and racemic 2-phenyl-pyrrolidine. LCMS calcd for C26H24N4OS (m/e) 440, obsd 441 (M+H).

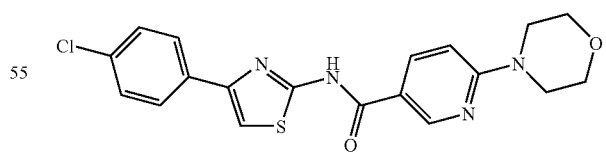

Example 62

N-[4-(4-chloro-phenyl)-thiazol-2-yl]-6-morpholin-4-yl-nicotinamide

With a method similar to that used for the preparation of 4-(3-trifluoromethyl-phenyl)-3,4,5,6-tetrahydro-2H-[1,2']

bipyridinyl-5'-carboxylic acid (5-methyl-4-phenyl-thiazol-2-yl)-amide, N-[4-(4-chloro-phenyl)-thiazol-2-yl]-6-morpholin-4-yl-nicotinamide was prepared from 6-chloro-N-[4-(4-chloro-phenyl)-thiazol-2-yl)-nicotinamide and morpholine. LCMS calcd for C19H17ClN4O2S (m/e) 400, obsd 401 (M+H).

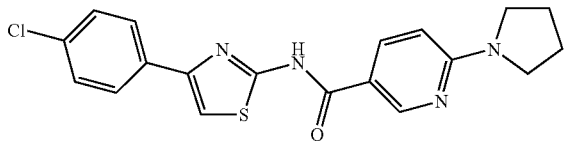

Example 63

N-[4-(4-chloro-phenyl)-thiazol-2-yl]-6-pyrrolidin-1-yl-nicotinamide

With a method similar to that used for the preparation of 4-(3-trifluoromethyl-phenyl)-3,4,5,6-tetrahydro-2H-[1,2'] bipyridinyl-5'-carboxylic acid (5-methyl-4-phenyl-thiazol-2-yl)-amide, N-[4-(4-chloro-phenyl)-thiazol-2-yl]-6-pyrrolidin-1-yl-nicotinamide was prepared from 6-chloro-N-[4-(4-chloro-phenyl)-thiazol-2-yl)-nicotinamide and pyrrolidine. LCMS calcd for C19H17ClN4OS (mole) 384, obsd 385 (M+H).

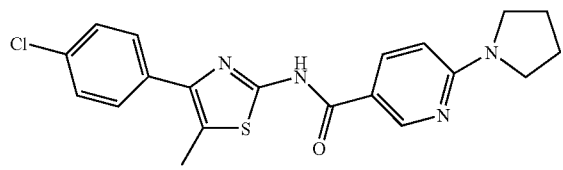

Example 64

N-[4-(4-chloro-phenyl)-5-methyl-thiazol-2-yl]-6-pyrrolidin-1-yl-nicotinamide

With a method similar to that used for the preparation of 4-(3-trifluoromethyl-phenyl)-3,4,5,6-tetrahydro-2H[1,2']bipyridinyl-5'-carboxylic acid (5-methyl-4-phenyl-thiazol-2-yl)-amide, N-[4-(4-chloro-phenyl)-5-methyl-thiazol-2-yl]-6-pyrrolidin-1-yl-nicotinamide was prepared from 6-chloro-N-[4-(4-chloro-phenyl)-5-methyl-thiazol-2-yl)-nicotinamide and pyrrolidine. LCMS calcd for C20H19ClN4OS (m/e) 398, obsd 399 (M+H).

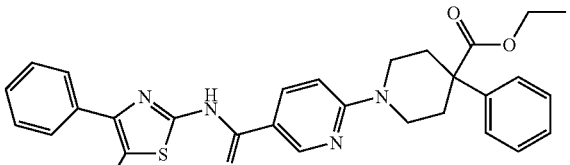

Example 65

5'-(5-methyl-4-phenyl-thiazol-2-ylcarbamoyl)-4-phenyl-3,4,5,6-tetrahydro-2H-[1,2']bipyridinyl-4-carboxylic acid ethyl ester With a method similar to that used for the preparation of 4-(3-trifluoromethyl-phenyl)-3,4,5,6-tetrahydro-2H-[1,2'] bipyridinyl-5'-carboxylic acid (5-methyl-4-phenyl-thiazol-2-yl)-amide, 5'-(5-methyl-4-phenyl-thiazol-2-ylcarbamoyl)-4-phenyl-3,4,5,6-tetrahydro-2H-[1,2']bipyridinyl-4-carboxylic acid ethyl ester was prepared from 6-chloro-N-(5-methyl-4-phenyl-thiazol-2-yl)-nicotinamide and 4-phenyl-piperidine-4-carboxylic acid ethyl ester. LCMS calcd for C30H30N4O3S (m/e) 526, obsd 527 (M+H).

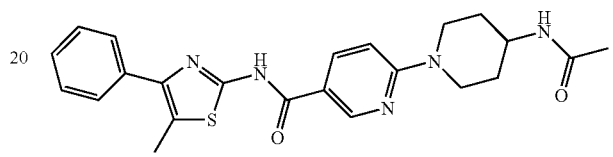

Example 66

4-acetylamino-3,4,5,6-tetrahydro-2H-[1,2']bipyridinyl-5'-carboxylic acid (5-methyl-4-phenyl-thiazol-2-yl)-amide With a method similar to that used for the preparation of 4-(3-trifluoromethyl-phenyl)-3,4,5,6-tetrahydro-2H-[1,2'] bipyridinyl-5'-carboxylic acid (5-methyl-4-phenyl-thiazol-2-yl)-amide, 4-acetylamino-3,4,5,6-tetrahydro-2H-[1,2']bipyridinyl-5'-carboxylic acid (5-methyl-4-phenyl-thiazol-2-yl)-amide was prepared from 6-chloro-N-(5-methyl-4-phenyl-thiazol-2-yl)-nicotinamide and N-piperidin-4-yl-acetamide. LCMS calcd for C23H25N5O2S (m/e) 435, obsd 436 (M+H).

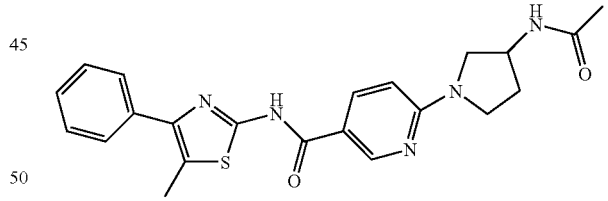

Example 67

(±)-6-(3-acetylamino-pyrrolidin-1-yl)-N-(5-methyl-4-phenyl-thiazol-2-yl)-nicotinamide With a method similar to that used for the preparation of 4-(3-trifluoromethyl-phenyl)-3,4,5,6-tetrahydro-2H-[1,2'] bipyridinyl-5'-carboxylic acid (5-methyl-4-phenyl-thiazol-2-yl)-amide, racemic 6-(3-acetylamino-pyrrolidin-1-yl)-N-(5-methyl-4-phenyl-thiazol-2-yl)-nicotinamide was prepared from 6-chloro-N-(5-methyl-4-phenyl-thiazol-2-yl)-nicotinamide and racemic N-pyrrolidin-3-yl-acetamide. LCMS calcd for C22H23N5O2S (m/e) 421, obsd 422 (M+H).

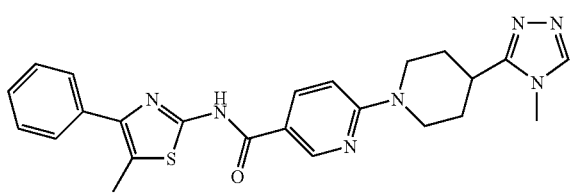

Example 68

4-(4-methyl-4H-[1,2,4]triazol-3-yl)-3,4,5,6-tetrahydro-2H-[1,2']bipyridinyl-5'-carboxylic acid (5-methyl-4-phenyl-thiazol-2-yl)-amide With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-(4-methyl-4H-[1,2,4]triazol-3-yl)-3,4,5,6-tetrahydro-2H-[1,2']bipyridinyl-5-carboxylic acid (5-methyl-4-phenyl-thiazol-2-yl)-amide was prepared from 6-chloro-N-(5-methyl-4-phenyl-thiazol-2-yl)-nicotinamide and 4-(4-methyl-4H-[1,2,4]triazol-3-yl)-piperidine. LCMS calcd for C24H25N7OS (m/e) 459, obsd 460 (M+H).

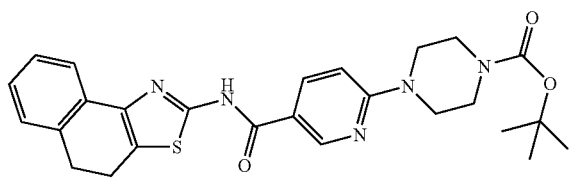

Example 69

4-[5-(4,5-dihydro-naphtho[1,2-d]thiazol-2-ylcarbamoyl)-pyridin-2-yl]-piperazine-1-carboxylic acid tert-butyl ester With a method similar to that used for the preparation of 4-(3-trifluoromethyl-phenyl)-3,4,5,6-tetrahydro-2H-[1,2']bipyridinyl-5'-carboxylic acid (5-methyl-4-phenyl-thiazol-2-yl)-amide, 4-[5-(4,5-dihydro-naphtho[1,2-d]thiazol-2-ylcarbamoyl)-pyridin-2-yl]-piperazine-1-carboxylic acid tert-butyl ester was prepared from 6-chloro-N-(4,5-dihydro-naphtho[1,2-c]thiazol-2-yl)-nicotinamide and piperazine-1-carboxylic acid tent-butyl ester. LCMS calcd for C26H29N5O3S (m/e) 491, obsd 492 (M+H).

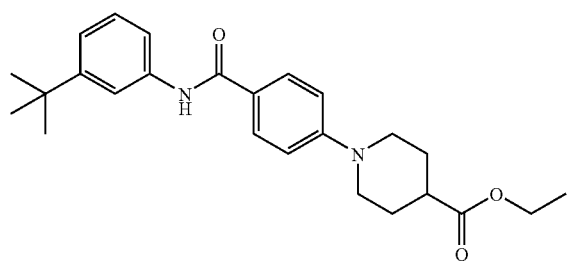

Example 70

1-[4-(3-tert-Butyl-phenylcarbamoyl)-phenyl]-piperidine-4-carboxylic acid ethyl ester A mixture of 3-tert-butyl aniline (54 mg, 0.36 mmol), 1-(4-carboxy-phenyl)-piperidine-4-carboxylic acid ethyl ester (100 mg, 0.36 mmol) and EDCI (200 mg, 1.08 mmol) in $CH_2Cl_2$ was stirred at room temperature overnight. Next morning the reaction mixture was partitioned between EtOAc and water. The organic layer was separated dried over $Na_2SO_4$, filtered and concentrated. The residue was purified on a silica gel column with 20-50% $Et_2O$ in hexanes gradient to afford the product (31 mg; Yield: 21%). HRMS m/z calcd for C25H32N2O3 [M+H]$^+$: 409.2486. Found: 409.2484.

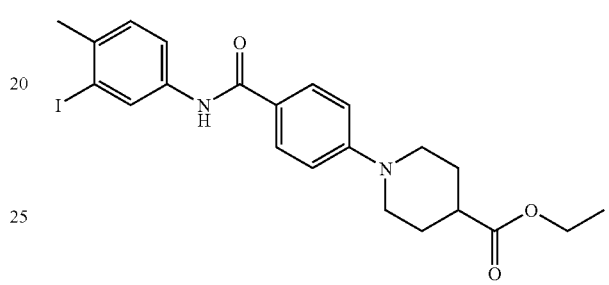

Example 71

1-[4-(3-Iodo-4-methyl-phenylcarbamoyl)-phenyl]-piperidine-4-carboxylic acid ethyl ester 1-[4-(3-Iodo-4-methyl-phenylcarbamoyl)-phenyl]-piperidine-4-carboxylic acid ethyl ester was prepared from 3-iodo-4-methyl aniline and 1-(4-carboxy-phenyl)-piperidine-4-carboxylic acid ethyl ester following a procedure similar to the one described in the synthesis of 1-[4-(3-tert-Butyl-phenylcarbamoyl)-phenyl]-piperidine-4-carboxylic acid ethyl ester above. The product was isolated after a silica gel column with a 20-50% $Et_2O$ in hexanes gradient followed by a 50% EtOAc in hexanes elution. HRMS m/z calcd for C22H25N2O3I [M+H]$^+$: 493.0983. Found: 493.0982.

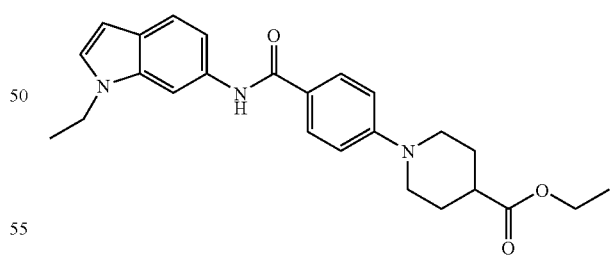

Example 72

1-[4-(1-Ethyl-1H-indol-6-ylcarbamoyl)-phenyl]-piperidine-4-carboxylic acid ethyl ester A slurry of 1-ethyl-6-nitro-1H-indole (100 mg, 0.52 mmol) and 10% Pd/C (21 mg) in EtOH was hydrogenated under 1 atm of $H_2$ for 2 h. The mixture was filtered and concentrated and the intermediate amine was dissolved in $CH_2Cl_2$ (5 mL)

and treated with 1-(4-carboxy-phenyl)-piperidine-4-carboxylic acid ethyl ester (110 mg, 0.39 mmol) and EDCI (228 mg, 1.19 mmol). After stirring overnight the reaction mixture was partitioned between EtOAc and water. The EtOAc layer was collected, filtered and concentrated. The residue was chromatographed with 20-60% EtOAc in hexanes to afford the product (57 mg, Yield: 34%). HRMS m/z calcd for C25H29N3O3 [M+H]+: 420.2282. Found: 420.2280.

and a catalytic amount of DMAP in dioxane, in a sealed tube was heated at 85° C. for 19 h. Followed addition of another portion of ethyl isonipecotate (60 mg, 0.38 mmol) and the mixture was heated at 95° C. for 24 h. The mixture was then cooled, the solvent was evaporated and the residue was purified with a silica gel column and 20-40% EtOAc in hexanes to afford the product. HRMS m/z calcd for C20H21N3O3ClI [M+H]+: 514.0389. Found: 514.0387.

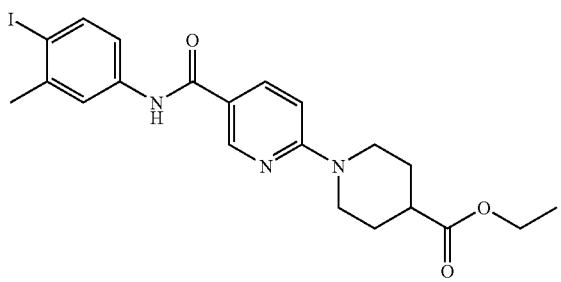

Example 73

5'-(4-Iodo-3-methyl-phenylcarbamoyl)-3,4,5,6-tetrahydro-2H-[1,2']bipyridinyl-4-carboxylic acid ethyl ester A solution of 6-chloro-N-(4-iodo-3-methyl-phenyl)-nicotinamide (500 mg, 1.34 mmol), ethyl isonipecotate (250 mg, 1.61 mmol) and diisopropylethyl amine (0.7 mL, 4.02 mmol) in dioxane (15 mL) was heated at 80° C. in a sealed tube for 18.5 h then at 95° C. for 9 h and then at 115° C. for an additional 24 h. The reaction mixture was then cooled, another portion of ethyl isonipecotate (250 mg, 1.61 mmol) was added and the mixture was stirred at 115° C. for 8 h more. The mixture was then cooled and portioned between EtOAc and water. The EtOAc layer was dried over Na2SO4, filtered and concentrated. The residue was chromatographed with a silica gel column and 10-40% EtOAc in hexanes gradient to afford the product. (300 mg, Yield: 45%). HRMS m/z calcd for C21H24N3O3I [M+H]+: 494.0935. Found: 494.0937.

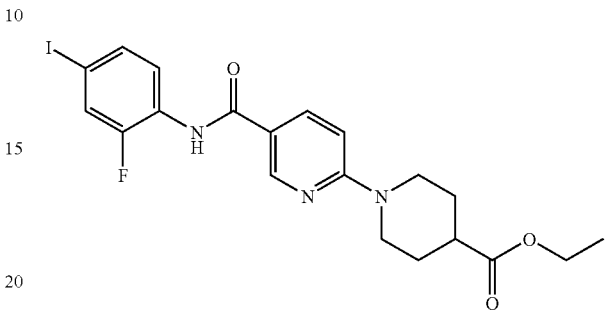

Example 75

5'-(2-Fluoro-4-iodo-phenylcarbamoyl)-3,4,5,6-tetrahydro-2H-[1,2']bipyridinyl-4-carboxylic acid ethyl ester 6-Chloro-N-(2-fluoro-4-iodo-phenyl)-nicotinamide (80 mg, 0.22 mmol) was dissolved in dioxane (6 mL) and the mixture was treated with diisopropyl ethyl amine (0.11 mL, 0.66 mmol), ethyl isonipecotate (100 mg, 0.66 mmol) and a catalytic amount of DMAP. This solution was then heated in a sealed tube at 95° C. for 21 h. The mixture was then cooled and the solvent was evaporated. The residue was chromatographed with a silica gel column and 20-40% EtOAc in hexanes gradient to afford the product. (60 mg, Yield: 55%)

HRMS m/z calcd for C20H21N3O3FI [M+H]+: 498.0865. Found: 498.0862.

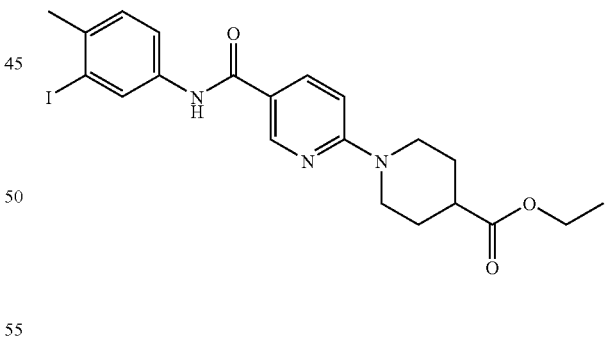

Example 76

5'-(3-Iodo-4-methyl-phenylcarbamoyl)-3,4,5,6-tetrahydro-2H-[1,2']bipyridinyl-4-carboxylic acid ethyl ester A solution of 6-chloro-N-(3-iodo-4-methyl-phenyl)-nicotinamide (360 mg, 0.97 mmol), ethyl isonipecotate (460 mg, 2.91 mmol), diisopropylethyl amine (0.51 mL, 2.91 mmol) and a catalytic amount of DMAP in dioxane (15 mL) was heated at 120° C. in a sealed tube until consumption of the limiting reagent, as judged by TLC. The reaction mixture was

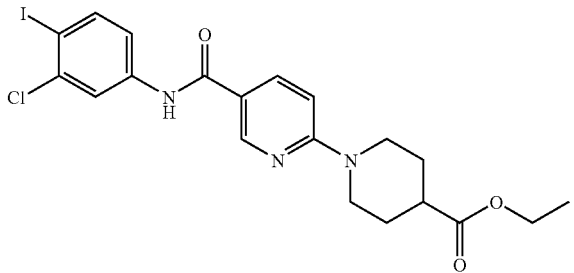

Example 74

5'-(3-Chloro-4-iodo-phenylcarbamoyl)-3,4,5,6-tetrahydro-2H-[1,2']bipyridinyl-4-carboxylic acid ethyl ester A solution of 6-Chloro-N-(3-chloro-4-iodo-phenyl)-nicotinamide (100 mg, 0.26 mmol), ethyl isonipecotate (60 mg, 0.38 mmol), diisopropyl ethyl amine (0.14 mL, 0.77 mmol)

then cooled and partitioned between EtOAc and water. The organic layer was then dried over Na₂SO₄, filtered and concentrated. The residue was purified with a silica gel column and 0-50% EtOAc in hexanes gradient to afford the product (360 mg, Yield 75%). HRMS m/z calcd for C21H24N3O3I [M+H]⁺: 494.0935. Found: 494.0935.

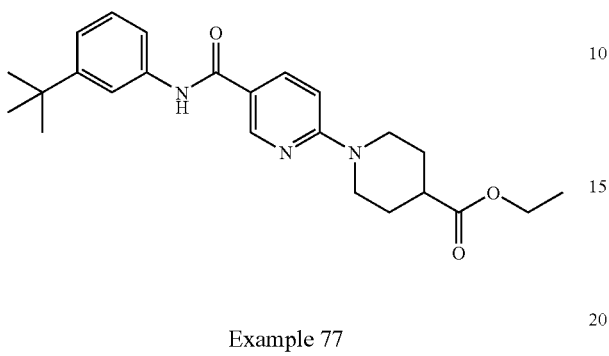

Example 77

5'-(3-tert-Butyl-phenylcarbamoyl)-3,4,5,6-tetrahydro-2H-[1,2']bipyridinyl-4-carboxylic acid ethyl ester 5'-(3-tert-Butyl-phenylcarbamoyl)-3,4,5,6-tetrahydro-2H-[1,2']bipyridinyl-4-carboxylic acid ethyl ester was prepared from N-(3-tert-butyl-phenyl)-6-chloro-nicotinamide and ethyl isonipecotate following a procedure similar to the one described in the synthesis of 5'-(3-iodo-4-methyl-phenylcarbamoyl)-3,4,5,6-tetrahydro-2H-[1,2']bipyridinyl-4 carboxylic acid ethyl ester above. The product was isolated by silica gel column purification with 20-30% EtOAc in hexanes gradient. FIRMS m/z calcd for C24H31N3O3 [M+H]⁺: 410.2438. Found: 410.2436

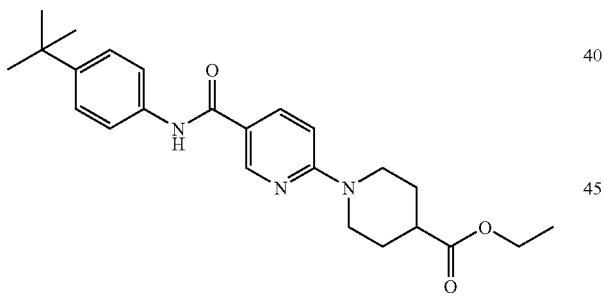

Example 78

5'-(4-tert-Butyl-phenylcarbamoyl)-3,4,5,6-tetrahydro-2H-[1,2']bipyridinyl-4-carboxylic acid ethyl ester 5'-(4-tert-Butyl-phenylcarbamoyl)-3,4,5,6-tetrahydro-2H-[1,2']bipyridinyl-4-carboxylic acid ethyl ester was prepared from N-(4-tert-butyl-phenyl)-6-chloro-nicotinamide and ethyl isonipecotate following a procedure similar to the one described in the synthesis of 5'-(3-iodo-4-methyl-phenylcarbamoyl)-3,4,5,6-tetrahydro-2H-[1,2']bipyridinyl-4 carboxylic acid ethyl ester above. The product was isolated by silica gel column purification with 20-30% EtOAc in hexanes gradient. HRMS m/z calcd for C24H31N3O3 [M+H]: 410.2438. Found: 410.2439.

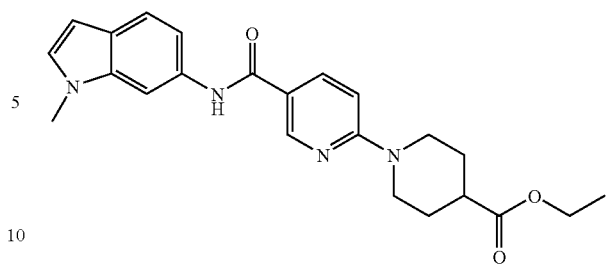

Example 79

5'-(1-Methyl-1H-indol-6-ylcarbamoyl)-3,4,5,6-tetrahydro-2H-[1,2']pyridinyl-4-carboxylic acid ethyl ester 5'-(1-Methyl-1H-indol-6-ylcarbamoyl)-3,4,5,6-tetrahydro-2H-[1,2']bipyridinyl-4-carboxylic acid ethyl ester was prepared from 6-chloro-N-(1-methyl-1H-indol-6-yl)-nicotinamide and ethyl isonipecotate following a procedure similar to the one described in the synthesis of 5'43-iodo-4-methyl-phenylcarbamoyl)-3,4,5,6-tetrahydro-2H-[1,2']bipyridinyl-4 carboxylic acid ethyl ester above. The product was isolated by silica gel column purification with 20-40% EtOAc in hexanes gradient. HRMS m/z calcd for C23H26N4O3 [M+H]⁺: 407.2078. 407.2076.

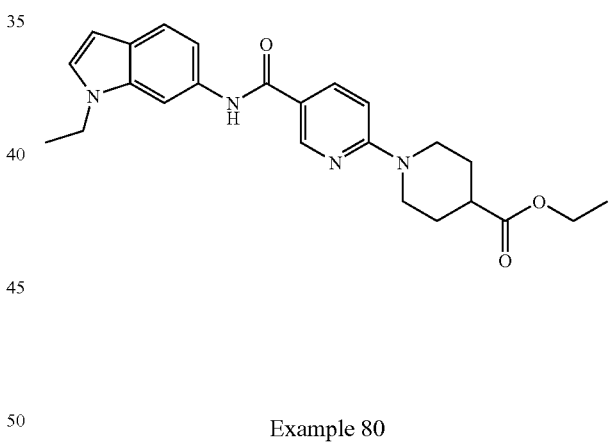

Example 80

5'-(1-Ethyl-1H-indol-6-ylcarbamoyl)-3,4,5,6-tetrahydro-2H-[1,2']bipyridinyl-4-carboxylic acid ethyl ester 5'-(1-Ethyl-1H-indol-6-ylcarbamoyl)-3,4,5,6-tetrahydro-2H-[1,2']bipyridinyl-4-carboxylic acid ethyl ester was prepared from 6-chloro-N-(1-ethyl-1H-indol-6-yl)-nicotinamide and ethyl isonipecotate following a procedure similar to the one described in the synthesis of 5-(3-iodo-4-methyl-phenylcarbamoyl)-3,4,5,6-tetrahydro-2H-[1,2']bipyridinyl-4 carboxylic acid ethyl ester above. The product was isolated by silica gel column purification with 20-40% EtOAc in hexanes gradient. HRMS m/z calcd for C24H28N4O3 [M+H]⁺: 421.2234. Found: 421.2234.

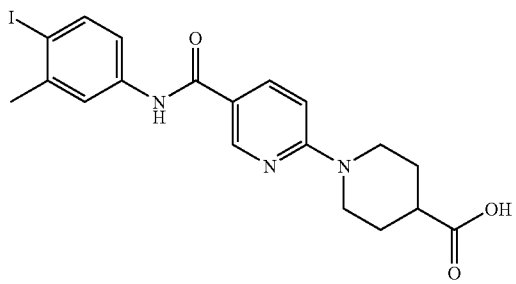

Example 81

5'-(4-Iodo-3-methyl-phenylcarbamoyl)-3,4,5,6-tetrahydro-2H-[1,2']bipyridinyl-4-carboxylic acid A solution of 5'-(4-iodo-3-methyl-phenylcarbamoyl)-3,4,5,6-tetrahydro-2H-[1,2']bipyridinyl-4-carboxylic acid ethyl ester (200 mg, 0.39 mmol) in THF (10 mL) and H$_2$O (2 mL) was treated with LiOH monohydrate (33 mg, 0.78 mmol). The mixture was stirred at room temperature for 24 h and then partitioned between EtOAc and H$_2$O. The acidity of the water layer was adjusted to pH 5 by the addition of aqueous conc. HCl and solid Na$_2$CO$_3$. The water layer was separated and extracted once more with EtOAc. The EtOAc layers were combined, dried over Na$_2$SO$_4$, filtered and concentrated. The solid residue was suspended in CH$_2$Cl$_2$ then filtered and dried to afford the product (70 mg, Yield: 38%). HRMS m/z calcd for C19H20N3O3I [M+H]$^+$: 46.0622. Found: 466.0619.

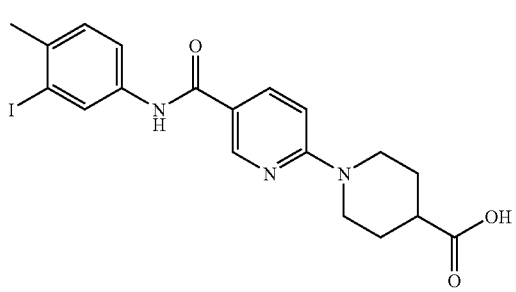

Example 82

5'-(3-Iodo-4-methyl-phenylcarbamoyl)-3,4,5,6-tetrahydro-2H-[1,2']bipyridinyl-4-carboxylic acid 5'-(3-Iodo-4-methyl-phenylcarbamoyl)-3,4,5,6-tetrahydro-2H-[1,2']bipyridinyl-4-carboxylic acid was prepared by the hydrolysis of 5'-(3-iodo-4-methyl-phenylcarbamoyl)-3,4,5,6-tetrahydro-2H-[1,2']bipyridinyl-4 carboxylic acid ethyl ester with LiOH monohydrate in a manner similar to the one described in the synthesis of 5'-(4-iodo-3-methyl-phenylcarbamoyl)-3,4,5,6-tetrahydro-2H-[1,2']bipyridinyl-4-carboxylic acid above. HRMS m/z calcd for C19H20N3O3I [M+H]$^+$: 466.0622. Found: 466.0620.

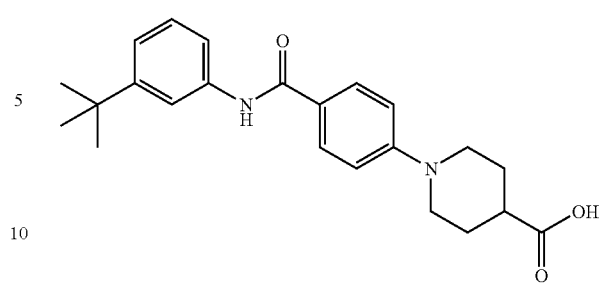

Example 83

1-[4-(3-tert-Butyl-phenylcarbamoyl)-phenyl]-piperidine-4-carboxylic acid

1-[4-(3-tert-Butyl-phenylcarbamoyl)-phenyl]-piperidine-4-carboxylic acid was prepared by the hydrolysis of 1-[4-(3-tert-butyl-phenylcarbamoyl)-phenyl]-piperidine-4-carboxylic acid ethyl ester with LiOH monohydrate in a manner similar to the one described in the synthesis of 5'-(4-iodo-3-methyl-phenylcarbamoyl)-3,4,5,6-tetrahydro-2H-[1,2']bipyridinyl-4-carboxylic acid above. HRMS m/z calcd for C23H28N2O3 [M+H]$^+$: 381.2173. Found: 381.2173.

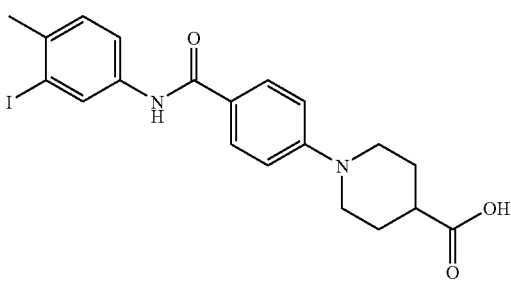

Example 84

1-[4-(3-Iodo-4-methyl-phenylcarbamoyl)-phenyl]-piperidine-4-carboxylic add

1-[4-(3-Iodo-4-methyl-phenylcarbamoyl)-phenyl]-piperidine-4-carboxylic acid was prepared by the hydrolysis of 1-[4-(3-iodo-4-methyl-phenylcarbamoyl)-phenyl]-piperidine-4-carboxylic acid ethyl ester with LiOH monohydrate in a manner similar to the one described in the synthesis of 5"-(4-iodo-3-methyl-phenylcarbamoyl)-3,4,5,6-tetrahydro-2H-[1,2']bipyridinyl-4-carboxylic acid above. HRMS m/z calcd for C20H21N2O3I [M+H]$^+$: 465.0670. Found: 465.0667.

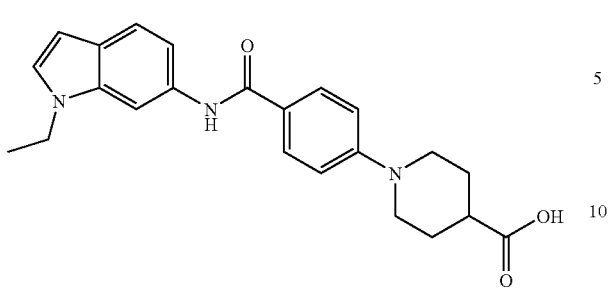

Example 85

1-[4-(1-Ethyl-1H-1-indol-6-ylcarbamoyl)-phenyl]-piperidine-4-carboxylic acid 1-[4-(1-Ethyl-1H-indol-6-ylcarbamoyl)-phenyl]-piperidine-4-carboxylic acid was prepared by the hydrolysis of 1-[4-(1-ethyl-1H-indol-6-ylcarbamoyl)-phenyl]-piperidine-4-carboxylic acid ethyl ester with LiOH monohydrate in a manner similar to the one described in the synthesis of 5'-(4-iodo-3-methyl-phenylcarbamoyl)-3,4,5,6-tetrahydro-2H-[1,2']bipyridinyl-4-carboxylic acid above. HRMS m/z calcd for C23H25N3O3 [M+H]$^+$; 392.1969. Found: 392.1968

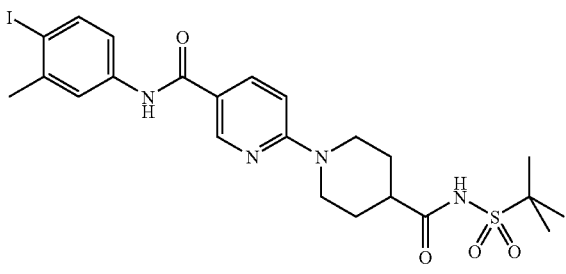

Example 86

4-(2-Methyl-propane-2-sulfonylaminocarbonyl)-3,4,5,6-tetrahydro-2H-[1,2']bipyridinyl-5'-carboxylic acid (4-iodo-3-methyl-phenyl)-amide A suspension of 5'-(4-iodo-3-methyl-phenylcarbamoyl)-3,4,5,6-tetrahydro-2H-[1,4]bipyridinyl-4-carboxylic acid (50 mg, 0.11 mmol) in CH$_2$Cl$_2$ (5 mL) was treated with EDCI (60 mg, 0.31 mmol), t-butyl sulfonamide (18 mg, 0.13 mmol) and a catalytic amount of DMAP. After stirring at rt overnight the mixture was partitioned between CH$_2$Cl$_2$ and water. The CH$_2$Cl$_2$ layer was then collected and evaporated. The product was isolated after a purification with a silica gel column and 2-5% MeOH in CH$_2$Cl$_2$ and a precipitation out of warm CH$_2$Cl$_2$ with excess of hexanes (15 mg, Yield: 24%). HRMS m/z calcd for C23H29N4O4SI [M+H]$^+$: 585.1027. Found: 585.1032.

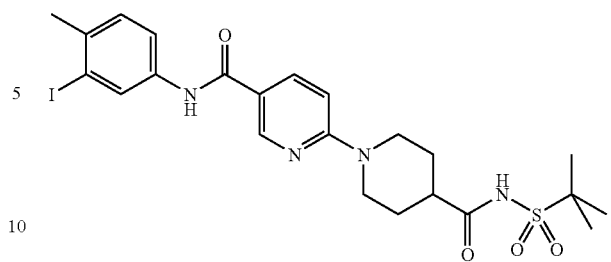

Example 87

4-(2-Methyl-propane-2-sulfonylaminocarbonyl)-3,4,5,6-tetrahydro-2H-[1,2']bipyridinyl-5'-carboxylic acid (3-iodo-4-methyl-phenyl)-amide 4-(2-Methyl-propane-2-sulfonylaminocarbonyl)-3,4,5,6-tetrahydro-2H-[1,2']bipyridinyl-5'-carboxylic acid (3-iodo-4-methyl-phenyl)-amide was prepared from 5'-(3-Iodo-4-methyl-phenylcarbamoyl)-3,4,5,6-tetrahydro-2H-[1,2']bipyridinyl-4-carboxylic acid and t-butyl sulfonamide in a manner similar to the one described in the synthesis of 4-(2-Methyl-propane-2-sulfonylaminocarbonyl)-3,4,5,6-tetrahydro-2H-[1,4]bipyridinyl-5'-carboxylic acid (4-iodo-3-methyl-phenyl)-amide. The product was isolated after a silica gel column purification with 2-5% MeOH in CH$_2$Cl$_2$. HRMS m/z calcd for C23H29N4O4SI [M+H]$^+$: 585.1027. Found: 585.1027.

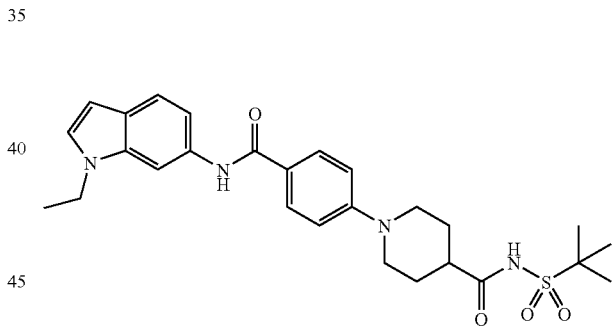

Example 88

N-(1-Ethyl-1H-indol-6-yl)-4-[4-(2-methyl-propane-2-sulfonylaminocarbonyl)-piperidin-1-yl]-benzamide N-(1-Ethyl-1H-indol-6-yl)-4-[4-(2-methyl-propane-2-sulfonylaminocarbonyl)-piperidin-1-yl]-benzamide was prepared form 1-[4-(1-ethyl-1H-indol-6-ylcarbamoyl)-phenyl]-piperidine-4-carboxylic acid and t-butyl sulfonamide in a manner similar to the one described in the synthesis of 4-(2-methyl-propane-2-sulfonylaminocarbonyl)-3,4,5,6-tetrahydro-2H-[1,2']bipyridinyl-5'-carboxylic acid (4-iodo-3-methyl-phenyl)-amide. The product was isolated after a silica gel column purification with 50-100% Et$_2$O in hexanes to 50-100% EtOAc in hexane gradient. HRMS m/z calcd for C27H34N4O4S [M+H]$^+$: 511.2374. Found: 511.2372.

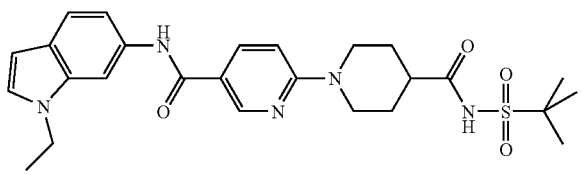

Example 89

4-(2-Methyl-propane-2-sulfonylaminocarbonyl)-3,4,
5,6-tetrahydro-2H-[1,2']bipyridinyl-5'-carboxylic
acid (1-ethyl-1,1-indol-6-yl)-amide 4-Methyl-propane-2-sulfonylaminocarbonyl)-3,4,5,6-tetrahydro-2H-[1,2']bipyridinyl-5'-carboxylic acid (1-ethyl-1H-indol-6-yl)-amide was synthesized by the ECU coupling of 5"-ethyl-1H-indol-6-ylcarbamoyl)-3,4,5,6-tetrahydro-2H-[1,2']bipyridinyl-4-carboxylic acid (prepared by the hydrolysis of 5'-(1-ethyl-1H-indol-6-ylcarbamoyl)-3,4,5,6-tetrahydro-2H-[1,2']bipyridinyl-4-carboxylic acid ethyl ester with LiOH monohydrate as described in the synthesis of 5'44-iodo-3-methyl-phenylcarbamoyl)-3,4,5,6-tetrahydro-2H-[1,2']bipyridinyl-4-carboxylic acid above.) with t-butyl sulfonamide in a manner similar to the one described in the synthesis of 442-methyl-propane-2-sulfonylaminocarbonyl)-3,4,5,6-tetrahydro-2H-[1,2']bipyridinyl-5'-carboxylic acid (4-iodo-3-methyl-phenyl)-amide. LCMS calcd for C26H33N5O4S (m/e) 511, obsd 512 (M+H).

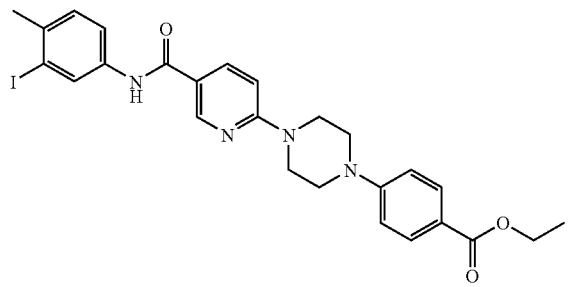

Example 90

4-{4-[5-(3-Iodo-4-methyl-phenylcarbamoyl)-pyridin-2-yl]-piperazin-1-yl}-benzoic acid ethyl ester A solution of 6-chloro-N-(3-iodo-4-methyl-phenyl)-nicotinamide (50 mg, 0.13 mmol), a catalytic amount of DMAP, diisopropylethyl amine (0.07 mL, 0.41 mmol), 4-(piperazin-1-yl)-benzoic acid ethyl ester (94 mg, 0.41 mmol) in 5 mL in dioxane was heated at 120° C. in a sealed tube for about 23 h. The reaction mixture was cooled, followed addition of another portion of 4-(piperazin-1-yl)-benzoic acid ethyl ester (94 mg, 0.41 mmol) and diisopropyl ethyl amine (0.07 mL, 0.41 mmol) and the mixture was re-heated at 120° C. for 3 more days. The reaction mixture was then cooled and partitioned between EtOAc and aq. saturated Na₂CO₃. The organic layer was then collected, dried over Na₂SO₄ filtered and concentrated. The residue was chromatographed with a silica gel column and 20-40% EtOAc in hexanes to afford the product (23 mg. Yield: 65%). HRMS m/z calcd for C26H27N4O3I [M+H]: 571.1201. Found: 571.1197.

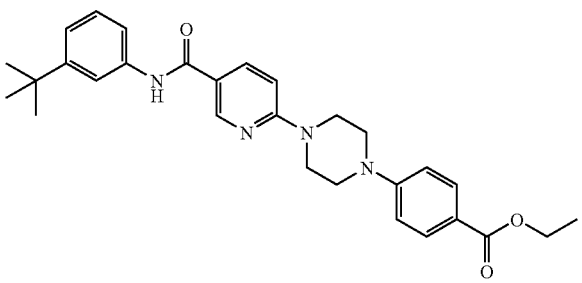

Example 91

4-{4-[5-(3-tert-Butyl-phenylcarbamoyl)-pyridin-2-yl]-piperazin-1-yl}-benzoic acid ethyl ester 4-{4-[5-(3-tert-Butyl-phenylcarbamoyl)-pyridin-2-yl]-piperazin-1-yl}-benzoic acid ethyl ester was prepared from N-(3-tert-butyl-phenyl)-6-chloro-nicotinamide and 4-(piperazin-1-yl)-benzoic acid ethyl ester following a method similar to the one described in the synthesis of 4-{4-[5-(3-iodo-4-methyl-phenylcarbamoyl)-pyridin-2-yl]-piperazin-1-yl}-benzoic acid ethyl ester above. The product was isolated after silica gel column chromatography with 20-50% EtOAc in hexanes gradient. HRMS m/z calcd for C29H34N4O3 [M+H]⁺: 487.2704. Found: 48.2701.

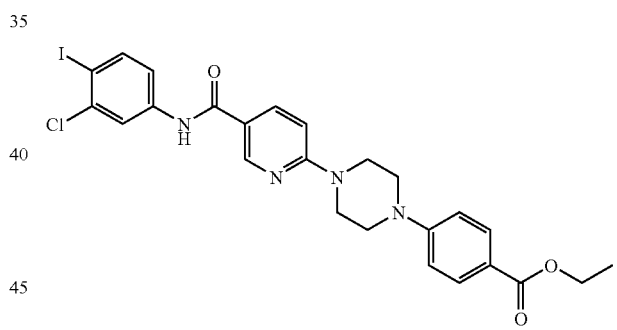

Example 92

4-{4-[5-(3-Chloro-4-iodo-phenylcarbamoyl)-pyridin-2-yl]-piperazin-1-yl}-benzoic acid ethyl ester 4-{4-[5-(3-Chloro-4-iodo-phenylcarbamoyl)-pyridin-2-yl]-piperazin-1-yl}-benzoic acid ethyl ester was prepared from 6-chloro-N-(3-chloro-4-Iodo-phenyl)-nicotinamide and 4-(piperazin-1-yl)-benzoic acid ethyl ester following a method similar to the one described in the synthesis of 4-{4-[5-(3-iodo-4-methyl-phenylcarbamoyl)-pyridin-2-yl]-piperazin-1-yl}-benzoic acid ethyl ester above. HRMS m/z calcd for C25H24N4O3ClI [M+H]⁺: 591.0655. Found: 591.0657.

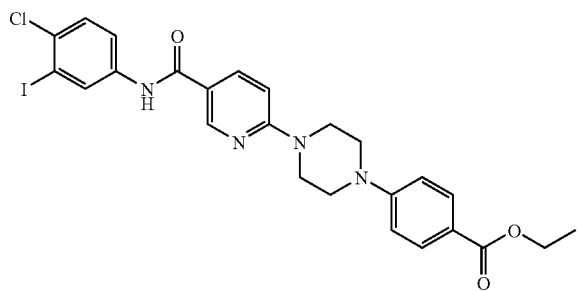

Example 93

4-{4-[5-(4-Chloro-3-iodo-phenylcarbamoyl)-pyridin-2-yl]-piperazin-1-yl}-benzoic acid ethyl ester 4-{4-[5-(4-Chloro-3-iodo-phenylcarbamoyl)-pyridin-2-yl]-piperazin-1-yl}-benzoic acid ethyl ester was prepared from 6-chloro-N-(4-chloro-3-iodo-phenyl)-nicotinamide and 4-(piperazin-1-yl)-benzoic acid ethyl ester following a method similar to the one described in the synthesis of 4-{4-[5-(3-iodo-4-methyl-phenylcarbamoyl)-pyridin-2-yl]-piperazin-1-yl}-benzoic acid ethyl ester above. The product was isolated after suspension in small volume of EtOAc and filtration. HRMS m/z calcd for C25H24N4O3ClI [M+H]+: 591.0655. Found: 591.0655.

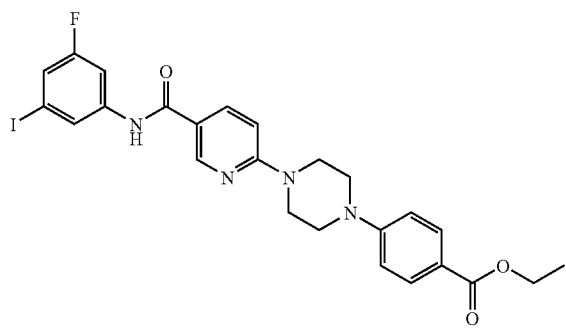

Example 94

4-{4-[5-(3-Fluoro-5-iodo-phenylcarbamoyl)-pyridin-2-yl]-piperazin-1-yl}-benzoic acid ethyl ester 4-{4-[5-(3-Fluoro-5-iodo-phenylcarbamoyl)-pyridin-2-yl]-piperazin-1-yl}-benzoic acid ethyl ester was prepared from 6-chloro-N-(3-fluoro-5-Iodo-phenyl)-nicotinamide and 4-(piperazin-1-yl)-benzoic acid ethyl ester following a method similar to the one described in the synthesis of 4-{4-[5-(3-iodo-4-methyl-phenylcarbamoyl)-pyridin-2-yl]-piperazin-1-yl}-benzoic acid ethyl ester above. The product was isolated after suspension in small volume of EtOAc filtration and a wash with CH3CN. HRMS m/z calcd for C25H24N4O3FI [M+H]+: 575.0950. Found: 575.0947.

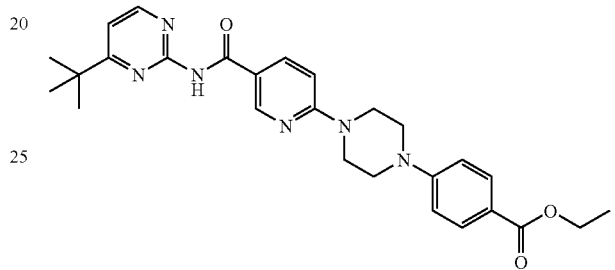

Example 95

4-{4-[5-(4-tert-Butyl-pyrimidin-2-ylcarbamoyl)-pyridin-2-yl]-piperazin-1-yl}-benzoic acid ethyl ester 4-{4-[5-(4-tert-Butyl-pyrimidin-2-ylcarbamoyl)-pyridin-2-yl]-piperazin-1-yl}-benzoic acid ethyl ester was prepared from N-(4-tert-butyl-pyrimidin-2-yl)-6-chloro-nicotinamide and 4-(piperazin-1-yl)-benzoic acid ethyl ester following a method similar to the one described in the synthesis of 4-{4-[5-(3-iodo-4-methyl-phenylcarbamoyl)-pyridin-2-yl]-piperazin-1-yl}-benzoic acid ethyl ester above. The product was isolated after silica gel column with 30-100% EtOAc in hexanes. HRMS m/z calcd for C27H32N6O3 [M+H]+: 489.2609. Found: 489.2609.

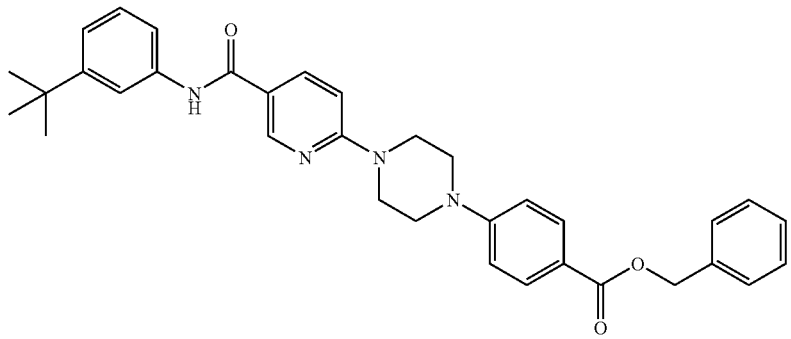

Example 96

4-{4-[5-(3-tert-Butyl-phenylcarbamoyl)-pyridin-2-yl]-piperazin-1-yl}-benzoic acid benzyl ester 4-{4-[5-(3-tert-Butyl-phenylcarbamoyl)-pyridin-2-yl]-piperazin-1-yl}-benzoic acid benzyl ester was prepared from N-(3-tent-butyl-phenyl)-6-chloro-nicotinamide and 4-piperazin-1-yl-benzoic acid benzyl ester following a method similar to the one described in the synthesis of 4-{4-[5-(3-iodo-4-methyl-phenylcarbamoyl)-pyridin-2-yl]-piperazin-1-yl}-benzoic acid ethyl ester above. The product was isolated after silica gel column chromatography with 20-50% EtOAc in hexanes gradient. HRMS m/z calcd for C34H36N4O3 [M+H]⁺: 549.2860. Found: 549.2858

Example 98

4-{4-[5-(1-Ethyl-1H-indol-6-ylcarbamoyl)-pyridin-2-yl]-piperazin-1-yl}-benzoic acid benzyl ester 4-{4-[5-(1-Ethyl-1H-indol-6-ylcarbamoyl)-pyridin-2-yl]-piperazin-1-yl}-benzoic acid benzyl ester was prepared from 6-chloro-N-(1-ethyl-1H-indol-6-yl)-nicotinamide and 4-piperazin-1-yl-benzoic acid benzyl ester following a method similar to the one described in the synthesis of 4-{4-[5-(3-iodo-4-methyl-phenylcarbamoyl)-pyridin-2-yl]-piperazin-1-yl}-benzoic acid ethyl ester above. The product was isolated after silica gel column chromatography with 20-60% EtOAc in hexanes gradient. HRMS m/z calcd for C34H33N5O3 [M+H]⁺: 560.2656. Found: 560.2656.

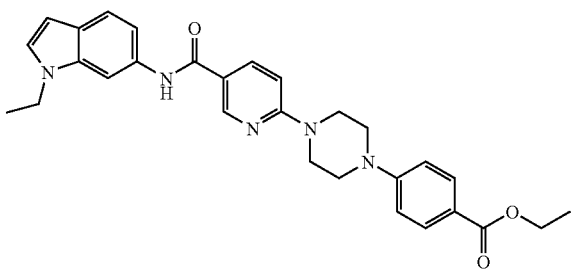

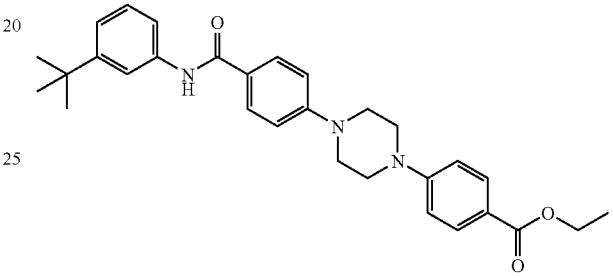

Example 97

4-{4-[5-(1-Ethyl-1H-indol-6-ylcarbamoyl)-pyridin-2-yl]-piperazin-1-yl}-benzoic acid ethyl ester 4-{4-[5-(1-Ethyl-1H-indol-6-ylcarbamoyl)-pyridin-2-yl] piperazin-1-yl}-benzoic acid ethyl ester was prepared from 6-chloro-N-(1-ethyl-1H-indol-6-yl)-nicotinamide and 4-(piperazin-1-yl)-benzoic acid ethyl ester following a method similar to the one described in the synthesis of 4-{4-[5-(3-iodo-4-methyl-phenylcarbamoyl)-pyridin-2-yl]-piperazin-1-yl}-benzoic acid ethyl ester above. The product was isolated after silica gel column chromatography with 20-50% EtOAc in hexanes gradient. HRMS m/z calcd for C29H31N5O3 [M+H]⁺: 498.2500. Found: 498.2501.

Example 99

4-{4-[4-(3-tert-Butyl-phenylcarbamoyl)-phenyl]-piperazin-1-yl}-benzoic acid ethyl ester A mixture of N-(3-tert-butyl-phenyl)-4-piperazin-1-yl-benzamide (150 mg, 0.44 mmol), 4-fluoro ethyl benzoate (370 mg, 2.22 mmol), diisopropyl ethyl amine (3 mL) and a catalytic amount of DMAP in DMSO (5 mL) was stirred at 120° C. in a sealed tube for 67 h. The mixture was then cooled and partitioned between EtOAc and water. The organic layer was separated, dried over Na₂SO₄, filtered and concentrated. The residue was purified with a silica gel column and 0-20% EtOAc in CH₂Cl₂ to afford the product (80 mg, Yield: 37%). HRMS m/z calcd for C30H35N3O3 [M+H]⁺: 486.2751. Found: 486.2751.

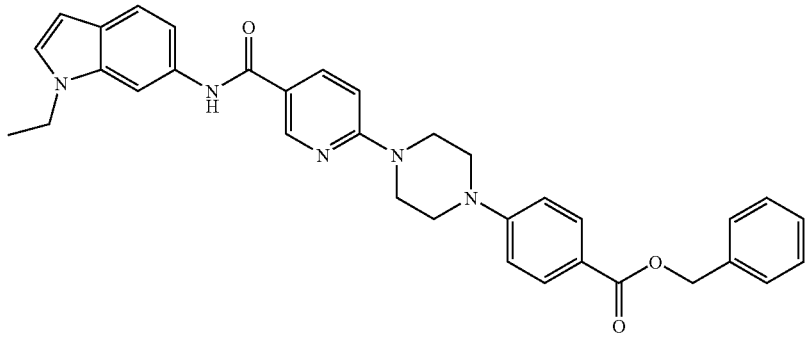

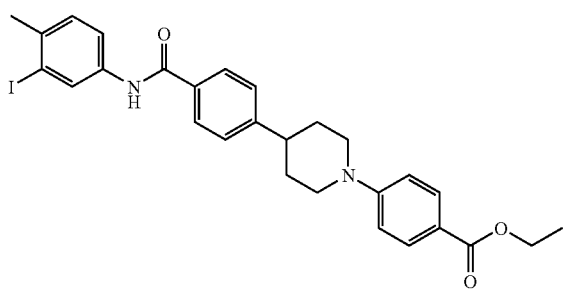

Example 100

4-{4-[4-(3-Iodo-4-methyl-phenylcarbamoyl)-phenyl]-piperidin-1-yl}-benzoic acid ethyl ester N-Boc-4-(4-carboxyphenyl)piperidine (200 mg, 0.66 mmol) and 3-iodo-4-methyl aniline (153 mg, 0.72 mmol) in DCM (10 mL) was treated with EDCI (380 mg, 1.98 mmol) at rt. After stirring for 48 hr at rt the reaction mixture was partitioned between EtOAc and water. The EtOAc layer was collected, concentrated and the residue was chromatographed on a silica gel column with a 0-30% EtOAc in hexanes to afford the corresponding intermediate 4-[4-(3-Iodo-4-methyl-phenylcarbamoyl)-phenyl]-piperidine-1-carboxylic acid tert-butyl ester. This intermediate was then dissolved in a 30% TFA in $CH_2Cl_2$ mixture (10 mL). Upon consumption of the starting material, as judged by TLC, the solution was partitioned between EtOAc and water. The water layer was basified to pH 12 with solid NaOH. The organic layer was then collected, dried over $Na_2SO_4$, filtered and concentrated to a residue that without further delay was dissolved in DMSO (5 mL). The mixture was then treated with 4-fluoro ethyl benzoate (550 mg, 3.28 mmol), diisopropyl ethyl amine (3 mL) and a catalytic amount of DMAP and heated at 120° C. in a sealed tube for 4 days. The reaction mixture was then cooled, partitioned between EtOAc and water. The EtOAc layer was collected dried over $Na_2SO_4$ filtered and concentrated to a solid that after suspension in $CH_2Cl_2$ and filtration afforded the product (100 mg, Yield: 53%). HRMS m/z calcd for C28H29N2O3I $[M+H]^+$: 569.1296. Found: 569.1294.

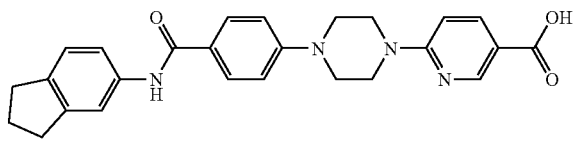

Example 101

6-{4-[4-(Indan-5-ylcarbamoyl)-phenyl]-piperazin-1-yl}-nicotinic acid

To a solution of N-indan-5-yl-4-piperazin-1-yl-benzamide (80 mg) and 2-chloropyridine-5-carboxylic acid ethyl ester (220 mg) in THF (4 mL) was added diisopropylethylamine (0.1 mL). The solution was heated in a microwave at 170° C. for 2 hrs. The crystalline precipitate was filtered and washed with THF to give 6-{4-[4-(indan-5-ylcarbamoyl)-phenyl]-piperazin-1-yl}-nicotinic acid ethyl ester (62 mg, Yield: 53%). LCMS calc for C28H30N4O3 (m/e) 470, obsd 471 (M+H).

The above ethyl ester (47 mg, 0.10 mmol) was suspended in THF (6 mL) and methanol (6 mL), Then lithium hydroxide solution. (0.5 N, 1 mL) was added. The mixture was refluxed for 8 hrs and then evaporated. The residue was dissolved in hot methanol (35 mL) and the solution was cooled to room temperature before aqueous hydrochloric acid (1N, 0.55 mL) was added. The white crystalline material was filtered and washed with methanol to give 6-{4-[4-(indan-5-ylcarbamoyl)-phenyl]-piperazin-1-yl}-nicotinic acid (38 mg, Yield: 85%). LCMS calc for C26H26N4O3 (m/e) 442, obsd 443 (M+H).

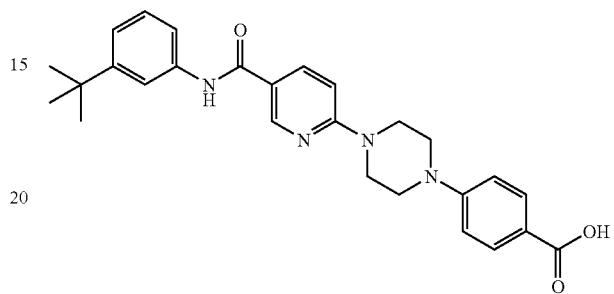

Example 102

4-{4-[5-(3-tert-Butyl-phenylcarbamoyl)-pyridin-2-yl]-piperazin-1-yl}-benzoic acid 4-{4-[5-(3-tert-Butyl-phenylcarbamoyl)-pyridin-2-yl]-piperazin-1-yl}-benzoic acid ethyl ester (50 mg, 0.11 mmol) in THF (10 mL) and water (2 mL) was treated with LiOH monohydrate (8.6 mg, 0.22 mmol). After stirring at rt for 4 h the mixture was treated with another portion of LiOH monohydrate (9 mg, 0.22 mmol) and the mixture was stirred at 50° C. for 16 h. The mixture was then cooled and partitioned between EtOAc and water. The acidity of the water layer was adjusted to pH 5 with 1N aqueous HCl. The water layer was extracted twice more with EtOAc and the combined EtOAc layer was dried, filtered and concentrated. The residue was chromatographed on a silica gel column with 0-3% MeOH in $CH_2Cl_2$ gradient to afford the product (6 mg; Yield: 13%). HRMS m/z calcd for C27H30N4O3 $[M+H]^+$: 459.2391. Found: 459.2388.

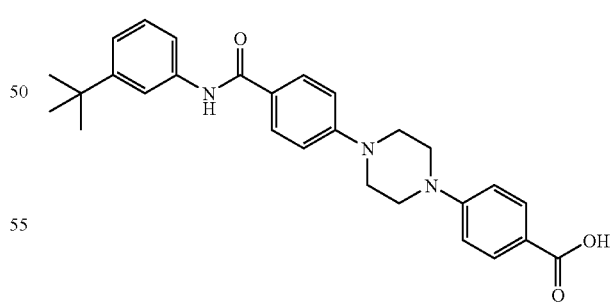

Example 103

4-{4-[4-(3-tert-Butyl-phenylcarbamoyl)-phenyl]-piperazin-1-yl}-benzoic acid

4-{4-[4-(3-tert-Butyl-phenylcarbamoyl)-phenyl]-piperazin-1-yl}-benzoic acid was prepared from the LiOH monohydrate hydrolysis of 4-{4-[4-(3-tert-butyl-phenylcarbamoyl)-phenyl}-piperazin-1-yl]-benzoic acid ethyl ester following a method similar to the one described in the synthesis of 4-{4-[5-(3-tert-butyl-phenylcarbamoyl)-pyridin-2-yl]-piperazin-1-yl}-benzoic acid above. HRMS m/z calcd for C28H31N3O3 [M+H]+: 458.2438. Found: 458.2439.

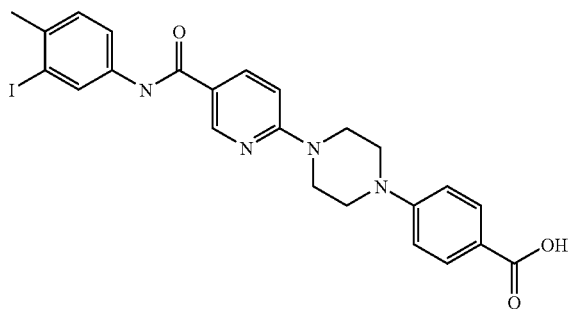

Example 104

4-{4-[5-(3-Iodo-4-methyl-phenylcarbamoyl)-pyridin-2-yl]-piperazin-1-yl}-benzoic acid 4-{4-[5-(3-Iodo-4-methyl-phenylcarbamoyl)-pyridin-2-yl]-piperazin-1-yl}-benzoic acid was prepared by the hydrolysis of 4-{4-[5-(3-iodo-4-methyl-phenylcarbamoyl)-pyridin-2-yl]-piperazin-1-yl}-benzoic acid ethyl ester with LiOH monohydrate in manner similar to the one described in the synthesis of 4-{4-[5-(3-tert-butyl-phenylcarbamoyl)-pyridin-2-yl]-piperazin-1-yl}-benzoic acid, above. The product was isolated after a silica gel column chromatography with a 0-5% MeOH in $CH_2Cl_2$ to 0-100% DMF in $CH_2Cl_2$ gradient. HRMS m/z calcd for C24H23N4O3I [M+H]+: 543.0888. Found: 543.0886.

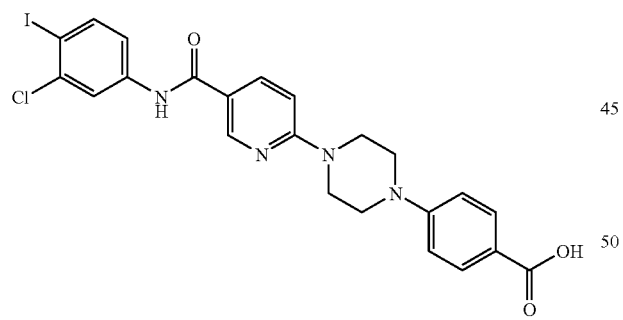

Example 105

4-{4-[5-(3-Chloro-4-iodo-phenylcarbamoyl)-pyridin-2-yl]-piperazin-1-yl}-benzoic acid 4-{4-[5-(3-Chloro-4-iodo-phenylcarbamoyl)-pyridin-2-yl]-piperazin-1-yl}-benzoic acid was prepared by the hydrolysis of 4-{4-[5-(3-chloro-4-iodo-phenylcarbamoyl)-pyridin-2-yl]-piperazin-1-yl}-benzoic acid ethyl ester with LiOH monohydrate in manner similar to the one described in the synthesis of 4-{4-[5-(3-tert-butyl-phenylcarbamoyl)-pyridin-2-yl]-piperazin-1-yl}-benzoic acid, above. The product was obtained after suspension in small volume of EtOAc and filtration. HRMS m/z calcd for C23H20N4O3ClI [M+H]+: 563.0342. Found: 563.0343.

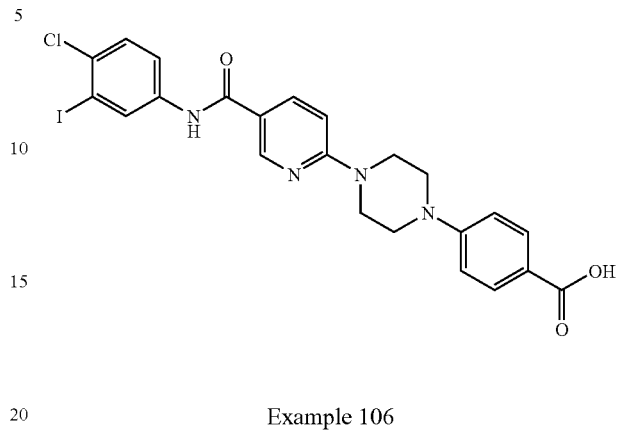

Example 106

4-{4-[5-(4-Chloro-3-iodo-phenylcarbamoyl)-pyridin-2-yl]-piperazin-1-yl}-benzoic acid 4-{4-[5-(4-Chloro-3-iodo-phenylcarbamoyl)-pyridin-2-yl]-piperazin-1-yl}-benzoic acid was prepared by the hydrolysis of 4-{4-[5-(4-chloro-3-iodo-phenylcarbamoyl)-pyridin-2-yl]-piperazin-1-yl}-benzoic acid ethyl ester with LiOH monohydrate in manner similar to the one described in the synthesis of 4-{4-[5-(3-tert-butyl-phenylcarbamoyl)-pyridin-2-yl]-piperazin-1-yl}-benzoic acid, above. The product was obtained after suspension in small volume of EtOAc and filtration. HRMS m/z calcd for C23H20N4O3ClI [M+H]+: 563.0342. Found: 563.0343.

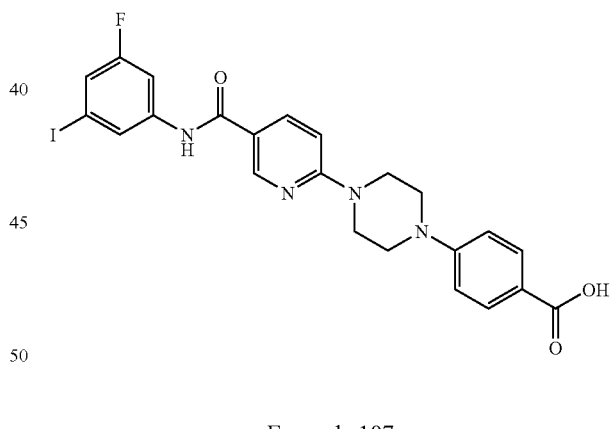

Example 107

4-{4-[5-(3-Fluoro-5-iodo-phenylcarbamoyl)-pyridin-2-yl]-piperazin-1-yl}-benzoic acid 4-{4-[5-(3-Fluoro-5-iodo-phenylcarbamoyl)-pyridin-2-yl]-piperazin-1-yl}-benzoic acid was prepared by the hydrolysis of 4-{4-[5-(3-fluoro-5-iodo-phenylcarbamoyl)-pyridin-2-yl]-piperazin-1-yl}-benzoic acid ethyl ester with LiOH monohydrate in manner similar to the one described in the synthesis of 4-{4-[5-(3-tert-butyl-phenylcarbamoyl)-pyridin-2-yl]-piperazin-1-yl}-benzoic acid, above. The product was obtained after suspension in small volume of EtOAc, filtration and a wash with $CH_3CN$. HRMS m/z calcd for C23H20N4O3FI [M+H]+: 547.0637. Found: 547.0634.

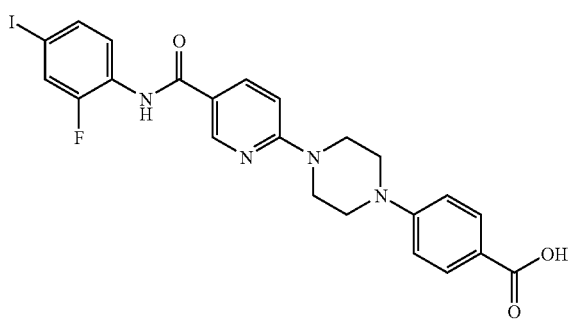

Example 108

4-{4-[5-(2-Fluoro-4-iodo-phenylcarbamoyl)-pyridin-2-yl]-piperazin-1-yl}-benzoic acid 6-Chloro-N-(2-fluoro-4-iodo-phenyl)-nicotinamide (80 mg, 0.22 mmol), diisopropyl ethyl amine (0.23 mL, 1.28 mmol), 4-(piperazin-1-yl)-benzoic acid ethyl ester (300 mg, 1.28 mmol) and a catalytic amount of DMAP in dioxane (5 mL) in a sealed tube was heated at 120° C. until TLC showed consumption of the limiting reagent. The mixture was then cooled and partitioned between EtOAc and water. The EtOAc layer was collected, dried over $Na_2SO_4$, filtered and concentrated to a small volume. The solid formed filtered and washed with $CH_3CN$ to afford the corresponding intermediate ethyl ester that was then dissolved in a 5:1 mixture of THF and water (6 mL). This mixture was treated with LiOH monohydrate (21 mg, 0.49 mmol) and heated at 65° C. in a sealed tube for 4 days. The mixture was then cooled and partitioned between EtOAc and water. The acidity of the water layer was adjusted to pH 6 with 1 N eq. HCl. The organic layer was then collected dried over $Na_2SO_4$ filtered and concentrated to a small volume. The solid formed, was filtered and washed with $CH_3CN$ to afford the product. HRMS m/z calcd for C23H20N4O3FI [M+H]$^+$: 547.0637. Found: 547.0636.

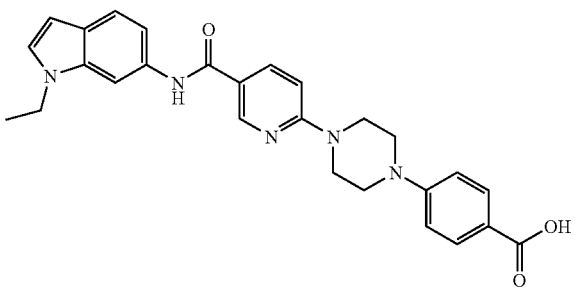

Example 109

4-{4-[5-(1-Ethyl-1H-indol-6-ylcarbamoyl)-pyridin-2-yl]-piperazin-1-yl}-benzoic acid A mixture of 4-{4-[5-(1-ethyl-1H-indol-6-ylcarbamoyl)-pyridin-2-yl]-piperazin-1-yl}-benzoic acid benzyl ester (100 mg, 0.18 mmol), 10% Pd/C (50 mg) in a 1:1 mixture of EtOH and EtOAc (50 mL) was hydrogenated under 1 atm of hydrogen for 2 h. The mixture was then filtered. The solids were washed with a 1:1 mixture of THF and DMF and the combined organic layer was concentrated. The residue was passed through a silica gel plug with DMF to afford the product (85 mg; Yield: 96%). HRMS m/z calcd for C27H27N5O3I [M+H]$^+$: 70.2187. Found: 470.2184.

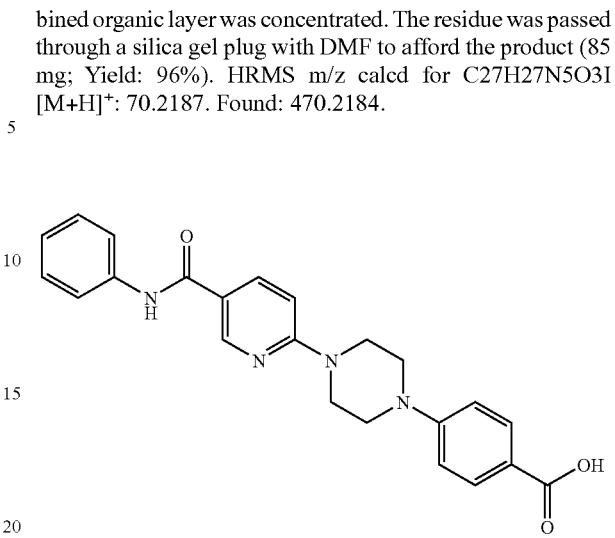

Example 110

4-[4-(5-Phenylcarbamoyl-pyridin-2-yl)-piperazin-1-yl]-benzoic acid

6-Chloro-N-phenyl-nicotinamide (50 mg, 0.22 mmol), diisopropyl ethyl amine (0.23 mL, 1.32 mmol), 4-piperazin-1-yl-benzoic acid benzyl ester (390 mg, 1.32 mmol) and a catalytic amount of DMAP in dioxane (5 mL) in a sealed tube was heated at 120° C. until TLC showed consumption of the limiting reagent. The mixture was then cooled and partitioned between EtOAc and water. The EtOAc layer was collected, dried over $Na_2SO_4$, filtered and concentrated to a small volume. Followed addition of excess of $CH_3CN$ and the mixture was then concentrated to a small volume. The solid formed was filtered, washed twice with approximately 1 mL of $CH_3CN$, air dried to afford the intermediate corresponding benzyl ester. Following dissolution of the intermediate benzyl ester in a 2:1 mixture of THF and EtOH (20 mL), the resulting mixture was treated with 10% Pd/C (47 mg) and was hydrogenated under 1 atm of hydrogen until TLC showed consumption of the starting material. Following filtration, the solids were washed with DMF and THF and the combined filtrate was evaporated. The solid obtained was suspended in hot THF, the mixture was treated with excess of hexanes and filtered to afford the product. HRMS m/z calcd for C23H22N4O3 [M+H]$^+$: 403.1765. Found: 403.1763.

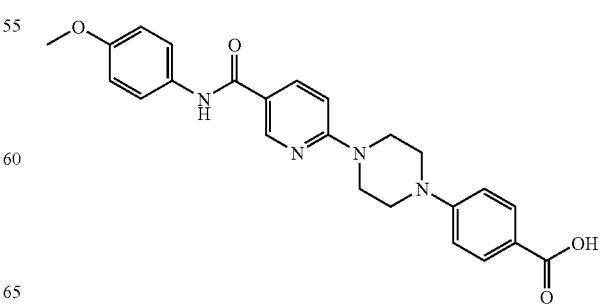

Example 111

4-{4-[5-(4-Methoxy-phenylcarbamoyl)-pyridin-2-yl]-piperazin-1-yl}-benzoic acid

4-{4-[5-(4-Methoxy-phenylcarbamoyl)-pyridin-2-yl]-piperazin-1-yl}-benzoic acid was prepared from 4-piperazin-1-yl-benzoic acid benzyl ester and 6-chloro-N-(4-methoxy-phenyl)-nicotinamide with a method similar to the one described in the synthesis of 4-[4-(5-phenylcarbamoyl-pyridin-2-yl)-piperazin-1-yl]-benzoic acid above. HRMS m/z calcd for C24H24N4O4 [M+H]$^+$: 433.1871. Found: 433.1870.

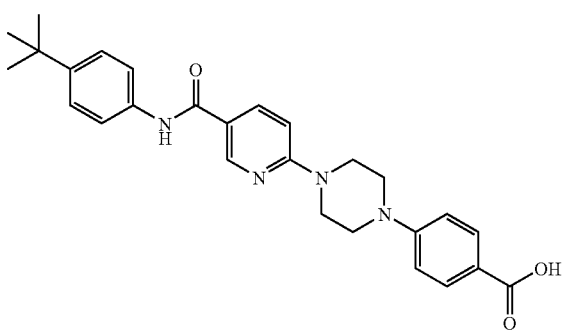

Example 112

4-{4-[5-(4-tert-Butyl-phenylcarbamoyl)-pyridin-2-yl]-piperazin-1-yl}-benzoic acid 4-{4-[5-(4-tert-Butyl-phenylcarbamoyl)-pyridin-2-yl]-piperazin-1-yl}-benzoic acid was prepared from 4-piperazin-1-yl-benzoic acid benzyl ester and N-(4-tert-butyl-phenyl)-6-chloro-nicotinamide with a method similar to the one described in the synthesis of 4-[4-(5-phenylcarbamoyl-pyridin-2-yl)-piperazin-1-yl]-benzoic acid above. HRMS m/z calcd for C27H30N4O3 [M+H]$^+$: 459.2391. Found: 459.2390.

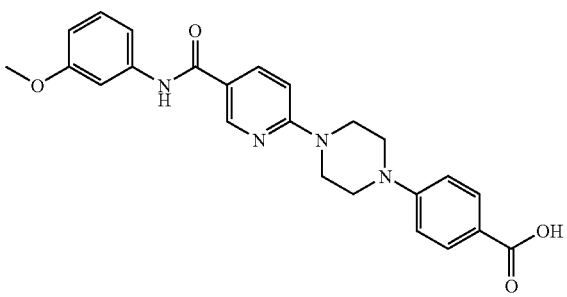

Example 113

4-{4-[5-(3-Methoxy-phenylcarbamoyl)-pyridin-2-yl]-piperazin-1-yl}-benzoic acid

4-{4-[5-(3-Methoxy-phenylcarbamoyl)-pyridin-2-yl]-piperazin-1-yl}-benzoic acid was prepared from 4-piperazin-1-yl-benzoic acid benzyl ester and 6-chloro-N-(3-methoxy-phenyl)-nicotinamide with a method similar to the one described in the synthesis of 4-[4-(5-phenylcarbamoyl-pyridin-2-yl)-piperazin-1-yl]-benzoic acid above. HRMS m/z calcd for C24H24N4O4 [M+H]$^+$: 433.1871. Found: 433.1868.

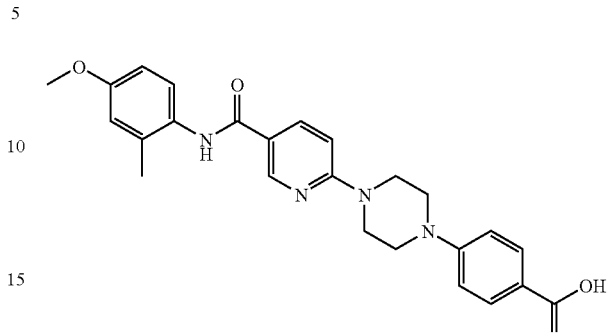

Example 114

4-{4-[5-(4-Methoxy-2-methyl-phenylcarbamoyl)-pyridin-2-yl]-piperazin-1-yl}-benzoic acid 4-{4-[5-(4-Methoxy-2-methyl-phenylcarbamoyl)-pyridin-2-yl]-piperazin-1-yl}-benzoic acid was prepared from 4-piperazin-1-yl-benzoic acid benzyl ester and 6-chloro-N-(4-methoxy-2-methyl-phenyl)-nicotinamide with a method similar to the one described in the synthesis of 4-[4-(5-phenylcarbamoyl-pyridin-2-yl)-piperazin-1-yl]-benzoic acid above. HRMS m/z calcd for C25H26N4O4 [M+H]$^+$: 447.2027. Found: 447.2027.

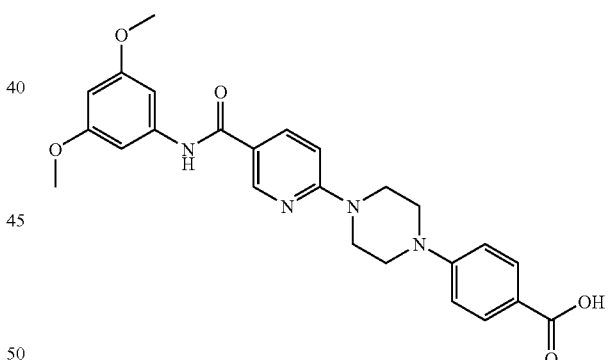

Example 115

4-{4-[5-(3,5-Dimethoxy-phenylcarbamoyl)-pyridin-2-yl]-piperazin-1-yl}-benzoic acid 4-{4-[5-(3,5-Dimethoxy-phenylcarbamoyl)-pyridin-2-yl]-piperazin-1-yl}-benzoic acid was prepared from 4-piperazin-1-yl-benzoic acid benzyl ester and 6-chloro-N-(3,5-dimethoxy-phenyl)-nicotinamide with a method similar to the one described in the synthesis of 4-[4-(5-phenylcarbamoyl-pyridin-2-yl)-piperazin-1-yl]-benzoic acid above. HRMS m/z calcd for C25H26N4O5 [M+H]$^+$: 463.1976. Found: 463.1977

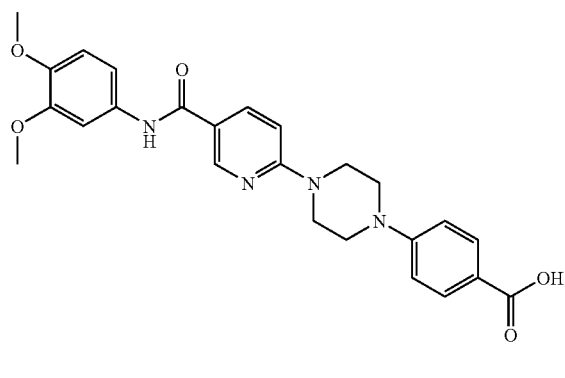

Example 116

4-{4-[5-(3,4-Dimethoxy-phenylcarbamoyl)-pyridin-2-yl]-piperazin-yl}-benzoic acid 4-{4-[5-(3,4-Dimethoxy-phenylcarbamoyl)-pyridin-2-yl]-piperazin-1-yl}-benzoic acid was prepared from 4-piperazin-1-yl-benzoic acid benzyl ester and 6-chloro-N-(3,4-dimethoxy-phenyl)-nicotinamide with a method similar to the one described in the synthesis of 4-[4-(5-phenylcarbamoyl-pyridin-2-yl)-piperazin-1-yl]-benzoic acid above. HRMS m/z calcd for C25H26N4O5 [M+H]$^+$: 463.1976. Found: 463.1976.

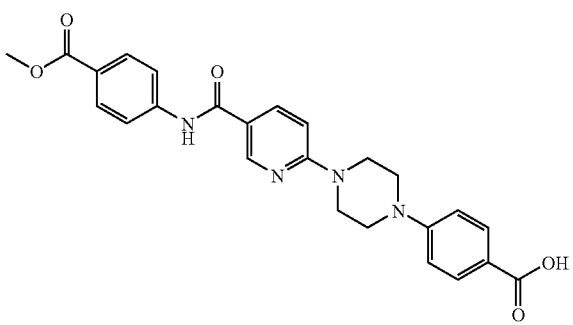

Example 117

4-{4-[5-(4-Methylester-phenylcarbamoyl)-pyridin-2-yl]-piperazin-1-yl}-benzoic acid 4-{4-[5-(4-Methylester-phenylcarbamoyl)-pyridin-2-yl]-piperazin-1-yl}-benzoic acid was prepared from 4-piperazin-1-yl-benzoic acid benzyl ester and 4-[(6-chloro-pyridine-3-carbonyl)-amino]-benzoic acid methyl ester with a method similar to the one described in the synthesis of 4-[4-(5-phenylcarbamoyl-pyridin-2-yl)-piperazin-1-yl]-benzoic acid above. HRMS m/z calcd for C25H24N4O5 [M+H]$^+$: 461.1820. Found: 461.1818.

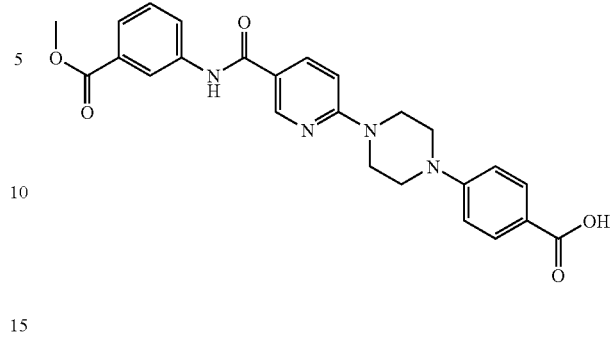

Example 118

4-{4-[5-(3-Methylester-phenylcarbamoyl)-pyridin-2-yl]-piperazin-1-yl}-benzoic acid 4-{4-[5-(3-Methylester-phenylcarbamoyl)-pyridin-2-yl]-piperazin-1-yl}-benzoic acid was prepared from 4-piperazin-1-yl-benzoic acid benzyl ester and 3-[(6-chloro-pyridine-3-carbonyl)-amino]-benzoic acid methyl ester with a method similar to the one described in the synthesis of 4-[4-(5-phenylcarbamoyl-pyridin-2-yl)-piperazin-1-yl]-benzoic acid above. HRMS m/z calcd for C25H24N4O5 [M+H]$^+$: 461.1820. Found: 461.1819.

Example 119

4-{4-[5-(3,4-Dimethyl-phenylcarbamoyl)-pyridin-2-yl]-piperazin-1-yl}-benzoic acid 4-{4-[5-(3,4-Dimethyl-phenylcarbamoyl)-pyridin-2-yl]-piperazin-1-yl}-benzoic acid was prepared from 4-piperazin-1-yl-benzoic acid benzyl ester and 6-chloro-N-(3,4-dimethyl-phenyl)-nicotinamide with a method similar to the one described in the synthesis of 4-[4-(5-phenylcarbamoyl-pyridin-2-yl)-piperazin-1-yl]-benzoic acid above. HRMS m/z calcd for C25H26N4O3 [M+H]$^+$: 431.2078. Found: 431.2078.

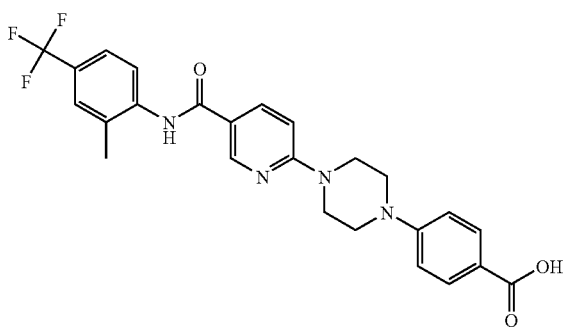

Example 120

4-{4-[5-(2-Fluoro-4-trifluoromethyl-phenylcarbamoyl)-pyridin-2-yl]-piperazin-1yl}-benzoic acid 4-{4-[5-(2-Fluoro-4-trifluoromethyl-phenylcarbamoyl)-pyridin-2-yl]-piperazin-1-yl}-benzoic acid was prepared from 4-piperazin-1-yl-benzoic acid benzyl ester and 6-chloro-N-(2-fluoro-4-trifluoromethyl-phenyl)-nicotinamide with a method similar to the one described in the synthesis of 4-[4-(5-phenylcarbamoyl-pyridin-2-yl)-piperazin-1-yl]-benzoic acid above. HRMS m/z calcd for C24H20N4O3F4 [M+H]$^+$: 489.1545. Found: 489.1543.

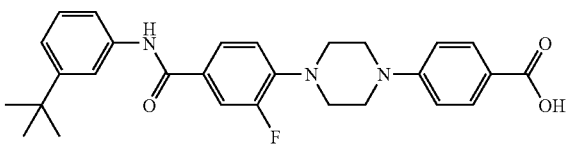

Example 121

4-{4-[4-(3-tert-Butyl-phenylcarbamoyl)-2-fluoro-phenyl]-piperazin-1-yl}-benzoic acid To a N-(3-tert-butyl-phenyl)-3-fluoro-4-piperazin-1-yl-benzamide (0.15 mmol) solution in dioxane was added 4-bromo-benzoic acid (0.195 mmol), NaOtBu (0.45 mmol), Xantphos (0.03 mmol) and Pd$_2$dba$_3$ (0.009 mmol). The reaction vial was purged with Ar, sealed, and heated at 85° C. overnight. The reaction was worked up by diluting with methanol adding an excess of NH$_4$Cl, and passing through a plug of silica gel (1 g) and eluting with methanol. The methanol fraction was concentrated. The residue suspended in DMSO, filtered, and purified by reverse phase liquid chromatography with increasing concentrations of CH$_3$CN in water yielding the product 4-{4-[4-(3-tert-butyl-phenylcarbamoyl)-2-fluoro-phenyl]-piperazin-1-yl}-benzoic acid. LCMS calcd for C28H30FN3O3 (m/e) 475, obsd 476 (M+H).

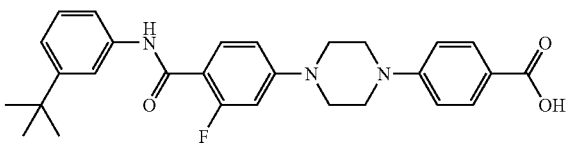

Example 122

4-{4-[4-(3-tert-Butyl-phenylcarbamoyl)-3-fluoro-phenyl]-piperazin-1-yl}-benzoic acid 4-{4-[4-(3-tert-Butyl-phenylcarbamoyl)-3-fluoro-phenyl]-piperazin-1-yl}-benzoic acid was synthesized by the coupling of N-(3-tert-butyl-phenyl)-2-fluoro-4-piperazin-1-yl-benzamide and 4-bromo benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C28H30FN3O3 (m/e) 475, obsd 476 (M+H).

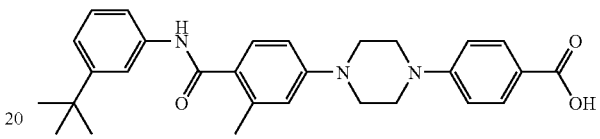

Example 123

4-{4-[4-(3-tert-Butyl-phenylcarbamoyl)-3-methyl-phenyl]-piperazin-1-yl}-benzoic acid 4-{4-[4-(3-tert-Butyl-phenylcarbamoyl)-3-methyl-phenyl]-piperazin-1-yl}-benzoic acid was synthesized by the coupling of N-(3-tert-butyl-phenyl)-2-methyl-4-piperazin-1-yl-benzamide and 4-bromo benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C29H33N3O3 (m/e) 471, obsd 472 (M+H).

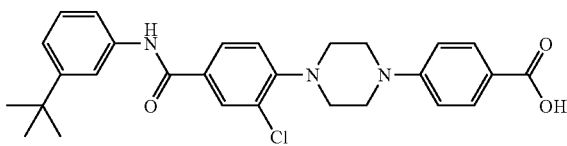

Example 124

4-{4-[4-(3-tert-Butyl-phenylcarbamoyl)-2-chloro-phenyl]-piperazin-1-yl}-benzoic acid 4-{4-[4-(3-tert-Butyl-phenylcarbamoyl)-2-chloro-phenyl]-piperazin-1-yl}-benzoic acid was synthesized by the coupling of N-(3-tert-Butyl-phenyl)-3-chloro-4-piperazin-1-yl-benzamide and 4-bromo benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C28H30ClN3O3 (m/e) 491, obsd 490 (M−H)

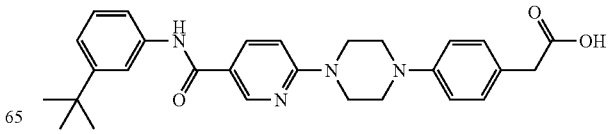

Example 125

(4-{4-[5-(3-tert-Butyl-phenylcarbamoyl)-pyridin-2-yl]-piperazin-1-yl}-phenyl)-acetic acid (4-{4-[5-(3-tert-Butyl-phenylcarbamoyl)-pyridin-2-yl]-piperazin-1-yl}-phenyl)-acetic acid was synthesized from N-(3-tert-butyl-phenyl)-6-piperazin-1-yl-nicotinamide and 4-bromo phenyl acetic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C28H32N4O3 (m/e) 472, obsd 473 (M+H).

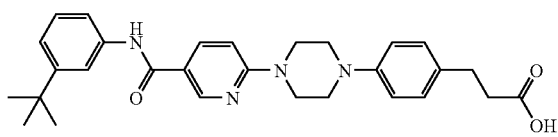

Example 126

(4-{4-[5-(3-tert-Butyl-phenylcarbamoyl)-pyridin-2-yl]-piperazin-1-yl}-phenyl)-propionic acid (4-{4-[5-(3-tert-Butyl-phenylcarbamoyl)-pyridin-2-yl]-piperazin-1-yl}-phenyl)-propionic acid was synthesized from N-(3-tert-butyl-phenyl)-6-piperazin-1-yl-nicotinamide and 4-bromo phenyl propionic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C29H34N4O3 (m/e) 486, obsd 487 (M+H).

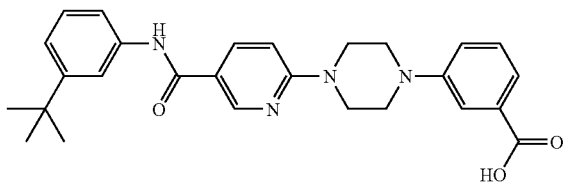

Example 127

3-{4-[5-(3-tert-Butyl-phenylcarbamoyl)-pyridin-2-yl]-piperazin-1-yl}-benzoic acid 3-{4-[5-(3-tert-Butyl-phenylcarbamoyl)-pyridin-2-yl]-piperazin-1-yl}-benzoic acid was synthesized from N-(3-tert-butyl-phenyl)-6-piperazin-1-yl-nicotinamide and 3-bromo benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C27H30N4O3 (m/e) 458, obsd 459 (M+H).

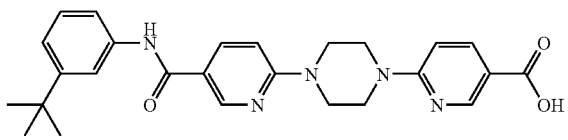

Example 128

6-{4-[5-(3-tert-Butyl-phenylcarbamoyl)-pyridin-2-yl]-piperazin-1-yl}-nicotinic acid 6-{4-[5-(3-tert-Butyl-phenylcarbamoyl)-pyridin-2-yl]-piperazin-1-yl}-nicotinic acid was synthesized from N-(3-tert-butyl-phenyl)-6-piperazin-1-yl-nicotinamide and 6-chloro nicotinic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C26H29N5O3 (m/e) 459, obsd 460 (M+H).

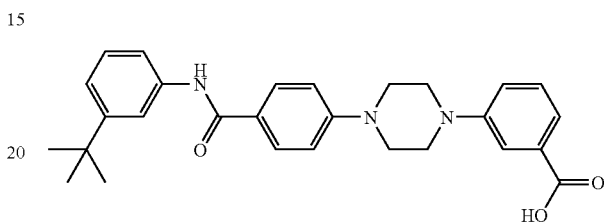

Example 129

3-{4-[4-(3-tert-Butyl-phenylcarbamoyl)-phenyl]-piperidin-1-yl}-benzoic add

3-{4-[4-(3-tert-Butyl-phenylcarbamoyl)-phenyl]-piperidin-1-yl}-benzoic acid was synthesized from N-(3-tert-butyl-phenyl)-4-piperidin-4-yl-benzamide and 3-bromo-benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C29H32N2O3 (m/e) 456, obsd 457 (M+H).

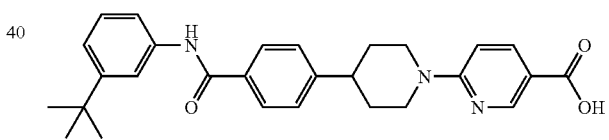

Example 130

6-{4-[4-(3-tert-Butyl-phenylcarbamoyl)-phenyl]-piperazin-1-yl}-nicotinic acid

6-{4-[4-(3-tert-Butyl-phenylcarbamoyl)-phenyl]-piperazin-1-yl}-nicotinic acid was synthesized from N-(3-tert-butyl-phenyl)-4-piperidin-4-yl-benzamide and 6-chloro-nicotinic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C28H31N3O3 (m/e) 457, obsd 458 (M+H).

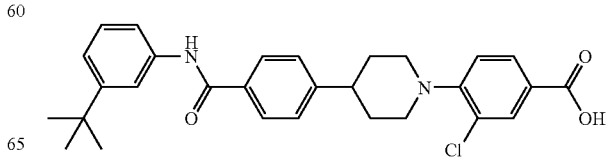

Example 131

4-{4-[4-(3-tert-Butyl-phenylcarbamoyl)-phenyl]-piperidin-1-yl}-3-chloro-benzoic acid 4-{4-[4-(3-tert-Butyl-phenylcarbamoyl)-phenyl]-piperidin-1-yl}-3-chloro-benzoic acid was synthesized from N-(3-tert-butyl-phenyl)-4-piperidin-4-yl-benzamide and 4-bromo-3-chloro-benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C29H31ClN2O3 (m/e) 490, obsd 491 (M+H).

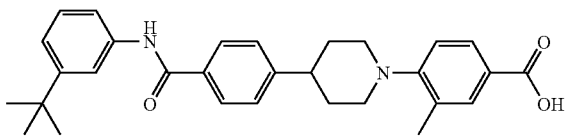

Example 132

4-{4-[4-(3-tert-Butyl-phenylcarbamoyl)-phenyl]-piperidin-1-yl}-3-methyl-benzoic acid 4-{4-[4-(3-tert-Butyl-phenylcarbamoyl)-phenyl]-piperidin-1-yl}-3-methyl-benzoic acid was synthesized from N-(3-tert-butyl-phenyl)-4-piperidin-4-yl-benzamide and 4-bromo-3-methyl-benzoic acid in a manner similar to the one described in the synthesis of 4-{4-[4-(3-tert-butyl-phenylcarbamoyl)-2-fluoro-phenyl]-piperazin-1-yl}-benzoic acid above.

LCMS calcd for C30H34N2O3 (m/e) 470, obsd 471 (M+H).

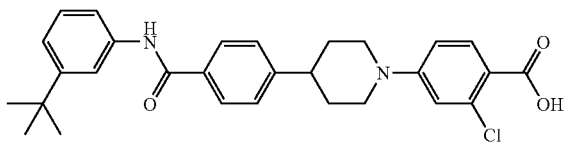

Example 133

4-{4-[4-(3-tert-Butyl-phenylcarbamoyl)-phenyl]-piperidin-1-yl}-2-chloro-benzoic acid 4-{4-[4-(3-tert-Butyl-phenylcarbamoyl)-phenyl]-piperidin-1-yl}-2-chloro-benzoic acid was synthesized from N-(3-tert-butyl-phenyl)-4-piperidin-4-yl-benzamide and 4-bromo-2-chloro-benzoic acid in a manner similar to the one described in the synthesis of 4-{4-[4-(3-tert-butyl-phenylcarbamoyl)-2-fluoro-phenyl]-piperazin-1-yl}-benzoic acid above.

LCMS calcd for C29H31ClN2O3 (m/e) 490, obsd 491 (M+H).

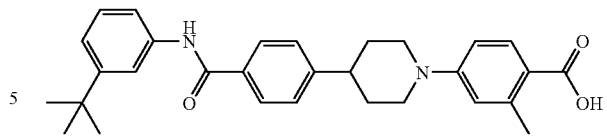

Example 134

4-{4-[4-(3-tert-Butyl-phenylcarbamoyl)-phenyl]-piperidin-1-yl}-2-methyl-benzoic acid 4-{4-[4-(3-tert-Butyl-phenylcarbamoyl)-phenyl]-piperidin-1-yl}-2-methyl-benzoic acid was synthesized from N-(3-tert-butyl-phenyl)-4-piperidin-4-yl-benzamide and 4-bromo-2-methyl-benzoic acid in a manner similar to the one described in the synthesis of 4-{4-[4-(3-tert-butyl-phenylcarbamoyl)-2-fluoro-phenyl]-piperazin-1-yl}-benzoic acid above.

LCMS calcd for C30H34N2O3 (m/e) 470, obsd 471 (M+H).

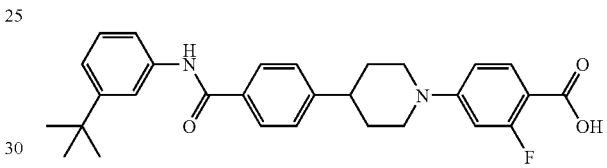

Example 135

4-{4-[4-(3-tert-Butyl-phenylcarbamoyl)-phenyl]-piperidin-1-yl}-2-fluoro-benzoic acid 4-{4-[4-(3-tert-Butyl-phenylcarbamoyl)-phenyl]-piperidin-1-yl}-2-fluoro-benzoic acid was synthesized from N-(3-tert-butyl-phenyl)-4-piperidin-4-yl-benzamide and 4-bromo-2-fluoro-benzoic acid in a manner similar to the one described in the synthesis of 4-{4-[4-(3-tert-butyl-phenylcarbamoyl)-2-fluoro-phenyl]-piperazin-1-yl}-benzoic acid above.

LCMS calcd for C29H31FN2O3 (m/e) 474, obsd 475 (M+H).

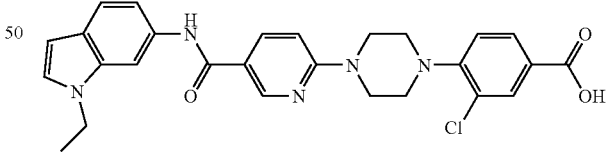

Example 136

3-Chloro-4-{4-[5-(1-ethyl-1H-indol-6-ylcarbamoyl)-pyridin-2-yl]-piperazin-1-yl}-benzoic acid 3-Chloro-4-{4-[5-(1-ethyl-1H-indol-6-ylcarbamoyl)-pyridin-2-yl]-piperazin-1-yl}-benzoic acid was synthesized from N-(1-ethyl-1H-indol-6-yl)-6-piperazin-1-yl-nicotinamide and 4-bromo-3-chloro-benzoic acid in a manner similar to the one described in the synthesis of 4-{4-[4-(3-tert-butylphenylcarbamoyl)-2-fluoro-phenyl]-piperazin-1-yl}-benzoic acid above. LCMS calcd for C27H26ClN5O3 (m/e) 503, obsd 504 (M+H).

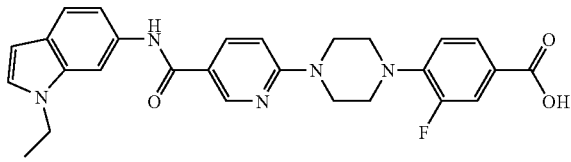

Example 137

3-Fluoro-4-{4-[5-(1-ethyl-1H-indol-6-ylcarbamoyl)-pyridin-2-yl]-piperazin-1-yl}-benzoic acid 3-fluoro-4-{4-[5-(1-ethyl-1H-indol-6-ylcarbamoyl)-pyridin-2-yl]-piperazin-1-yl}-benzoic acid was synthesized from N-(1-ethyl-1H-indol-6-yl)-6-piperazin-1-yl-nicotinamide and 4-bromo-3-fluoro-benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C27H26FN5O3 (m/e) 487, obsd 488 (M+H).

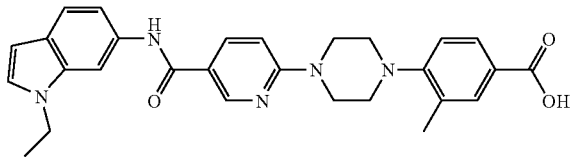

Example 138

3-methyl-4-{4-[5-(1-ethyl-1H-indol-6-ylcarbamoyl)-pyridin-2-yl]-piperazin-1-yl}-benzoic acid 3-methyl-4-{4-[5-(1-ethyl-1H-indol-6-ylcarbamoyl)-pyridin-2-yl]-piperazin-1-yl}-benzoic acid was synthesized from N-(1-ethyl-1H-indol-6-yl)-6-piperazin-1-yl-nicotinamide and 4-bromo-3-methyl-benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C28H29N5O3 (m/e) 483, obsd 484 (M+H).

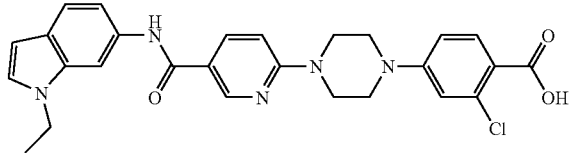

Example 139

2-Chloro-4-{4-[5-(1-ethyl-1H-indol-6-ylcarbamoyl)-pyridin-2-yl]-piperazin-1-yl}-benzoic acid 2-Chloro-4-{4-[5-(1-ethyl-1H-indol-6-ylcarbamoyl)-pyridin-2-yl]-piperazin-1-yl}-benzoic acid was synthesized from N-(1-ethyl-1H-indol-6-yl)-6-piperazin-1-yl-nicotinamide and 4-bromo-2-chloro-benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C27H26ClN5O3 (m/e) 503, obsd 504 (M+H).

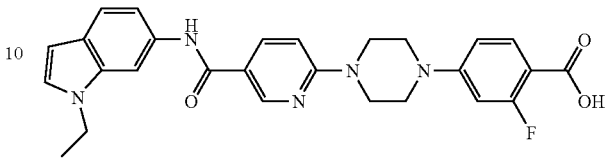

Example 140

2-fluoro-4-{4-[5-(1-ethyl-1H-indol-6-ylcarbamoyl)-pyridin-2-yl]-piperazin-1-yl}-benzoic acid 2-fluoro-4-{4-[5-(1-ethyl-1H-indol-6-ylcarbamoyl)-pyridin-2-yl]-piperazin-1-yl}-benzoic benzoic acid was synthesized from N-(1-ethyl-1H-indol-6-yl)-6-piperazin-1-yl-nicotinamide and 4-bromo-2-fluoro-benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C27H26FN5O3 (m/e) 487, obsd 488 (M+H).

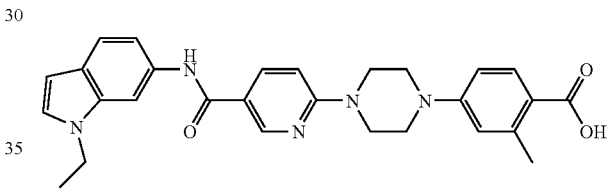

Example 141

2-methyl-4-{4-[5-(1-ethyl-1H-indol-6-ylcarbamoyl)-pyridin-2-yl]-piperazin-1-yl}-benzoic acid 2-methyl-4-{4-[5-(1-ethyl-1H-indol-6-ylcarbamoyl)-pyridin-2-yl]-piperazin-1-yl}-benzoic acid was synthesized from N-(1-ethyl-1H-indol-6-yl)-6-piperazin-1-yl-nicotinamide and 4-bromo-2-methyl-benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C28H29N5O3 (m/e) 483, obsd 484 (M+H).

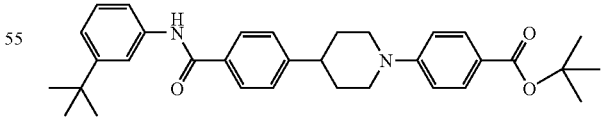

Example 142

4-{4-[4-(3-tert-Butyl-phenylcarbamoyl)-phenyl]-piperidin-1-yl}-benzoic acid tert-butyl ester 4-{4-[4-(3-tert-Butyl-phenylcarbamoyl)-phenyl]-piperidin-1-yl}-benzoic acid tert-butyl ester was synthesized from N-(3-tert-butyl-phenyl)-4-piperidin-4-yl-benzamide and 4-bromo-benzoic acid tert-butyl ester in a manner similar to the one described in the synthesis of 4-{4-[4-(3-tert-butyl-phenylcarbamoyl)-2-fluoro-phenyl]-piperazin-1-yl}-benzoic acid above. LCMS calcd for C33H40N2O3 (m/e) 512, obsd 513 (M+H).

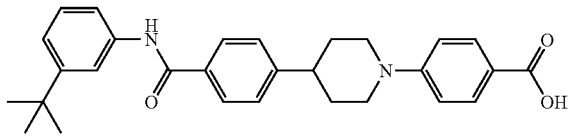

Example 143

4-{4-[4-(3-tert-Butyl-phenylcarbamoyl)-phenyl]-piperidin-1-yl}-benzoic acid

4-{4-[4-(3-tert-Butyl-phenylcarbamoyl)-phenyl]-piperidin-1-yl}-2-fluoro-benzoic acid was synthesized from N-(3-tert-butyl-phenyl)-4-piperidin-4-yl-benzamide and 4-bromo-2-fluoro-benzoic acid in a manner similar to the one described in the synthesis of 4-{4-[4-(3-tert-butyl-phenylcarbamoyl)-2-fluoro-phenyl]-piperazin-1-yl}-benzoic acid above. LCMS calcd for C29H32N2O3 (m/e) 456, obsd 457 (M+H)

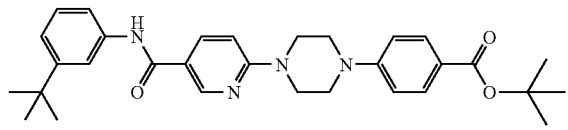

Example 144

4-{4-[5-(3-tert-Butyl-phenylcarbamoyl)-pyridin-2-yl]-piperazin-1-yl}-benzoic acid tert-butyl ester 4-{4-[5-(3-tert-Butyl-phenylcarbamoyl)-pyridin-2-yl]-piperazin-1-yl}-benzoic acid tert-butyl ester was synthesized from N-(3-tert-butyl-phenyl)-6-piperazin-1-yl-nicotinamide and 4-bromo benzoic acid tert-butyl ester in a manner similar to the one described in the synthesis of 4-{4-[4-(3-tert-butyl-phenylcarbamoyl)-2-fluoro-phenyl]-piperazin-1-yl}-benzoic acid above. LCMS calcd for C31H38N4O3 (m/e) 514, obsd 515 (M+H).

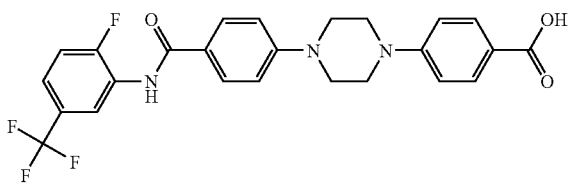

Example 145

4-{4-[4-(2-Fluoro-5-trifluoromethyl-phenylcarbamoyl)-phenyl]-piperazin-1-yl}-benzoic acid To a suspension of 4-[4-(4-carboxyphenyl)-piperazin-1-yl]-benzoic acid tert-butyl ester (100 mg, 0.26 mmol) in methylene chloride (5 mL) was added oxalyl chloride (2M, 0.2 mL) and a catalytic amount of DMF. The mixture was stirred for 30 minutes and solvents were evaporated. The residue was dried and then mixed with 2-fluoro-5-trifluoromethylaniline (65 mg, 0.36 mmol) and triethyl amine (56 μL, 0.38 mmol) in toluene (6 mL). The mixture was heated in a sealed tube at 140° C. for 3 hrs. Solvents were then evaporated and the residue was extracted with water and ethyl acetate. The organic layer was dried and evaporated. The residue was triturated with ethyl acetate to give the intermediate 4-{4-[4-(2-chloro-5-trifluoromethyl-phenylcarbamoyl)-phenyl]-piperazin-1-yl}-benzoic acid tert-butyl ester. This intermediate was then suspended in methylene chloride (3 mL and trifluoro acetic acid (1 mL) was added. The mixture was stirred for 1 hr and solvents were evaporated. The residue was dried and then triturated with ethyl acetate to give 4-{4-[4-(2-fluoro-5-trifluoromethyl-phenylcarbamoyl)-phenyl-piperazin-1-yl}-benzoic acid. LCMS calc for C25H21F4N3O3 (m/e) 487, obsd 488 (M+H).

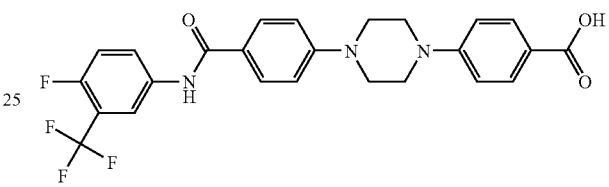

Example 146

4-{4-[4-(4-Fluoro-3-trifluoromethyl-phenylcarbamoyl)-phenyl]-piperazin-1-yl}-benzoic acid With the same method as described for the preparation of 4-{4-[4-(2-fluoro-5-trifluoromethyl-phenylcarbamoyl)-phenyl]-piperazin-1-yl}-benzoic acid, 4-{4-[4-(4-fluoro-3-trifluoromethyl-phenylcarbamoyl)-phenyl]-piperazin-1-yl}-benzoic acid was prepared starting from 4-[4-(4-carboxyphenyl)-piperazin-1-yl]-benzoic acid tent-butyl ester and 4-fluoro-3-trifluoromethylaniline. LCMS calc for C25H21F4N3O3 (m/e) 487, obsd 488 (M+H).

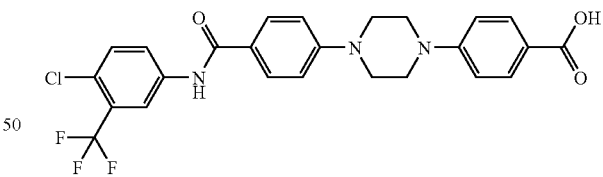

Example 147

4-{4-[4-(4-Chloro-3-trifluoromethyl-phenylcarbamoyl)-phenyl]-piperazin-1-yl}-benzoic acid With the same method as described for the preparation of 4-{4-[4-(2-fluoro-5-trifluoromethyl-phenylcarbamoyl)-phenyl]-piperazin-1-yl}-benzoic acid, 4-{4-[4-(4-chloro-3-trifluoromethyl-phenylcarbamoyl)-phenyl]-piperazin-1-yl}-benzoic acid was prepared starting from 4-[4-(4-carboxyphenyl)-piperazin-1-yl]-benzoic acid tert-butyl ester and 4-chloro-3-trifluoromethylaniline. LCMS calc for C25H21ClF3N3O3 (m/e) 503, obsd 504 (M+H).

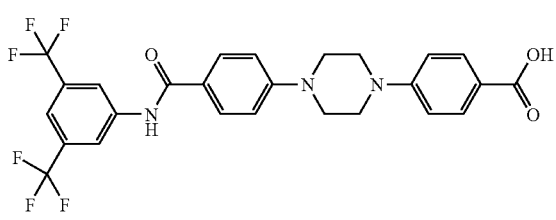

Example 148

4-{4-[4-(3,5-Bis-trifluoromethyl-phenylcarbamoyl)-phenyl]-piperazin-1-yl}-benzoic acid With the same method as described for the preparation of 4-{4-[4-(2-fluoro-5-trifluoromethyl-phenylcarbamoyl)-phenyl]-piperazin-1-yl}-benzoic acid, 4-{4-[4-(3,5-bis-trifluoromethyl-phenylcarbamoyl)-phenyl]-piperazin-1-yl}-benzoic acid was prepared through the coupling of 4-[4-(4-carboxyphenyl)-piperazin-1-yl]-benzoic acid tert-butyl ester and 3,5-bis-trifluoromethylaniline. LCMS calc for C26H21F6N3O3 (m/e) 537 obsd 538 (M+H).

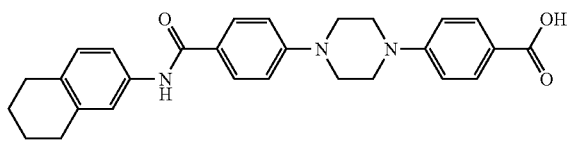

Example 149

4-{4-[4-(5,6,7,8-Tetrahydro-naphthalen-2-ylcarbamoyl)-phenyl]-piperazin-1-yl}-benzoic acid With the same method as described for the preparation of 4-{4-[4-(2-fluoro-5-trifluoromethyl-phenylcarbamoyl)-phenyl]-piperazin-1-yl}-benzoic acid, 4-{4-[4-(5,6,7,8-tetrahydro-naphthalen-2-ylcarbamoyl)-phenyl]-piperazin-1-yl}-benzoic acid was prepared starting from 4-[4-(4-carboxyphenyl)-piperazin-1-yl]-benzoic acid tart-butyl ester and 5,6,7,8-tetrahydro-naphthalen-2-ylamine. LCMS calc for C28H29N3O3 (m/e) 455, obsd 454 (M−H).

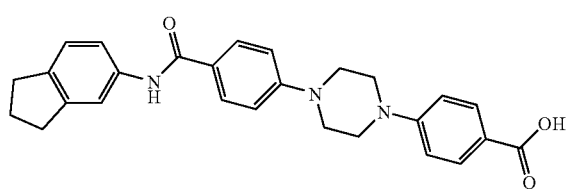

Example 150

4-{4-[4-(Indan-5-ylcarbamoyl)-phenyl]-piperazin-1-yl}-benzoic acid

With the same method as described for the preparation of 4-{4-[4-(2-fluoro-5-trifluoromethyl-phenylcarbamoyl)-phenyl]-piperazin-1-yl}-benzoic acid, 4-{4-[4-(indan-5-ylcarbamoyl)-phenyl]-piperazin-1-yl}-benzoic acid was prepared starting from 4-[4-(4-carboxyphenyl)-piperazin-1-yl]-benzoic acid tert-butyl ester and 5-aminoindan. LCMS calc for C27H27N3O3 (m/e) 441, obsd 442 (M+H).

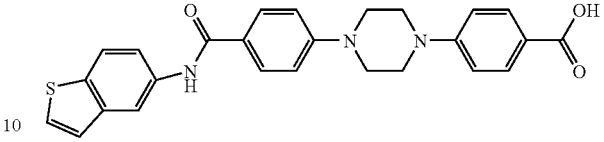

Example 151

4-{4-[4-(Benzo[b]thiophen-5-ylcarbamoyl)-phenyl]-piperazin-1-yl}-benzoic acid

With the same method as described for the preparation of 4-{4-[4-(2-fluoro-5-trifluoromethyl-phenylcarbamoyl)-phenyl]-piperazin-1-yl}-benzoic acid, 4-{4-[4-(benzo[b]thiophen-5-ylcarbamoyl)-phenyl]-piperazin-1-yl}-benzoic acid was prepared from 4-[4-(4-carboxyphenyl)-piperazin-1-yl]-benzoic acid tert-butyl ester and benzo[b]thiophen-5-ylamine. LCMS calc for C26H23N3O3S (m/e) 457, obsd 458 (M+H).

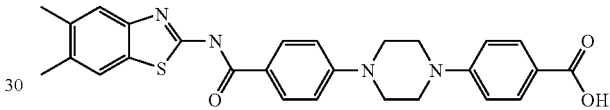

Example 152

4-{4-[4-(5,6-Dimethyl-benzothiazol-2-ylcarbamoyl)-phenyl]-piperazin-1-yl}-benzoic acid With the same method as described for the preparation of 4-{4-[4-(2-fluoro-5-trifluoromethyl-phenylcarbamoyl)-phenyl]-piperazin-1-yl}-benzoic acid, 4-{4-[4-(5,6-dimethyl-benzothiazol-2-ylcarbamoyl)-phenyl]-piperazin-1-yl}-benzoic acid was prepared starting from 4-[4-(4-carboxyphenyl)-piperazin-1-yl]-benzoic acid tert-butyl ester and 5,6-dimethyl-benzothiazol-2-ylamine. LCMS calcd for C27H26N4O3S (m/e) 486, obsd 487 (M+H).

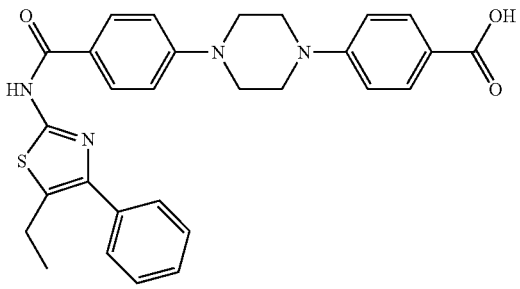

Example 153

4-{4-[4-(5-Ethyl-4-phenyl-thiazol-2-ylcarbamoyl)-phenyl]-piperazin-1-yl}-benzoic acid With the same method as described for the preparation of 4-{4-[4-(2-fluoro-5-trifluoromethyl-phenylcarbamoyl)-phenyl]-piperazin-1-yl}-benzoic acid, 4-{4-[4-(5-ethyl-4-phenyl-thiazol-2-ylcarbamoyl)-phenyl]-piperazin-1-yl}-benzoic acid was prepared starting from 4-[4-(4-carboxyphenyl)-piperazin-1-yl]-benzoic acid tert-butyl ester and 5-ethyl-4-phenyl-thiazol-2-ylamine. LCMS calc for C29H28N4O3S (m/e) 512, obsd 513 (M+H).

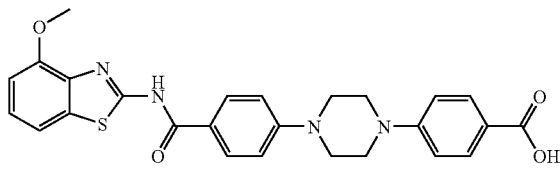

Example 154

4-{4-[4-(4-Methoxy-benzothiazol-2-ylcarbamoyl)-phenyl]-piperazin-1-yl}-benzoic acid With the same method as described for the preparation of 4-{4-[4-(2-fluoro-5-trifluoromethyl-phenylcarbamoyl)-phenyl]-piperazin-1-yl}-benzoic acid, 4-{4-[4-(5-ethyl-4-phenyl-thiazol-2-ylcarbamoyl)-phenyl]-piperazin-1-yl}-benzoic acid was prepared from 4-[4-(4-carboxyphenyl)-piperazin-1-yl]-benzoic acid tert-butyl ester and 4-methoxy-benzothiazol-2-ylamine. LCMS calc for C26H24N4O4S (m/e) 488, obsd 489 (M+H).

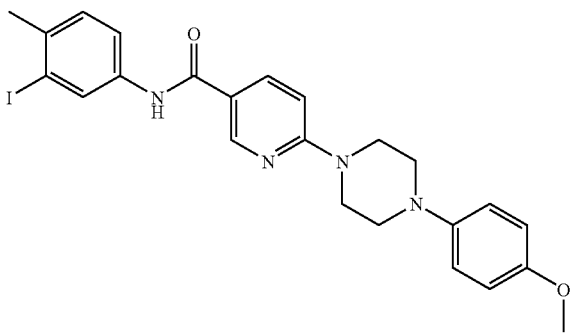

Example 155

N-(3-Iodo-4-methyl-phenyl)-6-[4-(4-methoxy-phenyl)-piperazin-1-yl]-nicotinamide 4-methoxyphenyl piperazine dihydrochloride (110 mg, 0.41 mmol) was partitioned between CH₂Cl₂ and 2N aq. NaOH. The aqueous layer was extracted twice more with CH₂Cl₂ and the combined organic layer was dried and concentrated. The residue was dissolved in dioxane (6 mL). The solution was then treated with diisopropyl ethylamine (0.07 mL, 0.41 mmol), a catalytic amount of DMAP and 6-chloro-N-(3-iodo-4-methyl-phenyl)-nicotinamide (50 mg, 0.13 mmol). The mixture was heated in a sealed tube at 120° C. for 22 hr. The mixture was then cooled, followed addition of another portion of 4-methoxyphenyl piperazine hydrochloride (110 mg, 0.41 mmol) and diisopropyl ethyl amine (0.14 mL, 0.82 mmol). The mixture was stirred at 120° C. for 3 more days then cooled and partitioned between EtOAc and aq. saturated Na₂CO₃. The organic layer was dried over Na₂SO₄, filtered and concentrated. The residue was chromatographed on a silica gel column with 20-40% EtOAc in hexanes to afford the product. HRMS m/z calcd for C24H25N4O2I [M+H]⁺: 529.1095. Found: 529.1098.

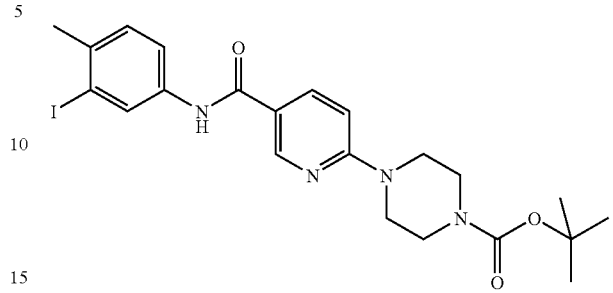

Example 156

4-[5-(3-Iodo-4-methyl-phenylcarbamoyl)-pyridin-2-yl]-piperazine-1-carboxylic acid tert-butyl ester A solution of 6-chloro-N-(3-iodo-4-methyl-phenyl)-nicotinamide (100 mg, 0.26 mmol), a catalytic amount of DMAP, diisopropylethyl amine (0.27 mL, 1.61 mmol), t-Boc-piperazine (300 mg, 1.61 mmol) in 5 mL in dioxane was heated at 95° C. in a sealed tube for about 72 h. The reaction mixture was then cooled and partitioned between EtOAc and aq. saturated Na₂CO₃. The organic layer was then collected, dried over Na₂SO₄ filtered and concentrated. The residue was chromatographed with a silica gel column and 20-40% EtOAc in hexanes to afford the product (105 mg. Yield: 75%). HRMS m/z calcd for C22H27N4O3I [M+H]⁺: 523.1201. Found: 523.1200.

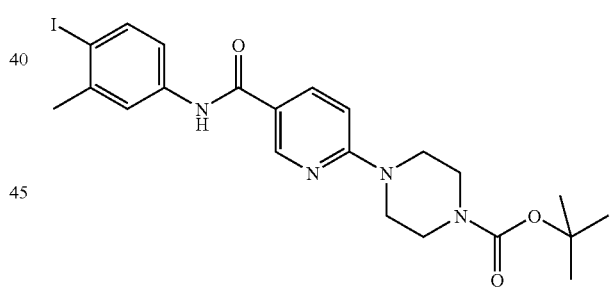

Example 157

4-[5-(4-Iodo-3-methyl-phenylcarbamoyl)-pyridin-2-yl]-piperazine-1-carboxylic acid tert-butyl ester 4-[5-(4-Iodo-3-methyl-phenylcarbamoyl)-pyridin-2-yl]-piperazine-1-carboxylic acid tert-butyl ester was prepared from 6-chloro-N-(4-iodo-3-methyl-phenyl)-nicotinamide and 1-Boc-piperazine following a procedure similar to the one described in the synthesis of 4-[5-(3-iodo-4-methyl-phenylcarbamoyl)-pyridin-2-yl]-piperazine-1-carboxylic acid tert-butyl ester above. The product was obtained after silica gel column purification with 20-40% EtOAc in hexanes gradient. HRMS m/z calcd for C22H27N4O3I [M+H]⁺: 523.1201. Found: 523.1202.

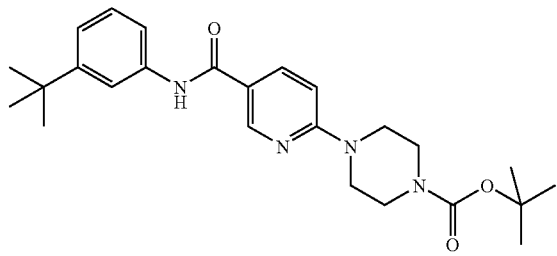

Example 158

4-[5-(3-tert-Butyl-phenylcarbamoyl)-pyridin-2-yl]-piperazine-1-carboxylic acid tert-butyl ester 4-[5-(3-tert-Butyl-phenylcarbamoyl)-pyridin-2-yl]-piperazine-1-carboxylic acid tert-butyl ester was prepared from N-(3-tert-butyl-phenyl)-6-chloro-nicotinamide and 1-Boc-piperazine following a procedure similar to the one described in the synthesis of 4-[5-(3-iodo-4-methyl-phenylcarbamoyl)-pyridin-2-yl]-piperazine-1-carboxylic acid tert-butyl ester above. The product was obtained after silica gel column purification with 10-30% EtOAc in hexanes gradient. HRMS m/z calcd for C25H34N4O3 [M+H]$^+$: 439.2704. Found: 439.2704.

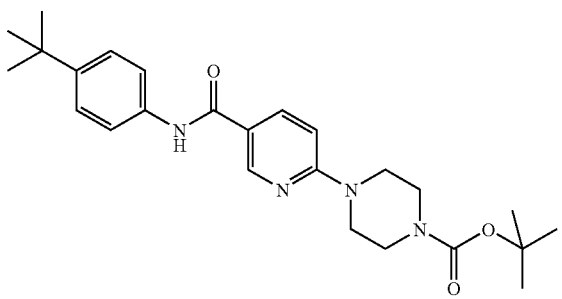

Example 159

4-[5-(4-tert-Butyl-phenylcarbamoyl)-pyridin-2-yl]-piperazine-1-carboxylic acid tert-butyl ester 4-[5-(4-tert-Butyl-phenylcarbamoyl)-pyridin-2-yl]-piperazine-1-carboxylic acid tert-butyl ester was prepared from N-(4-tert-butyl-phenyl)-6-chloro-nicotinamide and 1-Boc-piperazine following a procedure similar to the one described in the synthesis of 4-[5-(3-iodo-4-methyl-phenylcarbamoyl)-pyridin-2-yl]-piperazine-1-carboxylic acid tert-butyl ester above. The product was obtained after silica gel column purification with 10-30% EtOAc in hexanes gradient. HRMS m/z calcd for C25H34N4O3 [M+H]$^+$: 439.2704. Found: 4392700.

Example 160

4-[5-(1-Ethyl-1H-indol-6-ylcarbamoyl)-pyridin-2-yl]-piperazine-1-carboxylic acid tert-butyl ester 4-[5-(1-Ethyl-1H-indol-6-ylcarbamoyl)-pyridin-2-yl]-piperazine-1-carboxylic acid tert-butyl ester was prepared from 6-chloro-N-(1-ethyl-1H-indol-6-yl)-nicotinamide and 1-Boc-piperazine following a method similar to the one described in the synthesis of 4-[5-(3-iodo-4-methyl-phenylcarbamoyl)-pyridin-2-yl]-piperazine-1-carboxylic acid tert-butyl ester above. The product was obtained after silica gel column purification with 10-30% Et$_2$O in toluene gradient. HRMS m/z calcd for C25H31N5O3 [M+H]$^+$: 450.2500. Found: 450.2497.

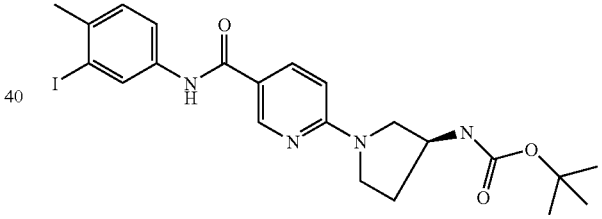

Example 161

{(S)-1-[5-(3-Iodo-4-methyl-phenylcarbamoyl)-pyridin-2-yl]-pyrrolidin-3-yl}-carbamic acid tert-butyl ester {(S)-1-[5-(3-Iodo-4-methyl-phenylcarbamoyl)-pyridin-2-yl]-pyrrolidin-3-yl}-carbamic acid tert-butyl ester was prepared from 6-chloro-N-(3-iodo-4-methyl-phenyl)-nicotinamide and (−)-(S)-3-(Boc-amino)pyrrolidine following a method similar to the one described in the synthesis of 4-[5-(3-iodo-4-methyl-phenylcarbamoyl)-pyridin-2-yl]-piperazine-1-carboxylic acid tert-butyl ester above. The product was isolated after a silica gel column purification and a precipitation out of THF with excess of hexanes. HRMS m/z calcd for C22H27N4O3I [M+H]$^+$: 523.1201. Found: 523.1201.

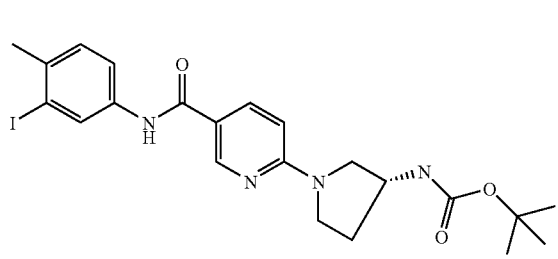

Example 162

{(R)-1-[5-(3-Iodo-4-methyl-phenylcarbamoyl)-pyridin-2-yl]-pyrrolidin-3-yl}-carbamic acid tert-butyl ester {(R)-1-[5-(3-Iodo-4-methyl-phenylcarbamoyl)-pyridin-2-yl]-pyrrolidin-3-yl}-carbamic acid tert-butyl ester was prepared from 6-chloro-N-(3-iodo-4-methyl-phenyl)-nicotinamide and (+)-(R)-3-(Boc-amino)pyrrolidine following a method similar to the one described in the synthesis of 4-[5-(3-iodo-4-methyl-phenylcarbamoyl)-pyridin-2-yl]-piperazine-1-carboxylic acid tert-butyl ester above. The product was isolated after a silica gel column purification and a precipitation out of THF with excess of hexanes. HRMS m/z calcd for C22H27N4O3I [M+H]$^+$: 523.1201. Found: 523.1201.

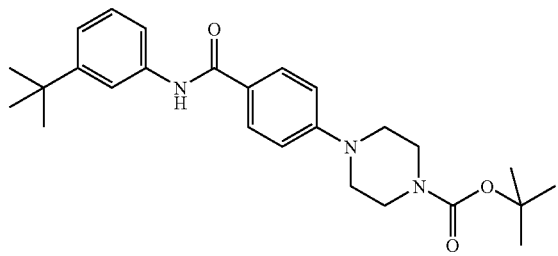

Example 163

4-[4-(3-tert-Butyl-phenylcarbamoyl)-phenyl]-piperazine-1-carboxylic acid tert-butyl ester A mixture of 3-tert-butyl aniline (117 mg, 0.78 mmol), 4-(4-carboxy-phenyl)-piperazine-1-carboxylic acid tert-butyl ester (prepared as described in Biog. Med. Chem. 2006, 14, 2089) (200 mg, 0.65 mmol), EDCl (375 mg, 0.95 mmol) and a catalytic amount of DMAP in CH$_2$Cl$_2$ was stirred at room temperature overnight. The next day the mixture was partitioned between EtOAc and water. The organic layer was collected, dried over Na$_2$SO$_4$, filtered and concentrated. The residue was chromatographed with silica gel column amd 0-30% EtOAc in hexanes gradient to afford the product (100 mg, Yield: 35%). HRMS m/z calcd for C26H35N3O3 [M+H]$^+$: 438.2751. Found: 438.2753.

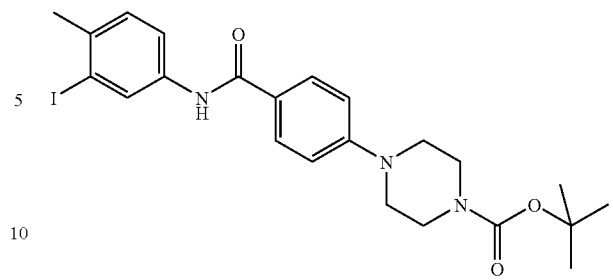

Example 164

4-[4-(3-Iodo-4-methyl-phenylcarbamoyl)-phenyl]-piperazine-1-carboxylic acid tert-butyl ester 4-[4-(3-Iodo-4-methyl-phenylcarbamoyl)-phenyl]-piperazine-1-carboxylic acid tert-butyl ester was prepared from 3-iodo-4-methyl aniline and 4-(4-carboxy-phenyl)-piperazine-1-carboxylic acid tert-butyl ester in a manner similar to the one described in the synthesis of 4-[4-(3-tert-butyl-phenylcarbamoyl)-phenyl]-piperazine-1-carboxylic acid tert-butyl ester, above. The product was isolated after a silica gel purification with 10-30% Et$_2$O in toluene. HRMS m/z calcd for C23H28N3O3I [M+H]: 522.1248. Found: 522.1246.

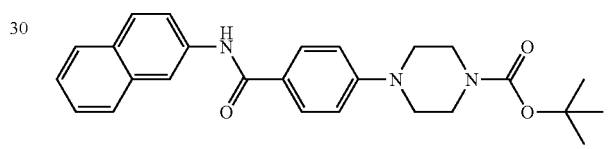

Example 165

4-[4-(Naphthalen-2-ylcarbamoyl)-phenyl]-piperazine-1-carboxylic acid tert-butyl ester 4-[4-(Naphthalen-2-ylcarbamoyl)-phenyl]-piperazine-1-carboxylic acid tert-butyl ester was synthesized from 4-(4-carboxy-phenyl)-piperazine-1-carboxylic acid tert-butyl ester and naphthalen-2-ylamine in a manner similar to the one described in the synthesis of 4-[4-(3-tert-butyl-phenylcarbamoyl)-phenyl]-piperazine-1-carboxylic acid tert-butyl ester, above. LCMS calcd for C26H29N3O3 (m/e) 431, obsd 432 (M+H).

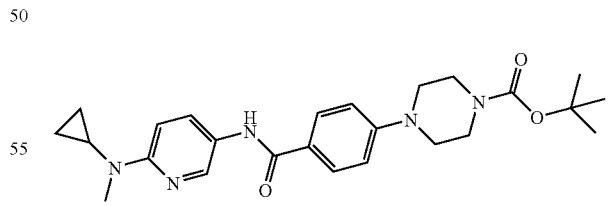

Example 166

4-{4-[6-(Cyclopropyl-methyl-amino)-pyridin-3-ylcarbamoyl]-phenyl}-piperazine-1-carboxylic acid tert-butyl ester 4-{4-[6-(Cyclopropyl-methyl-amino)-pyridin-3-ylcarbamoyl]-phenyl}-piperazine-1-carboxylic acid tert-butyl ester was synthesized from 4-(4-carboxy-phenyl)-piperazine-1-carboxylic acid tert-butyl ester and N-2-cyclopropyl-N2-methyl-pyridine-2,5-diamine in a manner similar to the one described in the synthesis of 4-[4-(3-tert-butyl-phenylcarbamoyl)-phenyl]-piperazine-1-carboxylic acid tert-butyl ester, above. LCMS calcd for C25H33N5O3 (m/e) 451, obsd 452 (M+H).

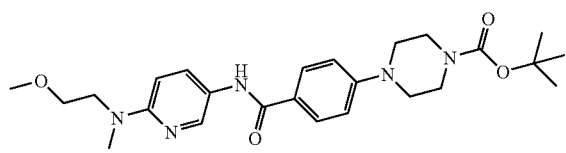

Example 167

4-(4-{6-[(2-Methoxy-ethyl)-methyl-amino]-pyridin-3-ylcarbamoyl}-phenyl)-piperazine-1-carboxylic acid tert-butyl ester 4-(4-{6-[(2-Methoxy-ethyl)-methyl-amino]-pyridin-3-ylcarbamoyl}-phenyl)-piperazine-1-carboxylic acid tert-butyl ester was synthesized from 4-(4-carboxy-phenyl)-piperazine-1-carboxylic acid tert-butyl ester and N-2-methoxyethylyl-N-2-methyl-pyridine-2,5-diamine in a in a manner similar to the one described in the synthesis of 4-[4-(3-tert-butyl-phenylcarbamoyl)-phenyl]-piperazine-1-carboxylic acid tert-butyl ester, above. LCMS calcd for C25H35N5O4 (m/e) 469, obsd 470 (M+H).

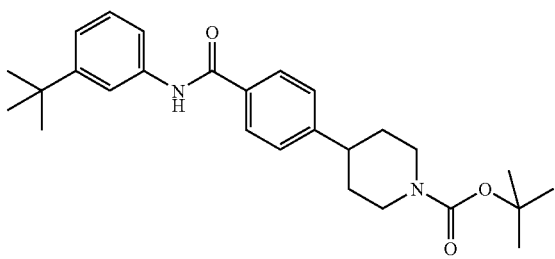

Example 168

4-[4-(3-tert-Butyl-phenylcarbamoyl)-phenyl]-piperidine-1-carboxylic acid tert-butyl ester 4-[4-(3-tert-Butyl-phenylcarbamoyl)-phenyl]-piperidine-1-carboxylic acid tert-butyl ester was prepared from N-Boc-4-(4-carboxyphenyl)piperidine and 3-tert-butyl aniline in a manner similar to the one described in the synthesis of 4-[4-(3-tert-butyl-phenylcarbamoyl)-phenyl]-piperazine-1-carboxylic acid tert-butyl ester, above. The product was isolated after silica gel column purification with 10-50% Et$_2$O in hexanes. HRMS m/z calcd for C26H35N3O3I [M+H]$^+$: 437.2799. Found: 437.2796.

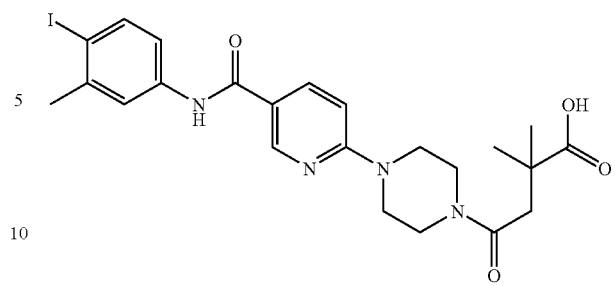

Example 169

4-{4-[5-(4-Iodo-3-methyl-phenylcarbamoyl)-pyridin-2-yl]-piperazin-1-yl}-2,2-dimethyl-4-oxo-butyric acid 4-[5-(4-Iodo-3-methyl-phenylcarbamoyl)-pyridin-2-yl]-piperazine-1-carboxylic acid tert-butyl ester (35 mg, 0.07 mmol) was dissolved in 30% TFA in CH$_2$Cl$_2$ solution at room temperature. The mixture was stirred for 30 min and then partitioned between EtOAc and H$_2$O. The water layer was made basic by the addition of Na$_2$CO$_3$. The organic layer was then collected washed with water dried over Na$_2$SO$_4$, filtered and evaporated. The residue was dissolved in CH$_2$Cl$_2$ and treated with 2,2-dimethysuccinic anhydride (13 mg, 0.10 mmol). After stirring at room temperature for 4 h the mixture was concentrated to a residue and washed with excess of hexanes to afford the product. HRMS m/z calcd for C23H27N4O4I [M+H]$^+$: 551.1150. Found: 551.1152.

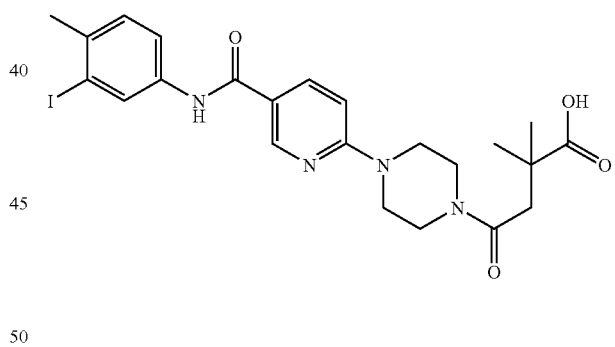

Example 170

4-{4-[5-(3-Iodo-4-methyl-phenylcarbamoyl)-pyridin-2-yl]-piperazin-1-yl}-2,2-dimethyl-4-oxo-butyric acid 4-{4-[5-(3-Iodo-4-methyl-phenylcarbamoyl)-pyridin-2-yl]-piperazin-1-yl}-2,2-dimethyl-4-oxo-butyric acid was prepared from 4-[5-(3-iodo-4-methyl-phenylcarbamoyl)-pyridin-2-yl]-piperazine-1-carboxylic acid tert-butyl ester and 2,2-dimethysuccinic anhydride following a procedure similar to the one described in the synthesis of 4-{4-[5-(4-iodo-3-methyl-phenylcarbamoyl)-pyridin-2-yl]-piperazin-1-yl}-dimethyl-4-oxo-butyric acid above. HRMS m/z calcd for C23H27N4O4I [M+H]$^+$: 551.1150. Found: 551.1152.

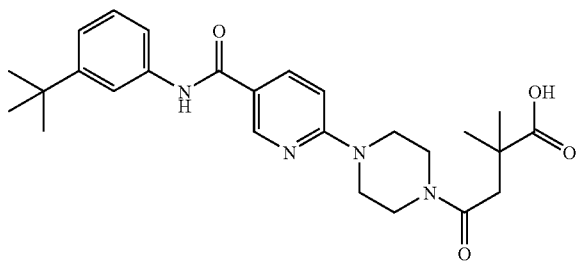

Example 171

4-{4-[5-(3-tert-Butyl-phenylcarbamoyl)-pyridin-2-yl]-piperazin-1-yl}-2,2-dimethyl-4-oxo-butyric acid A mixture of N-(3-tert-butyl-phenyl)-6-piperazin-1-yl-nicotinamide (20 mg, 0.06 mmol) in $CH_2Cl_2$ (5 mL) was treated with 2,2-dimethylsuccinic anhydride (11 mg, 0.07 mmol). After stirring at rt overnight the solvent was evaporated. The residue was dissolved in a very small volume of $CH_2Cl_2$. The product was isolated by precipitation after addition of excess of hexanes (25 mg, Yield: 91%) HRMS m/z calcd for $C26H34N4O4$ $[M+H]^+$: 467.2653. Found: 467.2652.

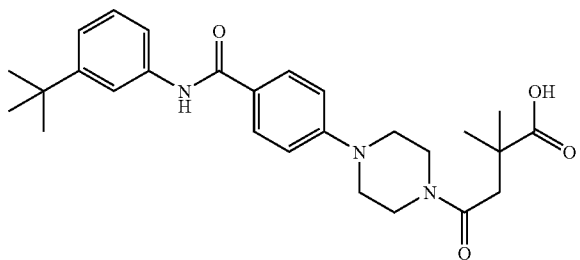

Example 172

4-{4-[4-(3-tert-Butyl-phenylcarbamoyl)-phenyl]-piperazin-1-yl}-2,2-dimethyl-4-oxo-butyric acid 4-{4-[4-(3-tert-Butyl-phenylcarbamoyl)-phenyl]-piperazin-1-yl}-2,2-dimethyl-4-oxo-butyric acid was prepared from 2,2-dimethylsuccinic anhydride and N-(3-tert-butyl-phenyl)-4-piperazin-1-yl-benzamide. HRMS m/z calcd for $C27H35N3O4$ $[M+H]^+$: 466.2701. Found: 466.2698.

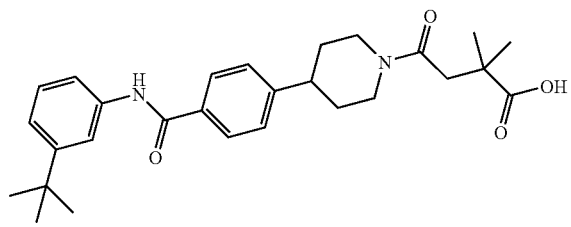

Example 173

4-{4-[4-(3-tert-Butyl-phenylcarbamoyl)-phenyl]-piperidin-1-yl}-2,2-dimethyl-4-oxo-butyric acid 4-{4-[4-(3-tert-Butyl-phenylcarbamoyl)-phenyl]-piperidin-1-yl}-2,2-dimethyl-4-oxo-butyric acid was synthesized from N-(3-tert-butyl-phenyl)-4-piperidin-4-yl-benzamide and 2,2-dimethylsuccinic anhydride in a method similar to the one described in the synthesis of 4-{4-[5-(3-tert-butyl-phenylcarbamoyl)-pyridin-2-yl]-piperazin-1-yl}-2,2-dimethyl-4-oxo-butyric acid above. LCMS calcd for $C28H36N2O4$ (m/e) 464, obsd 465 (M+H).

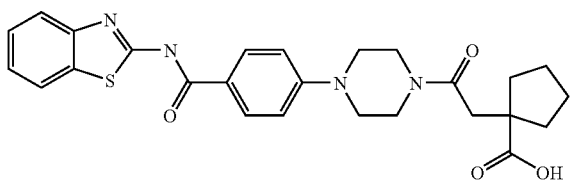

Example 174

1-(2-{4-[4-(Benzothiazol-2-ylcarbamoyl)-phenyl]-piperazin-1-yl}-2-oxo-ethyl)-cyclopentanecarboxylic acid N-benzothiazol-2-yl-4-piperazin-1-yl-benzamide trifluoroacetate (40 mg) was mixed with 2-oxa-spiro[4,4]nonane-1,3-dione (30 mg) in DMF (5 mL) containing triethylamine (0.1 mL) and the mixture was stirred foe 5 hrs. Solvents were evaporated and the residue was treated with ethyl acetate and hydrochloric acid solution (0.1N). The precipitate from the organic layer was filtered to give 1-(2-{4-[4-(benzothiazol-2-ylcarbamoyl)-phenyl]-piperazin-1-yl}-2-oxo-ethyl)-cyclopentanecarboxylic acid as a white solid (30 mg). LCMS calc for $C26H28N4O4S$ (m/e) 492, obsd 493.

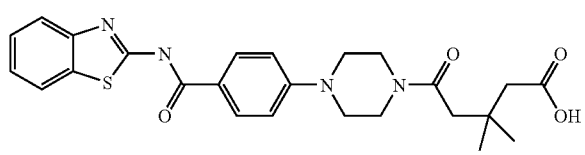

Example 175

5-{4-[4-(Benzothiazol-2-ylcarbamoyl)-phenyl]-piperazin-1-yl}-3,3-dimethyl-5-oxo-pentanoic acid With the same method as described for the preparation of 1-(2-{4-[4-(benzothiazol-2-ylcarbamoyl)-phenyl]-piperazin-1-yl}-2-oxo-ethyl)-cyclopentanecarboxylic acid, 5-{4-[4-(benzothiazol-2-ylcarbamoyl)-phenyl]-piperazin-1-yl}-3,3-dimethyl-5-oxo-pentanoic acid was prepared from N-benzothiazol-2-yl-4-piperazin-1-yl-benzamide trifluoroacetate and 4,4-dimethyl-dihydropyran-2,6-dione. LCMS calcd for $C25H28N4O4S$ (m/e) 480, obsd 481 (M+H)

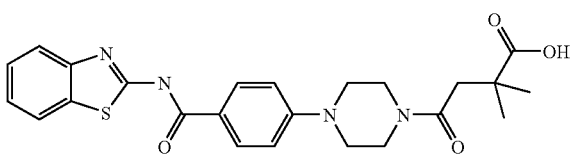

Example 176

4-{4-[4-(Benzothiazol-2-ylcarbamoyl)-phenyl]-piperazin-1-yl}-2,2-dimethyl-4-oxo-butyric acid With the same method as described for the preparation of 1-(2-{4-[4-(benzothiazol-2-ylcarbamoyl)-phenyl]-piperazin-1-yl}-2-oxo-ethyl)-cyclopentanecarboxylic acid, 4-{4-[4-(benzothiazol-2-ylcarbamoyl)-phenyl]-piperazin-1-yl}-2,2-dimethyl-4-oxo-butyric acid was prepared from N-benzothiazol-2-yl-4-piperazin-1-yl-benzamide trifluoroacetate and 3,3-dimethyl-dihydrofuran-2,5-dione. LCMS calcd for C24H26N4O4S (m/e) 466, obsd 467

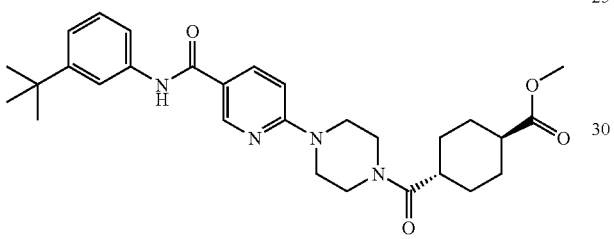

Example 177

4-{4-[5-(3-tert-Butyl-phenylcarbamoyl)-pyridin-2-yl]-piperazine-1-carbonyl}-cyclohexanecarboxylic acid methyl ester A mixture of N-(3-tert-butyl-phenyl)-6-piperazin-1-yl-nicotinamide (100 mg, 0.29 mmol) in CH$_2$Cl$_2$ (10 mL) was treated with trans-1,4-cyclohexane dicarboxylic acid monomethyl ester. (110 mg, 0.59 mmol) and EDCI (230 mg, 1.18 mmol) at room temperature. After stirring overnight the reaction mixture was partitioned between EtOAc and water. The organic layer was collected, dried over Na$_2$SO$_4$, filtered and concentrated. The residue was chromatographed on a silica gel column with 20-100% EtOAc in hexanes gradient to afford the product (120 mg, Yield: 80%). HRMS m/z calcd for C29H38N4O4 [M+H]$^+$: 507.2966. Found: 507.2968.

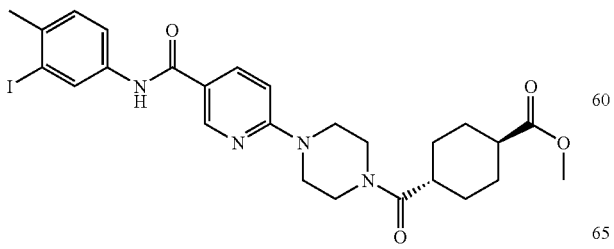

Example 178

4-{4-[5-(3-Iodo-4-methyl-phenylcarbamoyl)-pyridin-2-yl]-piperazine-1-carbonyl}-cyclohexanecarboxylic acid methyl ester 4-{4-[5-(3-Iodo-4-methyl-phenylcarbamoyl)-pyridin-2-yl]-piperazine-1-carbonyl}-cyclohexanecarboxylic acid methyl ester was prepared from N-(3-iodo-4-methyl-phenyl)-6-piperazin-1-yl-nicotinamide and trans-1,4-cyclohexane dicarboxylic acid monomethyl ester in a manner similar to the one described in the synthesis of 4-{4-[5-(3-tert-butyl-phenylcarbamoyl)-pyridin-2-yl]-piperazine-1-carbonyl}-cyclohexane-carboxylic acid methyl ester above. The product was obtained after a silica gel column purification with a 50-100% EtOAc in hexanes gradient. HRMS m/z calcd for C26H31N4O4I [M+H]$^+$: 591.1463. Found: 591.1461.

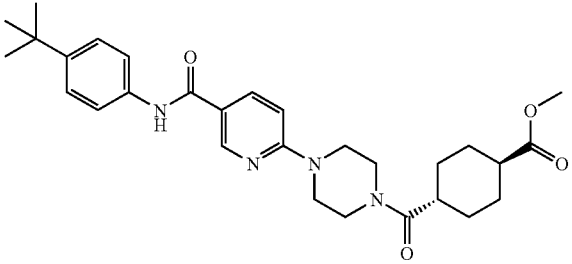

Example 179

4-{4-[5-(4-tert-Butyl-phenylcarbamoyl)-pyridin-2-yl]-piperazine-1-carbonyl}-cyclohexanecarboxylic acid methyl ester 4-{4-[5-(4-tert-Butyl-phenylcarbamoyl)-pyridin-2-yl]-piperazine-1-carbonyl}-cyclohexanecarboxylic acid methyl ester was prepared from N-(4-tert-butyl-phenyl)-6-piperazin-1-yl-nicotinamide and trans-1,4-cyclohexane dicarboxylic acid monomethyl ester using a procedure similar to the one described in the synthesis of 4-{4-[5-(3-tert-butyl-phenylcarbamoyl)-pyridin-2-yl]-piperazine-1-carbonyl}-cyclohexanecarboxylic acid above. The product was isolated after silica gel column purification with 20-100% EtOAc in hexanes gradient. HRMS m/z calcd for C29H38N4O4 [M+H]$^+$: 507.2966. Found: 507.2969.

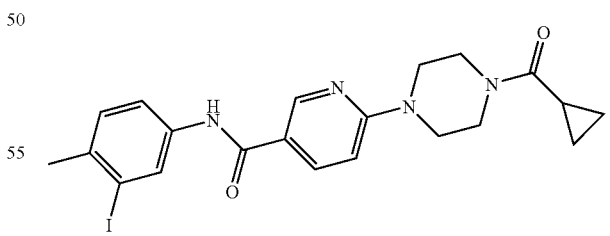

Example 180

6-(4-Cyclopropanecarbonyl-piperazin-1-yl)-N-(3-iodo-4-methyl-phenyl)-nicotinamide 6-(4-Cyclopropanecarbonyl-piperazin-1-yl)-N-(3-iodo-4-methyl-phenyl)-nicotinamide was synthesized by the EDCI coupling of N-(3-iodo-4-methyl-phenyl)-6-piperazin-1-yl-nicotinamide and cyclopropanecarboxylic acid in a manner similar to the one described in the synthesis of 4-{4-[5-(3-tert-butyl-phenylcarbamoyl)-pyridin-2-yl]-piperazine-1-carbonyl}-cyclohexanecarboxylic acid methyl ester, above. LCMS calcd for C21H23IN4O2 (m/e) 490, obsd 491 (M+H).

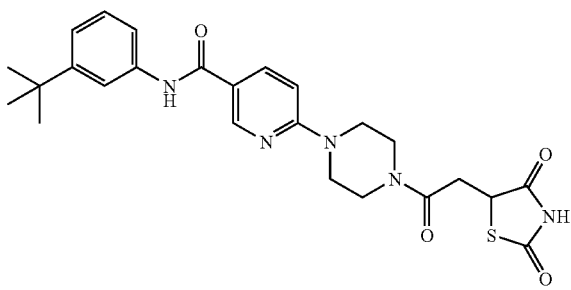

Example 181

N-(3-tert-Butyl-phenyl)-6-{4-[2-(2,4-dioxo-thiazolidin-5-yl)-acetyl]-piperazin-1-yl}-nicotinamide N-(3-tert-Butyl-phenyl)-6-{-4-[2-(2,4-dioxo-thiazolidin-5-yl)-acetyl]-piperazin-1-yl}-nicotinamide was prepared by the ECDI coupling of 2,4-dioxo 1,3 thiazolidine acetic acid with N-(3-tert-butyl-phenyl)-6-piperazin-1-yl-nicotinamide in DMF in a manner similar to the one described in the synthesis of 4-{4-[5-(3-tert-butyl-phenylcarbamoyl)-pyridin-2-yl]-piperazine-1-carbonyl}-cyclohexanecarboxylic acid methyl ester, above. The product was isolated after a silica gel column with 0-2% MeOH in CH$_2$Cl$_2$. HRMS m/z calcd for C25H29N5O4S [M+H]$^+$: 496.2013. Found: 496.2011.

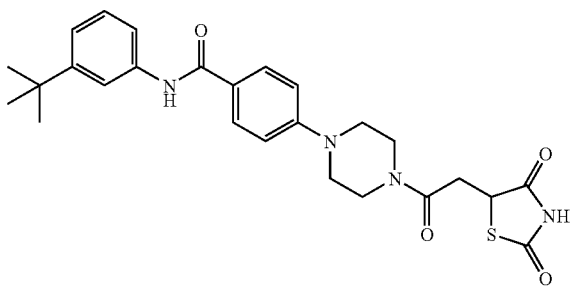

Example 182

N-(3-tert-Butyl-phenyl)-4-{4-[2-(2,4-dioxo-thiazoil-din-5-yl)-acetyl]-piperazin-1-yl}-benzamide N-(3-tert-Butyl-phenyl)-4-{4-[2-(2,4-dioxo-thiazolidin-5-yl)-acetyl]-piperazin-1-yl}-benzamide was prepared by the ECDI coupling of 2,4-dioxo 1,3 thiazolidine acetic acid with N-(3-tert-butyl-phenyl)-4-piperazin-1-yl-benzamide in DMF in a manner similar to the one described in the synthesis of 4-{4-[5-(3-tert-butyl-phenylcarbamoyl)-pyridin-2-yl]-piperazine-1-carbonyl}-cyclohexanecarboxylic acid methyl ester, above. The product was isolated after a silica gel column with 0-3% MeOH in CH$_2$Cl$_2$. HRMS m/z calcd for C26H30N4O4S [M+H]$^+$: 495.2061. Found: 495.2061.

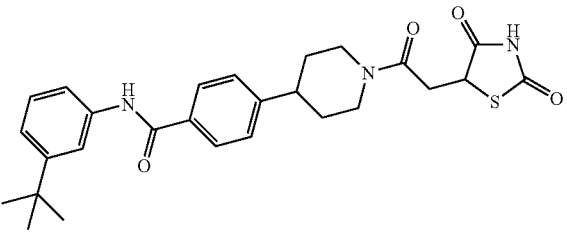

Example 183

N-(3-tert-Butyl-phenyl)-4-{1-[2-(2,4-dioxo-thiazolidin-5-yl)-acetyl]-piperidin-4-yl}-benzamide N-(3-tent-Butyl-phenyl)-4-{1-[2-(2,4-dioxo-thiazolidin-5-yl)-acetyl]-piperidin-4-yl}-benzamide was synthesized by the ECDI coupling of N-(3-tert-butyl-phenyl)-4-piperidin-4-yl-benzamide and 2-(2,4-dioxo-thiazolidin-5-yl)-acetic acid in a manner similar to the one described in the synthesis of 4-{4-[5-(3-tert-butyl-phenylcarbamoyl)-pyridin-2-yl]-piperazine-1-carbonyl}-cyclohexanecarboxylic acid methyl ester, above. LCMS calcd for C27H31N3O4S (m/e) 493, obsd 494 (M+H).

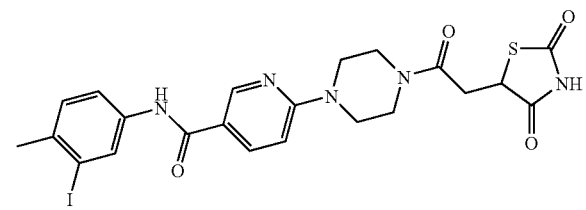

Example 184

6-{4-[2-(2,4-Dioxo-thiazolidin-5-yl)-acetyl]-piperazin-1-yl}-N-(3-iodo-4-methyl-phenyl)-nicotinamide 6-{4-[2-(2,4-Dioxo-thiazolidin-5-yl)-acetyl]-piperazin-1-yl}-N-(3-iodo-4-methyl-phenyl)-nicotinamide was synthesized by the ECDI coupling of N-(3-iodo-4-methyl-phenyl)-6-piperazin-1-yl-nicotinamide and 2-(2,4-dioxo-thiazolidin-5-yl)-acetic acid in a manner similar to the one described in the synthesis of 4-{4-[5-(3-tert-butyl-phenylcarbamoyl)-pyridin-2-yl]-piperazine-1-carbonyl}-cyclohexanecarboxylic acid methyl ester, above. LCMS calcd for C22H22IN5O4S (m/e) 579, obsd 580 (M+H).

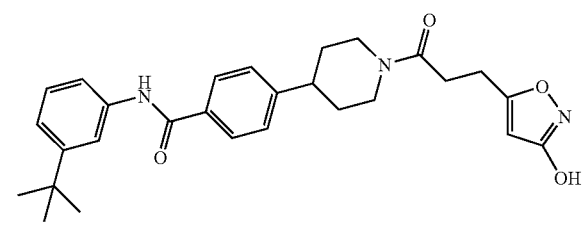

Example 185

N-(3-tert-Butyl-phenyl)-4-{1-[3-(3-hydroxy-isoxazol-5-yl)-propionyl]-piperidin-4-yl}-benzamide N-(3-tert-Butyl-phenyl)-4-{1-[3-(3-hydroxy-isoxazol-5-yl)-propionyl]-piperidin-4-yl}-benzamide was prepared by the ECDI coupling of N-(3-tert-butyl-phenyl)-4-piperidin-4-yl-benzamide and 3-(3-hydroxy-isoxazol-5-yl)-propionic acid in a manner similar to the one described in the synthesis of 4-{4-[5-(3-tert-butyl-phenylcarbamoyl)-pyridin-2-yl]-piperazine-1-carbonyl}-cyclohexanecarboxylic acid methyl ester, above. LCMS calcd for C28H33N3O4 (m/e) 475, obsd 476 (M+H).

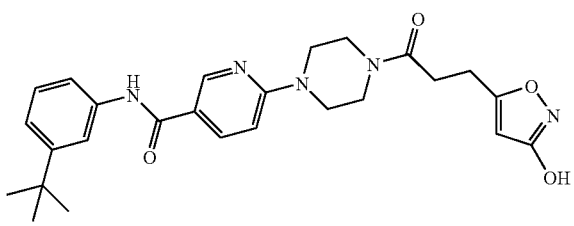

Example 186

N-(3-tert-Butyl-phenyl)-6-{4-[3-(3-hydroxy-isoxazol-5-yl)-propionyl]-piperazin-1-yl}-nicotinamide N-(3-tert-Butyl-phenyl)-6-{4-[3-(3-hydroxy-isoxazol-5-yl)-propionyl]-piperazin-1-yl}-nicotinamide was synthesized from the EDCI coupling of N-(3-tert-butyl-phenyl)-6-piperazin-1-yl-nicotinamide and 3-(3-hydroxy-isoxazol-5-yl)-propionic acid in a manner similar to the one described in the synthesis of 4-{4-[5-(3-tert-butyl-phenylcarbamoyl)-pyridin-2-yl]-piperazine-1-carbonyl}-cyclohexanecarboxylic acid methyl ester, above. LCMS calcd for C26H31N5O4 (m/e) 477, obsd 478 (M+H).

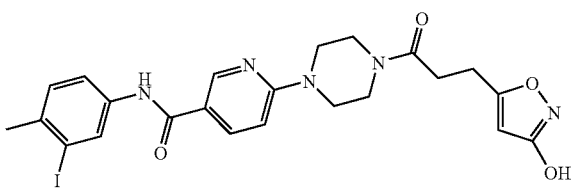

Example 187

6-{4-[3-(3-Hydroxy-isoxazol-5-yl)-propionyl]-piperazin-1-yl}-N-(3-iodo-4-methyl-phenyl)-nicatinamide 6-{4-[3-(3-Hydroxy-isoxazol-5-yl)-propionyl]-piperazin-1-yl}-N-(3-iodo-4-methyl-phenyl)-nicotinamide was synthesized from the EDCI coupling of N-(3-iodo-4-methyl-phenyl)-6-piperazin-1-yl-nicotinamide and 3-(3-hydroxy-isoxazol-5-yl)-propionic acid in a manner similar to the one described in the synthesis of 4-{4-[5-(3-tert-butyl-phenylcarbamoyl)-pyridin-2-yl]-piperazine-1-carbonyl}-cyclohexanecarboxylic acid methyl ester, above. LCMS calcd for C23H24IN5O4 (m/e) 561, obsd 562 (M+H),

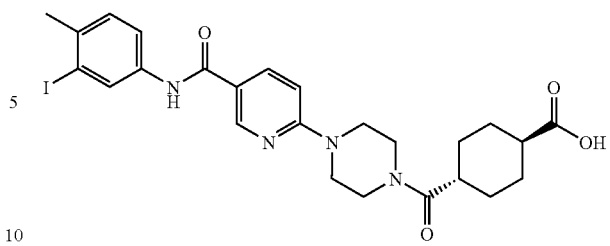

Example 188

4-{4-[5-(3-Iodo-4-methyl-phenylcarbamoyl)-pyridin-2-yl]-piperazine-1-carbonyl}-cyclohexanecarboxylic acid A mixture of N-(3-iodo-4-methyl-phenyl)-6-piperazin-1-yl-nicotinamide (60 mg, 0.14 mmol), trans-1,4-cyclohexane dicarboxylic acid (122 mg, 0.71 mmol) in DMF (10 mL) was treated with EDCI (130 mg, 0.71 mmol). After stirring overnight the reaction mixture was partitioned between EtOAc and water. The water layer was made basic to pH 13 with solid NaOH. The EtOAc layer was removed and then the water layer was acidified to pH 5 with aq conc. HCl and extracted again with EtOAc. The EtOAc layer obtained after the latter extraction was dried over Na2SO4, filtered and concentrated to the product (10 mg, Yield: 12%). HRMS m/z calcd for C25H29N4O4I [M+H]+: 577.1306. Found: 577.1306.

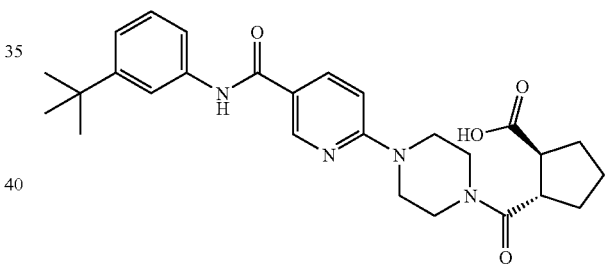

Example 189

(1S,2S)-2-{4-[5-(3-tert-Butyl-phenylcarbamoyl)-pyridin-2-yl]-piperazine-1-carbonyl}-cyclopentanecarboxylic acid A mixture of N-(3-tert-butyl-phenyl)-6-piperazin-1-yl-nicotinamide (60 mg, 0.17 mmol) and (1S,2S)-cyclopentane-1,2-dicarboxylic acid monobenzyl ester (88 mg, 0.35 mmol) in CH2Cl2 (10 mL) was treated with EDCI (136 mg, 0.77 mmol). Upon consumption of the limiting reagent, as judged by TLC, the mixture was partitioned between EtOAc and water. The EtOAc layer was dried over Na2SO4, filtered, and concentrated and the residue was chromatographed on silica gel column with 40-100% EtOAc in hexanes to afford the intermediate coupling benzylester product. This material was then dissolved in EtOH (10 mL). Followed addition of 10% Pd/C (9 mg) and the resulting mixture was hydrogenated under 1 atm of hydrogen for 4.5 h. The solids were then removed by filtration and washed with THF. The combined filtrate was evaporated and the resulting residue was dissolved in a small volume of CH2Cl2 (approx 1 mL). Addition of excess of hexanes resulted in the precipitation of the product (64 mg, Yield: 75%). HRMS m/z calcd for C29H38N4O4 [M+H]+: 479.2563. Found: 579.2564.

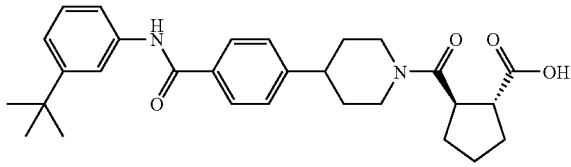

Example 190

(1R,2R)-2-{4-[4-(3-tert-Butyl-phenylcarbamoyl)-phenyl]-piperidine-1-carbonyl}-cyclopentanecarboxylic acid (1R,2R)-2-{4-[4-(3-tert-Butyl-phenylcarbamoyl)-phenyl]-piperidine-1-carbonyl}-cyclopentanecarboxylic acid was synthesized from (1S,2S)-cyclopentane-1,2-dicarboxylic acid monobenzyl ester and N-(3-tert-butyl-phenyl)-4-piperidin-4-yl-benzamide in a manner similar to the one described in the synthesis of (1S,2S)-2-{4-[5-(3-tert-butyl-phenylcarbamoyl)-pyridin-2-yl]-piperazine-1-carbonyl}-cyclopentane-carboxylic acid above. LCMS calcd for C29H36N2O4 (m/e) 476, obsd 477 (M+H).

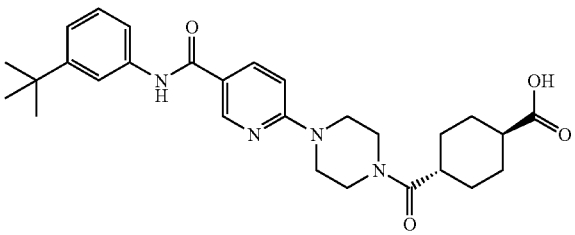

Example 191

4-{4-[5-(3-tert-Butyl-phenylcarbamoyl)-pyridin-2-yl]-piperazine-1-carbonyl}-cyclohexanecarboxylic acid 4-{4-[5-(3-tert-Butyl-phenylcarbamoyl)-pyridin-2-yl]-piperazine-1-carbonyl}-cyclohexanecarboxylic acid was prepared from N-(3-tert-butyl-phenyl)-6-piperazin-1-yl-nicotinamide and trans-1,4-cyclohexane dicarboxylic acid monobenzyl ester in a manner similar to the one described in the synthesis of (1S,2S)-2-{4-[5-(3-tert-butyl-phenylcarbamoyl)-pyridin-2-yl]-piperazine-1-carbonyl}-cyclopentanecarboxylic acid above. HRMS m/z calcd for C28H36N4O4 [M+H]+: 493.2810. Found: 493.2807.

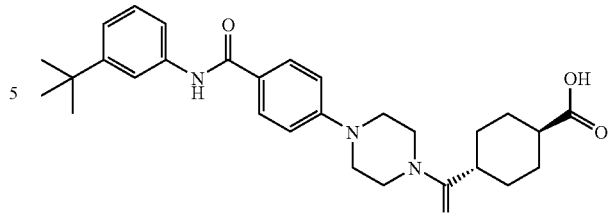

Example 192

4-{4-[4-(3-tert-Butyl-phenylcarbamoyl)-phenyl]-piperazine-1-carbonyl}-cyclohexanecarboxylic acid 4-{4-[4-(3-tert-Butyl-phenylcarbamoyl)-phenyl]-piperazine-1-carbonyl}-cyclohexanecarboxylic acid was prepared from N-(3-tert-butyl-phenyl)-4-piperazin-1-yl-benzamide and trans-1,4-cyclohexane dicarboxylic acid monobenzyl ester in a manner similar to the one described in the synthesis of (1S,2S)-2-{4-[5-(3-tert-butyl-phenylcarbamoyl)-pyridin-2-yl]-piperazine-1-carbonyl}-cyclopentanecarboxylic acid above. HRMS m/z calcd for C29H37N3O4 [M+H]: 492.2857. Found: 492.2855.

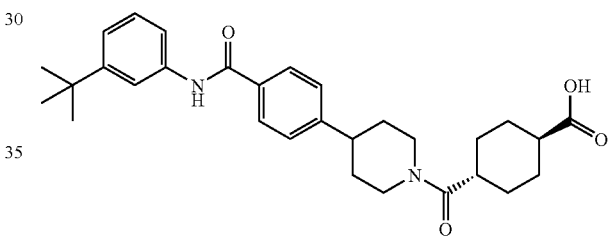

Example 193

4-{4-[4-(3-tert-Butyl-phenylcarbamoyl)-phenyl]-piperidine-1-carbonyl}-cyclohexanecarboxylic acid 4-{4-[4-(3-tert-Butyl-phenylcarbamoyl)-phenyl]-piperidine-1-carbonyl}-cyclohexanecarboxylic acid was prepared from N-(3-tert-butyl-phenyl)-4-piperidin-4-yl-benzamide and trans-1,4-cyclohexane dicarboxylic acid monobenzyl ester in a manner similar to the one described in the synthesis of (1S,2S)-2-{4-[5-(3-tert-butyl-phenylcarbamoyl)-pyridin-2-yl]-piperazine-1-carbonyl}-cyclopentanecarboxylic acid above. LCMS calcd for C30H38N2O4 (m/e) 490, obsd 491 (M+H).

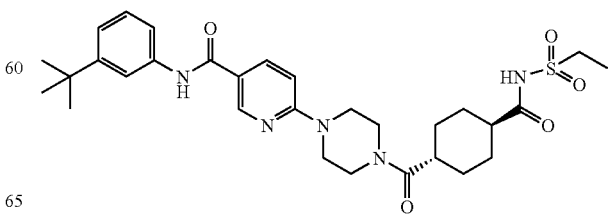

Example 194

N-(3-tert-Butyl-phenyl)-6-[4-(4-ethanesulfonylaminocarbonyl-cyclohexanecarbonyl)-piperazin-1-yl]-nicotinamide N-(3-tert-Butyl-phenyl)-6-[4-(4-ethanesulfonylaminocarbonyl-cyclohexanecarbonyl)-piperazin-1-yl]-nicotinamide was prepared from 4-{4-[5-(3-tert-butyl-phenylcarbamoyl)-pyridin-2-yl]-piperazine-1-carbonyl}-cyclohexanecarboxylic acid and ethyl sulfonamide in a manner similar to the one described in the synthesis of 4-(2-methyl-propane-2-sulfonylaminocarbonyl)-3,4,5,6-tetrahydro-2H-[1,2']bipyridinyl-5'-carboxylic acid (4-iodo-3-methyl-phenyl)-amide above. The product was isolated after silica gel purification with 0-3% MeOH in $CH_2Cl_2$ gradient. HRMS m/z calcd for $C_{30}H_{41}N_5O_5S$ [M+H]$^+$: 584.2901. Found: 584.2902.

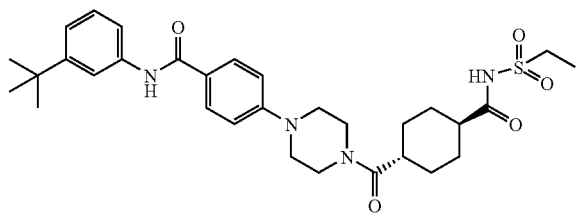

Example 195

N-(3-tert-Butyl-phenyl)-4-[4-(4-ethanesulfonylaminocarbonyl-cyclohexanecarbonyl)-piperazin-1-yl]-benzamide N-(3-tert-Butyl-phenyl)-4-[4-(4-ethanesulfonylaminocarbonyl-cyclohexanecarbonyl)-piperazin-1-yl]-benzamide was prepared from 4-{4-[4-(3-tert-butyl-phenylcarbamoyl)-phenyl]-piperazine-1-carbonyl}-cyclohexanecarboxylic acid and ethyl sulfonamide in a manner similar to the one described in the synthesis of 4-(2-methyl-propane-2-sulfonylaminocarbonyl)-3,4,5,6-tetrahydro-2H-[1,2']bipyridinyl-5'-carboxylic acid (4-iodo-3-methyl-phenyl)-amide above. The product was isolated after silica gel purification with 0-3% MeOH in $CH_2Cl_2$ gradient. HRMS m/z calcd for $C_{31}H_{42}N_4O_5S$ [M+H]$^+$: 583.2949. Found: 583.2945.

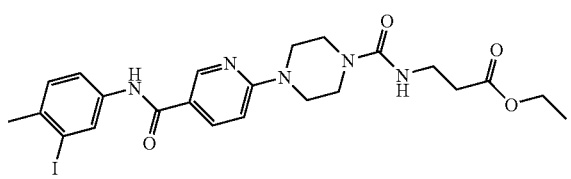

Example 196

3-({4-[5-(3-Iodo-4-methyl-phenylcarbamoyl)-pyridin-2-yl]-piperazine-1-carbonyl}-amino)-propionic acid ethylester N-(3-iodo-4-methyl-phenyl)-6-piperazin-1-yl-nicotinamide and 3-isocyanato-propionic acid ethyl ester was synthesized by the addition of 3-isocyanato-propionic acid ethyl ester (0.055 mmol) to N-(3-iodo-4-methyl-phenyl)-6-piperazin-1-yl-nicotinamide (0.05 mmol) partially dissolved in DCM and stirred at room temperature overnight. The reaction was concentrated to dryness under a stream of nitrogen and tritrated from ethyl ether producing the product, N-(3-iodo-4-methyl-phenyl)-6-piperazin-1-yl-nicotinamide and 3-isocyanato-propionic acid ethyl ester, as a white solid. LCMS calcd for $C_{23}H_{28}IN_5O_4$ (m/e) 565, obsd 566 (M+H).

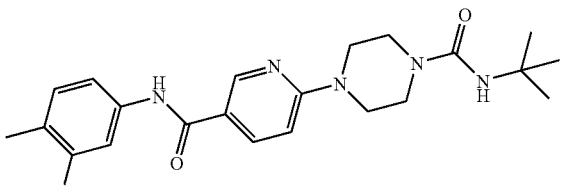

Example 197

4-[5-(3-Iodo-4-methyl-phenylcarbamoyl)-pyridin-2-yl]-piperazine-1-carboxylic acid tert-butylamide 4-[5-(3-Iodo-4-methyl-phenylcarbamoyl)-pyridin-2-yl]-piperazine-1-carboxylic acid tert-butylamide was synthesized from N-(3-iodo-4-methyl-phenyl)-6-piperazin-1-yl-nicotinamide and tertbutyl isocyanate in a manner similar to the one described in the synthesis of 3-({4-[5-(3-iodo-4-methyl-phenylcarbamoyl)-pyridin-2-yl]-piperazine-1-carbonyl}-amino)-propionic acid ethylester above. LCMS calcd for $C_{22}H_{28}IN_5O_2$ (m/e) 521, obsd 522 (M+H).

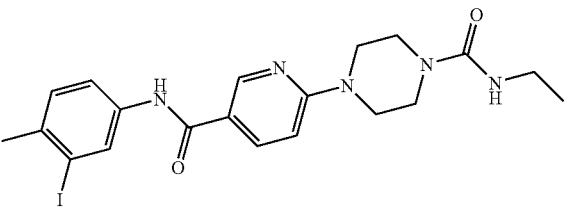

Example 198

4-[5-(3-Iodo-4-methyl-phenylcarbamoyl)-pyridin-2-yl]-piperazine-1-carboxylic acid ethylamide 4-[5-(3-Iodo-4-methyl-phenylcarbamoyl)-pyridin-2-yl]-piperazine-1-carboxylic acid tert-butylamide was synthesized from N-(3-iodo-4-methyl-phenyl)-6-piperazin-1-yl-nicotinamide and ethyl isocyanate in a manner similar to the one described in the synthesis of 3-({4-[5-(3-iodo-4-methyl-phenylcarbamoyl)-pyridin-2-yl]-piperazine-1-carbonyl}-amino)-propionic acid ethylester above. LCMS calcd for $C_{20}H_{24}IN_5O_2$ (m/e) 493, obsd 494 (M+H).

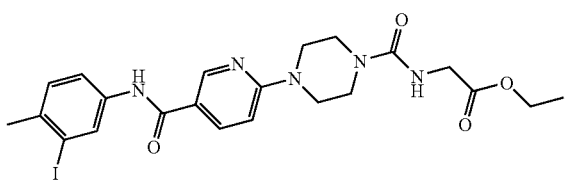

Example 199

({4-[5-(3-Iodo-4-methyl-phenylcarbamoyl)-pyridin-2-yl]-piperazine-1-carbonyl}-amino)-acetic acid ethyl ester 3-({4-[5-(3-Iodo-4-methyl-phenylcarbamoyl)-pyridin-2-yl]-piperazine-1-carbonyl}-amino)-acetic acid ethyl ester was synthesized from N-(3-iodo-4-methyl-phenyl)-6-piperazin-1-yl-nicotinamide and isocyanato-acetic acid ethyl ester in a manner similar to the one described in the synthesis of 3-({-4-[5-(3-iodo-4-methyl-phenylcarbamoyl)-pyridin-2-yl]-piperazine-1-carbonyl}-amino)-propionic acid ethylester above. LCMS calcd for C22H26IN5O4 (m/e) 551, obsd 552 (M+H).

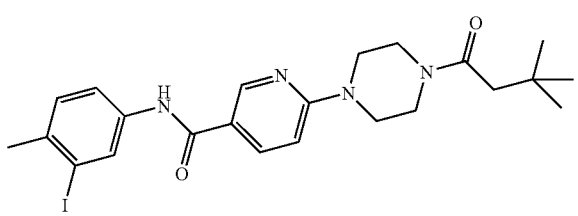

Example 200

6-[4-(3,3-Dimethyl-butyryl)-piperazin-1-yl]-N-(3-iodo-4-methyl-phenyl)-nicotinamide 6-[4-(3,3-Dimethyl-butyryl)-piperazin-1-yl]-N-(3-iodo-4-methyl-phenyl)-nicotinamide was synthesized by the addition 3,3-dimethyl-butyryl chloride (0.055 mmol) to N-(3-iodo-4-methyl-phenyl)-6-piperazin-1-yl-nicotinamide (0.05 mmol) partially dissolved in DCM followed by the addition of TEA and stirred at room temperature over night. The reaction was diluted with ethyl acetate washed with water and brine, dried over sodium sulfate, concentrated and the residue was trirturated with ether and hexanes to afford the product, 6-[4-(3,3-dimethyl-butyryl)-piperazin-1-yl]-N-(3-iodo-4-methyl-phenyl)-nicotinamide. LCMS calcd for C23H29IN4O2 (m/e) 520, obsd 521 (M+H).

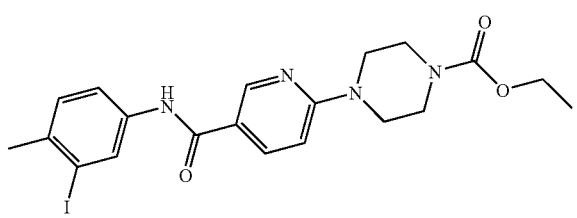

Example 201

4-[5-(3-Iodo-4-methyl-phenylcarbamoyl)-pyridin-2-yl]-piperazine-1-carboxylic acid ethyl ester 4-[5-(3-Iodo-4-methyl-phenylcarbamoyl)-pyridin-2-yl]-piperazine-1-carboxylic acid ethyl ester was synthesized from N-(3-iodo-4-methyl-phenyl)-6-piperazin-1-yl-nicotinamide and ethylchloroformate in a manner similar to the one described in the synthesis of 6-[4-(3,3-dimethyl-butyryl)-piperazin-1-yl]-N-(3-iodo-4-methyl-phenyl)-nicotinamide above. LCMS calcd for C20H23IN4O3 (m/e) 494, obsd 495 (M+H).

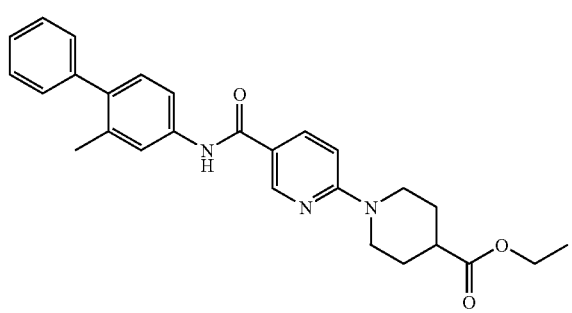

Example 202

5'-(2-Methyl-biphenyl-4-ylcarbamoyl)-3,4,5,6-tetrahydro-2H-[1,2']bipyridinyl-4-carboxylic acid ethyl ester A mixture of 6-(4-Iodo-3-methyl-phenylcarbamoyl)-3,4,5,6-tetrahydro-2H-[1,2']bipyridinyl-4-carboxylic acid ethyl ester (100 mg, 0.19 mmol), phenylboronic acid (36 mg, 0.29 mmol), Na2CO3 (40 mg, 0.39 mmol) and water (0.6 mL) in dioxane in a sealed tube was degassed by bubbling nitrogen into the mixture for approximately 3 min. Followed addition of Pd(Ph3P)4 (11 mg, 0.01 mmol), the vessel was sealed and the mixture was heated under vigorous stirring for 4.5 h. The mixture was then cooled the solvent was evaporated and the residue was chromatographed on a silica gel column with 40% EtOAc in hexanes to afford the product. (70 mg, Yield: 81%). HRMS m/z calcd for C27H29N3O3 [M+H]+: 444.2282. Found: 444.2282

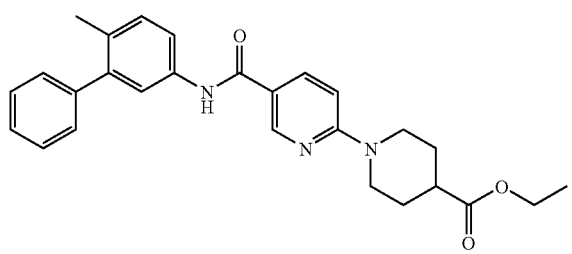

Example 203

5'-(6-Methyl-biphenyl-3-yl-carbamoyl)-3,4,5,6-tetrahydro-2H-[1,2']bipyridinyl-4-carboxylic acid ethyl ester 5'-(6-methyl-biphenyl-3-yl-carbamoyl)-3,4,5,6-tetrahydro-2H-[1,2']bipyridinyl-4-carboxylic acid ethyl ester was prepared from 5'-(3-iodo-4-methyl-phenylcarbamoyl)-3,4,5,6-tetrahydro-2H-[1,2']bipyridinyl-4 carboxylic acid ethyl ester and phenylboronic acid following a method similar to the one described in the synthesis of 5'-(2-methyl-biphenyl-4-ylcarbamoyl)-3,4,5,6-tetrahydro-2H-[1,2']bipyridinyl-4-carboxylic acid ethyl ester above. The product was isolated after silica gel column purification with 20-50% EtOAc in hexanes gradient. HRMS m/z calcd for C27H29N3O3 [M+H]+: 444.2282. Found: 444.2282

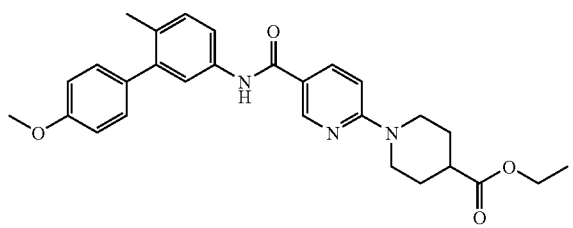

Example 204

5'-(4'-Methoxy-6-methyl-biphenyl-3-ylcarbamoyl)-3,4,5,6-tetrahydro-2H-[1,2']-bipyridinyl-4-carboxylic acid ethyl ester 5'-(4'-Methoxy-6-methyl-biphenyl-3-ylcarbamoyl)-3,4,5,6-tetrahydro-2H-[1,2']-bipyridinyl-4-carboxylic acid ethyl ester was prepared from 5'-(3-iodo-4-methyl-phenylcarbamoyl)-3,4,5,6-tetrahydro-2H-[1,2']bipyridinyl-4 carboxylic acid ethyl ester and 4-methoxyphenyl boronic acid following a method similar to the one described in the synthesis of 5'-(2-methyl-biphenyl-4-ylcarbamoyl)-3,4,5,6-tetrahydro-2H-[1,2']bipyridinyl-4-carboxylic acid ethyl ester above. The product was isolated after silica gel column purification with 20-40% EtOAc in hexanes gradient. HRMS m/z calcd for C28H31N3O4 [M+H]+: 474.2388. Found: 474.2386.

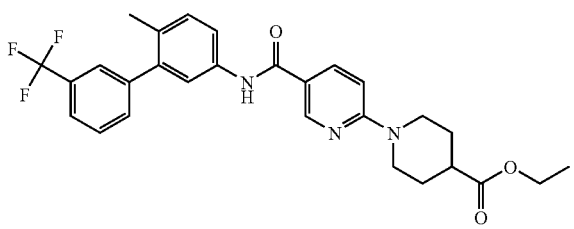

Example 205

5'-(6-Methyl-T-trifluoromethyl-biphenyl-3-ylcarbamoyl)-3,4,5,6-tetrahydro-2H-[1,2']-bipyridinyl-4-carboxylic acid ethyl ester 5'-(6-Methyl-3'-trifluoromethyl-biphenyl-3-ylcarbamoyl)-3,4,5,6-tetrahydro-2H-[1,2']-bipyridinyl-4-carboxylic acid ethyl ester was prepared from 5'-(3-iodo-4-methyl-phenylcarbamoyl)-3,4,5,6-tetrahydro-2H-[1,2']bipyridinyl-4 carboxylic acid ethyl ester and 3-trifluoromethylphenyl boronic acid following a method similar to the one described in the synthesis of 5'42-methyl-biphenyl-4-ylcarbamoyl)-3,4,5,6-tetrahydro-2H-[1,2']bipyridinyl-4-carboxylic acid ethyl ester above. The product was isolated after silica gel column purification with 20-40% EtOAc in hexanes gradient, HRMS m/z calcd for C28H28N3O3F3 [M+H]+: 512.2156. Found: 512.2155.

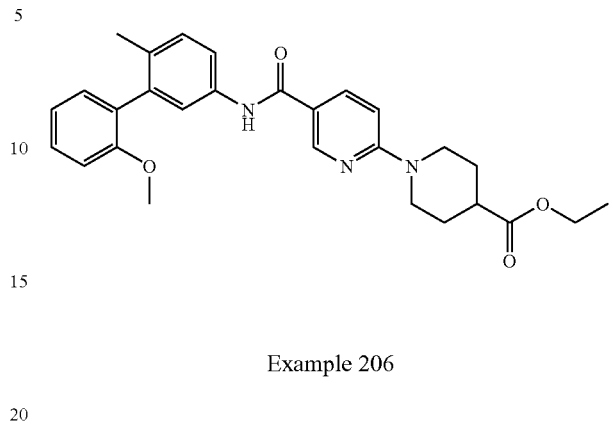

Example 206

5'-(2'-Methoxy-6-methyl-biphenyl-3-ylcarbamoyl)-3,4,5,6-tetrahydro-2H-[1,2']-bipyridinyl-4-carboxylic acid ethyl ester 5'-(2'-Methoxy-6-methyl-biphenyl-3-ylcarbamoyl)-3,4,5,6-tetrahydro-2H-[1,2']bipyridinyl-4-carboxylic acid ethyl ester was prepared from 5'-(3-iodo-4-methyl-phenylcarbamoyl)-3,4,5,6-tetrahydro-2H-[1,2']bipyridinyl-4 carboxylic acid ethyl ester and 2-methoxylphenyl boronic acid following a method similar to the one described in the synthesis of 5'-(2-methyl-biphenyl-4-ylcarbamoyl)-3,4,5,6-tetrahydro-2H-[1,2']bipyridinyl-4-carboxylic acid ethyl ester above. The product was isolated after silica gel column purification with 20-40% EtOAc in hexanes gradient. HRMS m/z calcd for C28H31N3O4 [M+H]+: 474.2388. Found: 474.2387.

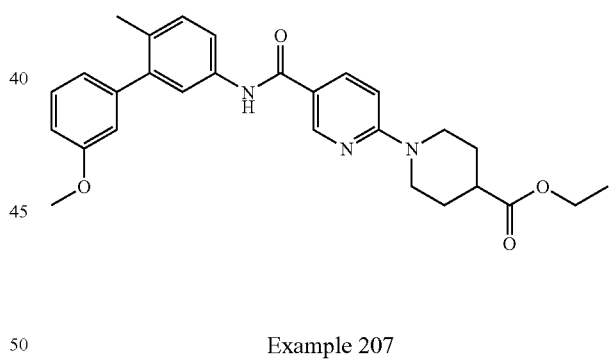

Example 207

5'-(3'-Methoxy-6-methyl-biphenyl-3-ylcarbamoyl)-3,4,5,6-tetrahydro-2H-[1,2']bipyridinyl-4-carboxylic acid ethyl ester 5'-(3'-Methoxy-6-methyl-biphenyl-3-ylcarbamoyl)-3,4,5,6-tetrahydro-2H-[1,2']bipyridinyl-4-carboxylic acid ethyl ester was prepared from 5'-(3-iodo-4-methyl-phenylcarbamoyl)-3,4,5,6-tetrahydro-2H-[1,2']bipyridinyl-4 carboxylic acid ethyl ester and 3-methoxylphenyl boronic acid following a method similar to the one described in the synthesis of 5'-(2-methyl-biphenyl-4-ylcarbamoyl)-3,4,5,6-tetrahydro-2H-[1,2']bipyridinyl-4-carboxylic acid ethyl ester, above. The product was isolated after silica gel column purification with 20-40% EtOAc in hexanes gradient. HRMS m/z calcd for C28H31N3O4 [M+H]+: 474.2388. Found: 474.2390

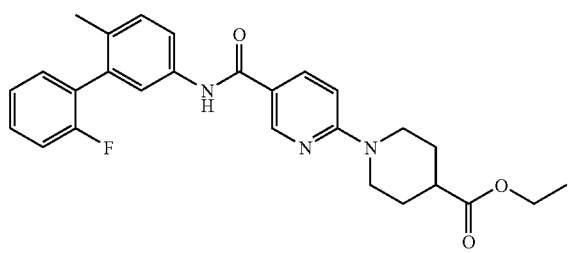

Example 208

5'-(2'-Fluoro-6-methyl-biphenyl-3-ylcarbamoyl)-3,4,5,6-tetrahydro-2H-[1,2']bipyridinyl-4-carboxylic acid ethyl ester 5'-(2'-Fluoro-6-methyl-biphenyl-3-ylcarbamoyl)-3,4,5,6-tetrahydro-2H-[1,2']bipyridinyl-4-carboxylic acid ethyl ester was prepared from 5'-(3-iodo-4-methyl-phenylcarbamoyl)-3,4,5,6-tetrahydro-2H-[1,2']bipyridinyl-4 carboxylic acid ethyl ester and 2-fluorophenyl boronic acid following a method similar to the one described in the synthesis of 5'-(2-methyl-biphenyl-4-ylcarbamoyl)-3,4,5,6-tetrahydro-2H-[1,2']bipyridinyl-4-carboxylic acid ethyl ester, above. The product was isolated after silica gel column purification with 20-40% EtOAc in hexanes gradient. HRMS m/z calcd for C27H28N3O3F [M+H]+: 462.2188. Found: 462.2187.

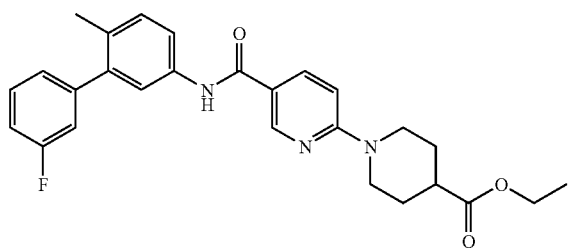

Example 209

5'-(3'-Fluoro-6-methyl-biphenyl-3-ylcarbamoyl)-3,4,5,6-tetrahydro-2H-[1,2']bipyridinyl-4-carboxylic acid ethyl ester 5'-(3'-Fluoro-6-methyl-biphenyl-3-ylcarbamoyl)-3,4,5,6-tetrahydro-2H-[1,2']bipyridinyl-4-carboxylic acid ethyl ester was prepared from 5'-(3-iodo-4-methyl-phenylcarbamoyl)-3,4,5,6-tetrahydro-2H-[1,2']bipyridinyl-4 carboxylic acid ethyl ester and 3-fluorophenyl boronic acid following a method similar to the one described in the synthesis of 5'-(2-methyl-biphenyl-4-ylcarbamoyl)-3,4,5,6-tetrahydro-2H-[1,2']bipyridinyl-4-carboxylic acid ethyl ester, above. The product was isolated after silica gel column purification with 20-40% EtOAc in hexanes gradient. HRMS m/z calcd for C27H28N3O3F [M+H]+: 462.2188. Found: 462.2187.

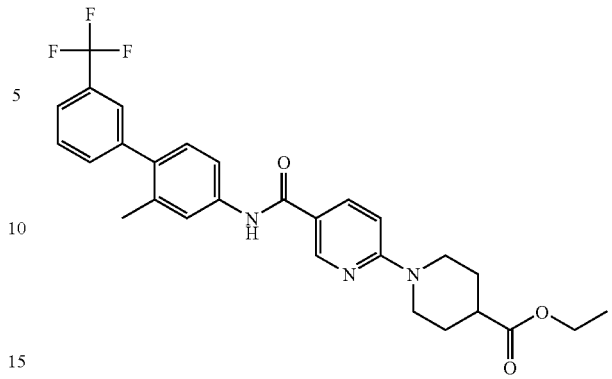

Example 210

5'-(2-Methyl-3'-trifluoromethyl-biphenyl-4-ylcarbamoyl)-3,4,5,6-tetrahydro-2H-[1,2']bipyridinyl-4-carboxylic acid ethyl ester 5'-(2-Methyl-3'-trifluoromethyl-biphenyl-4-ylcarbamoyl)-3,4,5,6-tetrahydro-2H-[1,2']bipyridinyl-4-carboxylic acid ethyl ester was prepared from 5'-(4-iodo-3-methyl-phenylcarbamoyl)-3,4,5,6-tetrahydro-2H-[1,2']bipyridinyl-4 carboxylic acid ethyl ester and 3-trifluorphenyl boronic acid following a method similar to the one described in the synthesis of 5'-(2-methyl-biphenyl-4-ylcarbamoyl)-3,4,5,6-tetrahydro-2H-[1,2']bipyridinyl-4-carboxylic acid ethyl ester, above. The product was isolated after silica gel column purification with 20-40% EtOAc in hexanes gradient. HRMS m/z calcd for C28H28N3O3F3 [M+H]+: 512.2156. Found: 512.2154.

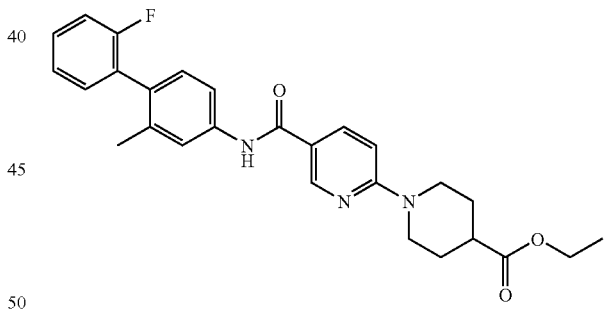

Example 211

5'-(2'-Fluoro-2-methyl-biphenyl-4-ylcarbamoyl)-3,4,5,6-tetrahydro-2H-[1,2']bipyridinyl-4-carboxylic acid ethyl ester 5'-(2'-Fluoro-2-methyl-biphenyl-4-ylcarbamoyl)-3,4,5,6-tetrahydro-2H-[1,2']bipyridinyl-4-carboxylic acid ethyl ester was prepared from 5'-(4-iodo-3-methyl-phenylcarbamoyl)-3,4,5,6-tetrahydro-2H-[1,2']bipyridinyl-4 carboxylic acid ethyl ester and 2-fluorophenyl boronic acid following a method similar to the one described in the synthesis of 5'-(2-methyl-biphenyl-4-ylcarbamoyl)-3,4,5,6-tetrahydro-2H-[1,2']bipyridinyl-4-carboxylic acid ethyl ester, above. The product was isolated after silica gel column purification with 20-40% EtOAc in hexanes gradient. HRMS m/z calcd for C27H28N3O3F [M+H]+: 462.2188. Found: 462.2186.

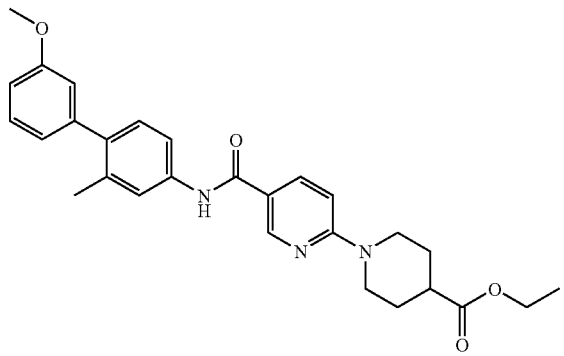

Example 212

5'-(3'-Methoxy-2-methyl-biphenyl-4-ylcarbamoyl)-3, 4,5,6-tetrahydro-2H-[1,2']bipyridinyl-4-carboxylic acid ethyl ester 5'-(3'-Methoxy-2-methyl-biphenyl-4-ylcarbamoyl)-3,4,5, 6-tetrahydro-2H-[1,2']bipyridinyl-4-carboxylic acid ethyl ester was prepared from F-(4-iodo-3-methyl-phenylcarbamoyl)-3,4,5,6-tetrahydro-2H-[1,2']bipyridinyl-4 carboxylic acid ethyl ester and 3-methoxyphenyl boronic acid following a method similar to the one described in the synthesis of 5'-(2-methyl-biphenyl-4-ylcarbamoyl)-3,4,5,6-tetrahydro-2H-[1,2']bipyridinyl-4-carboxylic acid ethyl ester, above. The product was isolated after silica gel column purification with 20-40% EtOAc in hexanes gradient. HRMS m/z calcd for C28H31N3O4 [M+H]+: 474.2388. Found: 474.2388.

Example 213

DGAT Phospholipid FlashPlate Assay

Materials for the assay were: PL-FlashPlate: Phospholipid FlashPlates from PerkinElmer, catalog number SMP108; DAG (1,2-Dioleoyl-sn-glycerol) 10 mM suspended in water containing 0.1% Triton X-100; $^{14}$C-Pal-CoA (palmitoyl coenzyme A, [palmitoyl-1-$^{14}$C]) from PerkinElmer, catalog number NEC-555 with a specific activity of 55 mCi/mmol; and DGAT pellet, with a protein concentration of 9.85 mg/ml.

Aqueous buffers were prepared or purchased as follows: The coating buffer (CB) was purchased from PerkinElmer, catalog number SMP900A; the reaction buffer ($R^B$) was 50 mM Tris-HCl, pH 7.5, 100 mM NaCl, 0.01% BSA in water; the washing buffer (WB) was 50 mM Tris-HCl, pH 7.5, 100 mM NaCl, 0.05% deoxycholic acid sodium salt in water; the dilution buffer (DB) was 50 mM Tris-HCl, pH 7.5, 100 mM NaCl, 1 mM EDTA, 0.2% Triton X-100 in water.

1,2-Dioleoyl-sn-glycerol (DAG, 10 mmoles) was diluted to 500 µM with coating buffer (CB). The diluted DAG solution was then added to 384-well PL-FlashPlates at 60 µl per well, and incubated at room temperature for 2 days. The coated plates were then washed twice with washing buffer (WB) before use. Test compounds were serial diluted to 2000, 666.7, 222.2, 74.1, 24.7, 8.2, 2.7 and 0.9 µM in 100% DMSO. Diluted compound were further diluted 10 fold with reaction buffer (RB). $^{14}$C-Pal-CoA was diluted to 8.3 µM with RB. The DGAT pellet was diluted to 0.13 mg protein/ml with dilution buffer (DB) immediately before it was added to the PL-FlashPlates to start the reaction. 20 µl of the RB-diluted compounds (or 10% DMSO in RB for Total and Blank), 15 µl of RB diluted 14C-Pal-CoA and 15 µl of DB diluted DGAT pellet (DB without DGAT for Blanks) were transferred to each well of the PL-FlashPlates. The reaction mixtures were incubated at 37° C. for 1 hour. The reactions were stopped by washing 3 times with WB. Plates were sealed with Top-seal and read on a Topcount instrument.

Calculation of $IC_{50}$: The $IC_{50}$ values for each compound were generated using an Excel template. The Topcount rpm readings of Total and Blank were used as 0% and 100% inhibition. The percent inhibition values of reactions in the presence of compounds were calculated, and plotted against compound concentrations. All data were fitted into a Dose Response One Site model (4 parameter logistic model) as the following:

$$(A+((B-A)/(1+((x/C)^{\wedge}D)))),$$

while A and B as the bottom and top of the curve (highest and lowest inhibition), respectively, and C as $IC_{50}$ and D as Hill Coefficient of the compound. The results are presented in Table 1:

TABLE 1

| Compound | Activity in DGAT Phospholipid FlashPlate Assay (µM) |
|---|---|
| Example 1 | 2.003 |
| Example 2 | 8.842 |
| Example 3 | 1.248 |
| Example 4 | 0.542 |
| Example 5 | 0.844 |
| Example 6 | 0.063 |
| Example 7 | 0.054 |
| Example 8 | 0.076 |
| Example 9 | 0.081 |
| Example 10 | 0.092 |
| Example 11 | 0.095 |
| Example 12 | 0.105 |
| Example 13 | 0.109 |
| Example 14 | 0.120 |
| Example 15 | 0.137 |
| Example 16 | 0.143 |
| Example 17 | 0.157 |
| Example 18 | 0.164 |
| Example 19 | 0.190 |
| Example 20 | 0.196 |
| Example 21 | 0.202 |
| Example 22 | 0.207 |
| Example 23 | 0.258 |
| Example 24 | 0.283 |
| Example 25 | 0.313 |
| Example 26 | 0.317 |
| Example 27 | 0.324 |
| Example 28 | 0.329 |
| Example 29 | 0.330 |
| Example 30 | 0.340 |
| Example 31 | 0.341 |
| Example 32 | 0.344 |
| Example 33 | 0.415 |
| Example 34 | 0.428 |
| Example 35 | 0.466 |
| Example 36 | 0.492 |
| Example 37 | 0.518 |
| Example 38 | 0.549 |
| Example 39 | 0.577 |
| Example 40 | 0.633 |
| Example 41 | 0.721 |
| Example 42 | 0.725 |
| Example 43 | 0.771 |
| Example 44 | 0.788 |
| Example 45 | 0.840 |

TABLE 1-continued

| Compound | Activity in DGAT Phospholipid FlashPlate Assay (μM) |
|---|---|
| Example 46 | 0.920 |
| Example 47 | 0.965 |
| Example 48 | 1.016 |
| Example 49 | 1.158 |
| Example 50 | 1.172 |
| Example 51 | 1.214 |
| Example 52 | 1.324 |
| Example 53 | 1.437 |
| Example 54 | 1.778 |
| Example 55 | 1.859 |
| Example 56 | 1.915 |
| Example 57 | 2.168 |
| Example 58 | 2.271 |
| Example 59 | 2.847 |
| Example 60 | 4.376 |
| Example 61 | 4.808 |
| Example 62 | 5.020 |
| Example 63 | 5.726 |
| Example 64 | 5.818 |
| Example 65 | 5.878 |
| Example 66 | 6.065 |
| Example 67 | 7.312 |
| Example 68 | 20.283 |
| Example 69 | 0.127 |
| Example 70 | 0.639 |
| Example 71 | 0.711 |
| Example 72 | 0.590 |
| Example 73 | 2.150 |
| Example 74 | 0.779 |
| Example 75 | 5.566 |
| Example 76 | 0.414 |
| Example 77 | 1.106 |
| Example 78 | 1.274 |
| Example 79 | 2.233 |
| Example 80 | 0.282 |
| Example 81 | 11.207 |
| Example 82 | 3.401 |
| Example 83 | 7.275 |
| Example 84 | 6.836 |
| Example 85 | 4.868 |
| Example 86 | 0.150 |
| Example 87 | 0.075 |
| Example 88 | 0.612 |
| Example 89 | 0.174 |
| Example 90 | 0.092 |
| Example 91 | 0.092 |
| Example 92 | 0.130 |
| Example 93 | 0.161 |
| Example 94 | 0.444 |
| Example 95 | 6.379 |
| Example 96 | 0.447 |
| Example 97 | 0.214 |
| Example 98 | 0.488 |
| Example 99 | 1.369 |
| Example 100 | <80 |
| Example 101 | 0.262 |
| Example 102 | 0.068 |
| Example 103 | 0.087 |
| Example 104 | 0.041 |
| Example 105 | 0.043 |
| Example 106 | 0.046 |
| Example 107 | 0.031 |
| Example 108 | 0.792 |
| Example 109 | 0.128 |
| Example 110 | 1.171 |
| Example 111 | 0.411 |
| Example 112 | 0.087 |
| Example 113 | 0.225 |
| Example 114 | 22.253 |
| Example 115 | 0.124 |
| Example 116 | 0.342 |
| Example 117 | 0.052 |
| Example 118 | 0.257 |
| Example 119 | <0.037 |
| Example 120 | 0.360 |
| Example 121 | 1.025 |
| Example 122 | 0.981 |
| Example 123 | 2.270 |
| Example 124 | 0.298 |
| Example 125 | 0.092 |
| Example 126 | 0.090 |
| Example 127 | 0.089 |
| Example 128 | 0.032 |
| Example 129 | 0.083 |
| Example 130 | 0.067 |
| Example 131 | 0.197 |
| Example 132 | 0.192 |
| Example 133 | 0.047 |
| Example 134 | 0.050 |
| Example 135 | 0.041 |
| Example 136 | 0.042 |
| Example 137 | 0.052 |
| Example 138 | 0.054 |
| Example 139 | 0.058 |
| Example 140 | 0.041 |
| Example 141 | 0.055 |
| Example 142 | 1.216 |
| Example 143 | 0.047 |
| Example 144 | 0.426 |
| Example 145 | 0.250 |
| Example 146 | 0.214 |
| Example 147 | 0.108 |
| Example 148 | 0.272 |
| Example 149 | 0.077 |
| Example 150 | 0.092 |
| Example 151 | 0.150 |
| Example 152 | 0.311 |
| Example 153 | 0.130 |
| Example 154 | 0.234 |
| Example 155 | 0.224 |
| Example 156 | 0.312 |
| Example 157 | 0.618 |
| Example 158 | 0.452 |
| Example 159 | 0.636 |
| Example 160 | 0.485 |
| Example 161 | 0.914 |
| Example 162 | <80 |
| Example 163 | 1.2 |
| Example 164 | 1.281 |
| Example 165 | 7.577 |
| Example 166 | 1.556 |
| Example 167 | 4.162 |
| Example 168 | 3.189 |
| Example 169 | 0.557 |
| Example 170 | 0.159 |
| Example 171 | 0.487 |
| Example 172 | 0.794 |
| Example 173 | 0.229 |
| Example 174 | 0.482 |
| Example 175 | 0.490 |
| Example 176 | 0.933 |
| Example 177 | 2.429 |
| Example 178 | 3.308 |
| Example 179 | 33.527 |
| Example 180 | 0.212 |
| Example 181 | 0.084 |
| Example 182 | 0.200 |
| Example 183 | 0.080 |
| Example 184 | 0.047 |
| Example 185 | 0.632 |
| Example 186 | 0.771 |
| Example 187 | 0.950 |
| Example 188 | 0.371 |
| Example 189 | 0.781 |
| Example 190 | 1.743 |
| Example 191 | 0.358 |
| Example 192 | 3.557 |
| Example 193 | 0.403 |
| Example 194 | 0.566 |
| Example 195 | 0.626 |

TABLE 1-continued

| Compound | Activity in DGAT Phospholipid FlashPlate Assay (μM) |
|---|---|
| Example 196 | 0.273 |
| Example 197 | 0.456 |
| Example 198 | 0.188 |
| Example 199 | 0.220 |
| Example 200 | 0.394 |
| Example 201 | 0.576 |
| Example 202 | 0.690 |
| Example 203 | 1.160 |
| Example 204 | 1.719 |
| Example 205 | 3.763 |
| Example 206 | 2.626 |
| Example 207 | 1.170 |
| Example 208 | 1.531 |
| Example 209 | 1.885 |
| Example 210 | 0.643 |
| Example 211 | 1.178 |
| Example 212 | 1.421 |

It is to be understood that the invention is not limited to the particular embodiments of the invention described above, as variations of the particular embodiments may be made and still fall within the scope of the appended claims.

What is claimed is:

1. A compound of formula (I):

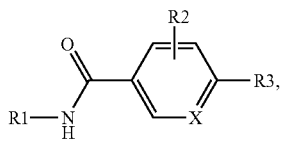

(I)

wherein
X is nitrogen;
R1 is -phenyl, unsubstituted or mono- or di-substituted independently with halogen, lower alkyl, lower alkanoic acid, lower alkanoyl, lower alkyl ester of lower alkanoic acid, haloloweralkyl, unsubstituted phenyl, halophenyl, alkoxyphenyl or phenyl substituted with halolower-alkyl,
R2 is H, halogen or loweralkyl; and
R3 is a piperazine ring, said ring being mono- or di-substituted, independently, with halogen, hydroxy, lower alkoxy, phenyl, phenyl substituted with haloloweralkyl, halophenyl, benzoic acid, lower alkyl ester of benzoic acid, lower alkyl oxadiazole, phenyl-pyridine, lower alkanoyl, lower alkanoic acid, lower alkyl ester of lower alkanoic acid, carbamic acid tert-butyl ester, N-alkyl carbamic acid tert-butyl ester, —CH$_2$-halophenyl, —SO$_2$-phenyl, acetylamino, methyltriazole, —C(O)NSO$_2$—C(CH$_3$)$_3$, benzoic acid benzyl ester, pyridine substituted with C(O)OH, phenyl substituted with lower alkanoic acid, phenyl substituted with lower alkyl ester of lower alkanoic acid, halobenzoic acid, lower alkyl benzoic acid, lower alkyl ester of halobenzoic acid, lower alkyl ester of lower alkyl benzoic acid, lower alkoxy benzoic acid, lower alkyl ester of lower alkoxy benzoic acid, lower alkoxy phenyl, 2,2-dimethyl-4-oxobutyric acid, 2-oxo-ethyl cyclopentanecarboxylic acid, 3,3-dimethyl-5-oxo-pentanoic acid, carbonyl-cyclohexanecarboxylic acid methyl ester, carbonyl-cyclopropane, (2,4-dioxo-thiazolidin-5-yl)-acetyl, carbonyl-ethyl-(3-hydroxy-isoxazol-5-yl), carbonyl-cyclohexanecarboxylic acid, carbonyl-cyclopentanecarboxylic acid, ethanesulfonylaminocarbonyl-cyclohexanecarbonyl, carbonyl-amino-propionic acid ethyl ester, carboxylic acid tert-butylamide, carboxylic acid ethylamide, carbonyl-amino-acetic acid ethyl ester, or —C(O)CH$_2$C(CH$_3$)$_3$;

or a pharmaceutically acceptable salt thereof.

2. The compound of claim 1, wherein R1 is 3 methylester phenyl, 3-tert-butyl phenyl, 3-iodo-4-methyl-phenyl, 4-chloro-3-iodo-phenyl, 3 chloro-4-iodo-phenyl, 3-fluoro-5-iodophenyl, or 3-methoxyphenyl.

3. The compound of claim 1, wherein R2 is hydrogen.

4. The compound of claim 1, wherein R3 is 4-(piperazin-1-yl)-benzoic acid, 6-piperazin-1-yl-nicotinic acid, 3-(4-piperazin-1-yl-phenyl)-propionic acid, 3 chloro-4-piperazin-1-yl-benzoic acid, 3-fluoro-4-piperazin-1-yl-benzoic acid, or 3-methyl-4-piperazin-1-yl-benzoic acid.

5. A compound, wherein said compound is
4-{4-[5-(3-tert-butyl-phenylcarbamoyl)-pyridin-2-yl]-piperazin-1-yl}-benzoic acid;
4-{4-[5-(3-iodo-4-methyl-phenylcarbamoyl)-pyridin-2-yl]-piperazin-1-yl}-benzoic acid;
4{4-[4-(3-tert-butyl-phenylcarbamoyl)-phenyl]-piperazin-1-yl}-benzoic acid;
4-{4-[5-(3-chloro-4-iodo-phenylcarbamoyl)-pyridin-2-yl]-piperazin-1-yl}-benzoic acid;
4-{4-[4-(3-tert-butyl-phenylcarbamoyl)-phenyl]-piperidin-1-yl}-2-methyl-benzoic acid;
4-{4-[4-(3-tert-butyl-phenylcarbamoyl)-phenyl]-piperidin-1-yl}-2-fluoro-benzoic acid;
4-{4-[4-(3-tert-butyl-phenylcarbamoyl)-phenyl]-piperidin-1-yl}-2-chloro-benzoic acid;
4-[4-[4-(3-tert-butyl-phenylcarbamoyl)-phenyl]-piperidin-1-yl]-3-methyl-benzoic acid;
4-[4-[5-(4-chloro-3-iodo-phenylcarbamoyl)-pyridin-2-yl]-piperazin-1-yl]-benzoic acid;
3-methyl-4-{4-[5-(1-ethyl-1H-indol-6-ylcarbamoyl)-pyridin-2-yl]-piperazin-1-yl}-benzoic acid;
4-{4-[4-(3-tert-butyl-phenylcarbamoyl)-2-chloro-phenyl]-piperazin-1-yl}-benzoic acid;
3-chloro-4-[4-[5-(1-ethyl-1H-indol-6-ylcarbamoyl)-pyridin-2-yl]-piperazin-1-yl]-benzoic acid;
(4-{4-[5-(3-tert-butyl-phenylcarbamoyl)-pyridin-2-yl]-piperazin-1-yl}-phenyl)-propionic acid;
2-methyl-4-{4-[5-(1-ethyl-1H-indol-6-ylcarbamoyl)-pyridin-2-yl]-piperazin-1-yl}-benzoic acid;
4-{4-[4-(5-ethyl-4-phenyl-thiazol-2-ylcarbamoyl)-phenyl]-piperazin-1-yl}-benzoic acid;
4-(3-methyl-[1,2,4]oxadiazol-5-yl)-3,4,5,6-tetrahydro-2H[1,2']bipyridinyl-5'-carboxylic acid (5-methyl-4-phenyl-thiazol-2-yl)-amide;
4-[4-[4-(3-tert-butyl-phenylcarbamoyl)-phenyl]-piperidin-1-yl]-benzoic acid;
4-[4-[5-(1-ethyl-1H-indol-6-ylcarbamoyl)-pyridin-2-yl]-piperazin-1-yl]-benzoic acid;
4-{4-[5-(4-tert-butyl-phenylcarbamoyl)-pyridin-2-yl]-piperazin-1-yl}-benzoic acid; or
4-hydroxy-4-(3-trifluoromethyl-phenyl)-3,4,5,6-tetrahydro-2H[1,2']bipyridinyl-5'-carboxylic acid (5-methyl-4-phenyl-thiazol-2-yl)-amide, or pharmaceutically acceptable salts thereof.

6. The compound of claim 1 wherein R3 is piperazine substituted with benzoic acid or an ester of benzoic acid.

7. The compound of claim 6 wherein said compound is 4-{4-[5-(4-tert-butyl-phenylcarbamoyl)-pyridin-2-yl]-piperazin-1-yl}-benzoic acid or pharmaceutically acceptable salts thereof.

8. The compound of claim 6 wherein said compound is 4-{4-[5-(3-iodo-4-methyl-phenylcarbamoyl)-pyridin-2-yl]-piperazin-1-yl}-benzoic acid or pharmaceutically acceptable salts thereof.

9. The compound of claim 6 wherein said compound is 4-{4-[5-(3-chloro-4-iodo-phenylcarbamoyl)-pyridin-2-yl]-piperazin-1-yl}-benzoic acid or pharmaceutically acceptable salts thereof.

10. The compound of claim 6 wherein said compound is 4-{4-[5-(4-chloro-3-iodo-phenylcarbamoyl)-pyridin-2-yl]-piperazin-1-yl}-benzoic acid or pharmaceutically acceptable salts thereof.

11. The compound of claim 1 wherein R3 is piperazine substituted with phenyl, phenyl-lower-alkanoic acid or phenyl lower alkanoic acid lower alkyl ester.

12. The compound of claim 11 wherein said compound is (4-{4-[5-(3-tert butyl-phenylcarbamoyl)-pyridin-2-yl]-piperazin-1-yl}-phenyl)-propionic acid or pharmaceutically acceptable salts thereof.

13. A compound of formula (I):

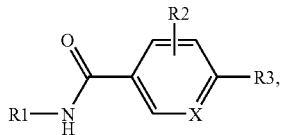

(I)

Wherein
X is nitrogen;
R1 is -phenyl, unsubstituted or mono- or di-substituted independently with lower alkyl, lower alkanoic acid, lower alkanoyl, lower alkyl ester of lower alkanoic acid, haloloweralkyl, unsubstituted phenyl, halophenyl, alkoxyphenyl or phenyl substituted with haloloweralkyl,
R2 is H, halogen or loweralkyl; and
R3 is a piperazine ring, said ring being unsubstituted or mono- or di-substituted, independently, with lower alkyl, halogen, hydroxy, lower alkoxy, phenyl, phenyl substituted with lower alkyl, phenyl substituted with haloloweralkyl, halophenyl, benzoic acid, lower alkyl ester of benzoic acid, lower alkyl oxadiazole, phenylpyridine, lower alkanoyl, lower alkanoic acid, lower alkyl ester of lower alkanoic acid, carbamic acid tert-butyl ester, N-alkyl carbamic acid tert-butyl ester, —CH$_2$-halophenyl, —SO$_2$-phenyl, acetylamino, methyltriazole, —C(O)NSO$_2$—C(CH$_3$)$_3$, benzoic acid benzyl ester, pyridine substituted with C(O)OH, phenyl substituted with lower alkanoic acid, phenyl substituted with lower alkyl ester of lower alkanoic acid, halobenzoic acid, lower alkyl benzoic acid, lower alkyl ester of halobenzoic acid, lower alkyl ester of lower alkyl benzoic acid, lower alkoxy benzoic acid, lower alkyl ester of lower alkoxy benzoic acid, lower alkoxy phenyl, 2,2-dimethyl-4-oxobutyric acid, 2-oxo-ethyl cyclopentanecarboxylic acid, 3,3-dimethyl-5-oxo-pentanoic acid, carbonyl-cyclohexanecarboxylic acid methyl ester, carbonyl-cyclopropane, (2,4-dioxo-thiazolidin-5-yl)-acetyl, carbonyl-ethyl-(3-hydroxy-isoxazol-5-yl), carbonyl-cyclohexanecarboxylic acid, carbonyl-cyclopentanecarboxylic acid, ethanesulfonylaminocarbonyl-cyclohexanecarbonyl, carbonyl-amino-propionic acid ethyl ester, carboxylic acid tert-butylamide, carboxylic acid ethylamide, carbonyl-amino-acetic acid ethyl ester, or —C(O)CH$_2$C(CH$_3$)$_3$;
or a pharmaceutically acceptable salt thereof.

* * * * *